「(12) United States Patent
Bergnes

(10) Patent No.: US 7,439,254 B2
(45) Date of Patent: Oct. 21, 2008

(54) COMPOUNDS, COMPOSITIONS, AND METHODS

(75) Inventor: Gustave Bergnes, Pacifica, CA (US)

(73) Assignee: Cytokinetics, Inc., South San Francisco, CA (US)

( * ) Notice: Subject to any disclaimer, the term of this patent is extended or adjusted under 35 U.S.C. 154(b) by 539 days.

(21) Appl. No.: 11/005,629

(22) Filed: Dec. 7, 2004

(65) Prior Publication Data

US 2005/0234037 A1    Oct. 20, 2005

Related U.S. Application Data

(60) Provisional application No. 60/528,219, filed on Dec. 8, 2003.

(51) Int. Cl.
C07D 471/02 (2006.01)
A61K 31/4375 (2006.01)

(52) U.S. Cl. ..................... 514/300; 546/123

(58) Field of Classification Search ................. 546/113; 514/300
See application file for complete search history.

(56) References Cited

U.S. PATENT DOCUMENTS

| | | |
|---|---|---|
| 3,320,124 A | 5/1967 | Waletzky et al. |
| 3,322,756 A | 5/1967 | Ruschig et al. |
| 3,723,432 A | 3/1973 | Ott et al. |
| 3,740,442 A | 6/1973 | Ott et al. |
| 3,925,548 A | 12/1975 | Oh |
| 3,962,244 A | 6/1976 | Weyer et al. |
| 4,011,324 A | 3/1977 | Althuis |
| 4,281,127 A | 7/1981 | LeMahieu et al. |
| 4,729,996 A | 3/1988 | Wright et al. |
| 4,734,419 A | 3/1988 | Hashimoto et al. |
| 4,808,590 A | 2/1989 | Higa et al. |
| 4,808,595 A * | 2/1989 | Hoffman, Jr. ............. 514/302 |
| 4,857,530 A | 8/1989 | Berman et al. |
| 4,859,670 A | 8/1989 | Kampe et al. |
| 4,866,084 A | 9/1989 | Gunasekera et al. |
| 4,970,226 A | 11/1990 | Sun et al. |
| 4,981,856 A | 1/1991 | Hughes |
| 4,992,550 A | 2/1991 | Hughes |
| 5,037,829 A | 8/1991 | Freyne et al. |
| 5,081,124 A | 1/1992 | Hughes |
| 5,147,875 A | 9/1992 | Coates et al. |
| 5,158,959 A | 10/1992 | Geiger et al. |
| 5,187,167 A | 2/1993 | Hughes |
| 5,204,354 A | 4/1993 | Chakravarty et al. |
| 5,264,439 A | 11/1993 | Greenlee et al. |
| 5,280,027 A | 1/1994 | Andrew et al. |
| 5,316,906 A | 5/1994 | Haugland et al. |
| 5,330,987 A | 7/1994 | Allen et al. |
| 5,342,944 A | 8/1994 | Mohan et al. |
| 5,401,766 A | 3/1995 | Geiger et al. |
| 5,430,148 A | 7/1995 | Webber et al. |
| 5,444,061 A | 8/1995 | Bisset et al. |
| 5,449,678 A | 9/1995 | Pines et al. |
| 5,470,878 A | 11/1995 | Michnick et al. |
| 5,492,915 A | 2/1996 | Dereu et al. |
| 5,561,133 A | 10/1996 | Bisset et al. |
| 5,574,057 A | 11/1996 | Ireland et al. |
| 5,707,861 A | 1/1998 | Sherman et al. |
| 5,707,992 A | 1/1998 | Webber et al. |
| 5,714,493 A | 2/1998 | Myers et al. |
| 5,747,498 A | 5/1998 | Schnur et al. |
| 5,753,664 A | 5/1998 | Aono et al. |
| 5,756,450 A | 5/1998 | Hahn et al. |
| 5,756,502 A | 5/1998 | Padia |
| 5,756,510 A | 5/1998 | Griffin et al. |
| 5,770,595 A | 6/1998 | Klein et al. |
| 5,773,476 A | 6/1998 | Chen et al. |
| 5,777,115 A | 7/1998 | Leigh et al. |
| 5,780,476 A | 7/1998 | Underiner et al. |
| 5,783,577 A | 7/1998 | Houghten et al. |
| 5,789,427 A | 8/1998 | Chen et al. |
| 5,795,898 A | 8/1998 | Brown et al. |
| 5,801,181 A | 9/1998 | Michnick et al. |
| 5,801,182 A | 9/1998 | Klein et al. |
| 5,804,584 A | 9/1998 | Underiner et al. |
| 5,807,862 A | 9/1998 | Klein et al. |
| 5,811,429 A | 9/1998 | Connell et al. |
| 5,817,662 A | 10/1998 | Klein et al. |
| 5,837,703 A | 11/1998 | Kumar et al. |
| 5,852,024 A | 12/1998 | Pines et al. |
| 5,859,018 A | 1/1999 | Brown et al. |
| 5,869,665 A | 2/1999 | Padia |

(Continued)

FOREIGN PATENT DOCUMENTS

AU    B-12617/88    9/1988

(Continued)

OTHER PUBLICATIONS

Chemcats Copyright 2000 ACS, 1998:596123 Chemcats, Maybridge, Apr. 3, 2000, DP 01489, "N2-(3-pyridylmethyl)-4-oxo-3,4-dihydroquinazoline-2-carboxamide," 190437-46-8, Chemical Library.

(Continued)

Primary Examiner—Zinna N Davis
(74) Attorney, Agent, or Firm—Finnegan, Henderson, Farabow, Garrett & Dunner, LLP

(57) ABSTRACT

Compounds useful for treating cellular proliferative diseases and disorders by modulating the activity of KSP are disclosed.

18 Claims, No Drawings

U.S. PATENT DOCUMENTS

| | | |
|---|---|---|
| 5,885,996 A | 3/1999 | Webber et al. |
| 5,891,879 A | 4/1999 | Nagler et al. |
| 5,892,114 A | 4/1999 | Goldmann et al. |
| 5,922,866 A | 7/1999 | Miyata et al. |
| 5,929,081 A | 7/1999 | Brown et al. |
| 5,939,421 A | 8/1999 | Palanki et al. |
| 5,948,775 A | 9/1999 | Koko et al. |
| 5,948,784 A | 9/1999 | Fujiwara et al. |
| 6,008,010 A | 12/1999 | Greenberger et al. |
| 6,136,812 A | 10/2000 | Chenard et al. |
| 6,156,758 A | 12/2000 | Kung et al. |
| 6,207,403 B1 | 3/2001 | Goldstein et al. |
| 6,245,768 B1 | 6/2001 | He et al. |
| 6,545,004 B1 | 4/2003 | Finer et al. |
| 6,545,005 B1 | 4/2003 | Baxter et al. |
| 6,559,160 B1 | 5/2003 | Schall et al. |
| 6,562,831 B1 | 5/2003 | Finer et al. |
| 6,613,798 B1 | 9/2003 | Porter et al. |
| 6,627,755 B1 | 9/2003 | Chenard et al. |
| 6,630,479 B1 | 10/2003 | Finer et al. |
| 6,753,428 B2 | 6/2004 | Bergnes et al. |
| 6,794,379 B2 | 9/2004 | Medina et al. |
| 6,831,085 B1 | 12/2004 | Bergnes et al. |
| 7,041,676 B2 | 5/2006 | McDonald et al. |
| 2001/0046997 A1 | 11/2001 | Abraham et al. |
| 2002/0032207 A1 | 3/2002 | Thompson et al. |
| 2002/0055519 A1 | 5/2002 | Thompson et al. |
| 2002/0165221 A1 | 11/2002 | Baxter et al. |
| 2002/0169159 A1 | 11/2002 | Medina et al. |
| 2002/0198326 A1 | 12/2002 | Aoyama et al. |
| 2003/0018038 A1 | 1/2003 | Thompson et al. |
| 2003/0055054 A1 | 3/2003 | Medina et al. |
| 2003/0091946 A1 | 5/2003 | Uchira et al. |
| 2003/0119834 A1 | 6/2003 | Bamdad |
| 2003/0130293 A1 | 7/2003 | Bamdad |
| 2003/0139398 A1 | 7/2003 | Hoekstra et al. |
| 2003/0139457 A1 | 7/2003 | Baxter et al. |
| 2003/0144350 A1 | 7/2003 | Stevenson et al. |
| 2003/0158188 A1 | 8/2003 | Lee et al. |
| 2003/0158198 A1 | 8/2003 | Lee et al. |
| 2003/0166933 A1 | 9/2003 | Bergnes et al. |
| 2003/0171387 A1 | 9/2003 | Sun et al. |
| 2003/0195211 A1 | 10/2003 | Sadhu et al. |
| 2003/0220338 A1 | 11/2003 | Watkins et al. |
| 2003/0220356 A1 | 11/2003 | Ibrahim et al. |
| 2004/0023996 A1 | 2/2004 | Finer et al. |
| 2004/0048853 A1 | 3/2004 | Bergnes |
| 2004/0067969 A1 | 4/2004 | Bergnes et al. |
| 2004/0077662 A1 | 4/2004 | Zhou et al. |
| 2004/0077667 A1 | 4/2004 | Matsuoka et al. |
| 2004/0077668 A1 | 4/2004 | Feng et al. |
| 2004/0082567 A1 | 4/2004 | Mcdonald et al. |
| 2004/0092561 A1 | 5/2004 | Ruckle et al. |
| 2004/0116438 A1 | 6/2004 | Lu et al. |
| 2004/0142949 A1 | 7/2004 | Bergnes et al. |
| 2004/0192913 A1 | 9/2004 | Bergnes et al. |
| 2005/0234037 A1 | 10/2005 | McDonald et al. |
| 2006/0019988 A1 | 1/2006 | McDonald et al. |

FOREIGN PATENT DOCUMENTS

| | | |
|---|---|---|
| EP | 0 056 637 A1 | 7/1982 |
| EP | 0 286 813 A2 | 2/1988 |
| EP | 0 341 990 A3 | 11/1989 |
| EP | 0 341 990 B1 | 11/1989 |
| EP | 0 360 417 A2 | 3/1990 |
| EP | 0 360 417 A3 | 3/1990 |
| EP | 0 373 891 A2 | 6/1990 |
| EP | 0 431 945 A2 | 6/1991 |
| EP | 0 481 614 A1 | 4/1992 |
| EP | 0 512 676 A1 | 11/1992 |
| EP | 0 534 706 A1 | 3/1993 |
| EP | 0 537 937 A2 | 4/1993 |
| EP | 0 884 310 A1 | 12/1998 |
| EP | 0 884 316 A1 | 12/1998 |
| EP | 0 884 319 A2 | 12/1998 |
| EP | 0 884 319 A3 | 12/1998 |
| EP | 0 900 568 A2 | 3/1999 |
| EP | 0 903 344 A1 | 3/1999 |
| EP | 1 072 952 A1 | 1/2000 |
| EP | 1 174 430 A1 | 1/2002 |
| EP | 1193257 A2 | 4/2002 |
| EP | 1396488 A1 | 3/2004 |
| GB | 2271111 A | 4/1994 |
| HU | 184797 | 10/1984 |
| JP | 62-135473 | 6/1987 |
| JP | 06049070 A2 | 2/1994 |
| JP | 06-148835 | 5/1994 |
| WO | WO 91/12001 A1 | 8/1991 |
| WO | WO 93/11115 A2 | 6/1993 |
| WO | WO 93/23404 A1 | 11/1993 |
| WO | WO 94/21259 A1 | 9/1994 |
| WO | WO 95/16682 A1 | 6/1995 |
| WO | WO 95/24379 A1 | 9/1995 |
| WO | WO 96/06616 A1 | 3/1996 |
| WO | WO 96/19224 A1 | 6/1996 |
| WO | WO 96/28444 A1 | 9/1996 |
| WO | WO 96/39403 A1 | 12/1996 |
| WO | WO 97/10221 A1 | 3/1997 |
| WO | WO 97/43276 A1 | 11/1997 |
| WO | WO 98/26664 A1 | 6/1998 |
| WO | WO 98/29410 A1 | 7/1998 |
| WO | WO 98/34613 A1 | 8/1998 |
| WO | WO 98/58947 A1 | 12/1998 |
| WO | WO 99/08501 A2 | 2/1999 |
| WO | WO 00/00491 A1 | 1/2000 |
| WO | WO 00/07017 A2 | 2/2000 |
| WO | WO 01/74344 A2 | 10/2000 |
| WO | WO 00/69827 A1 | 11/2000 |
| WO | WO 01/16114 A2 | 3/2001 |
| WO | WO 01/19800 A2 | 3/2001 |
| WO | WO 01/23364 A1 | 4/2001 |
| WO | WO 01/23365 A1 | 4/2001 |
| WO | WO 01/25235 A1 | 4/2001 |
| WO | WO 01/30768 A1 | 5/2001 |
| WO | WO 01/32171 A1 | 5/2001 |
| WO | WO 01/32634 A1 | 5/2001 |
| WO | WO 01/42216 A2 | 6/2001 |
| WO | WO 01/66519 A2 | 9/2001 |
| WO | WO 01/70737 A2 | 9/2001 |
| WO | WO 01/81346 A2 | 11/2001 |
| WO | WO 01/95884 A2 | 12/2001 |
| WO | WO 01/98278 A1 | 12/2001 |
| WO | WO 02/04444 A2 | 1/2002 |
| WO | WO 02/08224 A1 | 1/2002 |
| WO | WO 02/09713 A2 | 2/2002 |
| WO | WO 02/09713 A3 | 2/2002 |
| WO | WO 02/14319 A2 | 2/2002 |
| WO | WO 02/083143 A1 | 10/2002 |
| WO | WO 02/094790 A1 | 11/2002 |
| WO | WO 03/027234 A2 | 4/2003 |
| WO | WO 03/035076 A1 | 5/2003 |
| WO | WO 03/35077 A1 | 5/2003 |
| WO | WO 03/039460 A2 | 5/2003 |
| WO | WO 03/043995 A1 | 5/2003 |
| WO | WO 03/049527 A2 | 6/2003 |
| WO | WO 03/049678 A2 | 6/2003 |
| WO | WO 03/049679 A2 | 6/2003 |
| WO | WO 03/050064 A2 | 6/2003 |
| WO | WO 03/050122 A2 | 6/2003 |
| WO | WO 03/063800 A2 | 8/2003 |
| WO | WO 03/070701 A2 | 8/2003 |
| WO | WO 03/070701 A3 | 8/2003 |
| WO | WO 03/076418 A1 | 9/2003 |

| WO | WO 03/079973 A2 | 10/2003 |
| WO | WO 03/094839 A2 | 11/2003 |
| WO | WO 03/097053 A1 | 11/2003 |
| WO | WO 03/099211 A2 | 12/2003 |
| WO | WO 03/103575 A2 | 12/2003 |
| WO | WO 03/105855 A1 | 12/2003 |
| WO | WO 03/106417 A1 | 12/2003 |
| WO | WO 03/106426 A1 | 12/2003 |
| WO | WO 03/106435 A1 | 12/2003 |
| WO | WO 2004/004652 A2 | 1/2004 |
| WO | WO 2004/006916 A1 | 1/2004 |
| WO | WO 2004/009036 A2 | 1/2004 |
| WO | WO 2004/018058 A2 | 3/2004 |
| WO | WO 2004/020599 A2 | 3/2004 |
| WO | WO 2004/022554 A1 | 3/2004 |
| WO | WO 2004/034972 A2 | 4/2004 |
| WO | WO 2004/039774 A2 | 5/2004 |
| WO | WO 2004/064741 A2 | 8/2004 |
| WO | WO 2004/078758 | 9/2004 |

OTHER PUBLICATIONS

Q. Kozhevnikov et al. 4-Quinazolinones. II. 2-(Aminomethyl)-3-aryl-4-quinazolinones. (Russian) Tr Perm Sel-Khoz Inst. 79: 66-72 (1971). Chem Abstracts 78: 390 (1973).

Gupta, C.M. et al. "Drugs acting on the central nervous system. Synthesis of substituted quinazolones and quinazolines and triazepino- and triazocinoquinazolones," J. Med. Chem. 11: 392-395 (1968).

Saari, W.S. et al. "Synthesis and evaluation of 2-pyridinone dervatives as HIV-1-specific reverse transcriptase inhibitors. 2. Analogues of 3-aminopyridin-2(1H)-one," J. Med. Chem. 35: 3792-3802 (1992).

Commercially available from ComGenex, Sep. 16, 1999.

Registry File Compounds from Published References, Maybridge Catalog, Apr. 3, 2000.

Singh et al. Chemical Abstracts, vol. 92, Abstract No. 58712 (1980).

Spirkova et al., Chemical Abstracts, vol. 132, Abstract No. 35672 (1999).

Pandey et al. Chemical Abstracts, vol. 124, Abstract No. 331723 (1996).

Parasharya et al. Chemical Abstracts, vol. 121, Abstract No. 108675 (1994).

Saari et al. Chemical Abstracts, vol. 117, Abstract No. 191731 (1992).

Farghaly et al. Chemical Abstracts, vol. 114, Abstract No. 122242 (1991).

El-Nasser Ossman et al. Chemical Abstracts, vol. 106, Abstract No. 207516 (1987).

Rao et al. Chemical Abstracts, vol. 105, Abstract No. 97416 (1986).

Gupta et al. Chemical Abstracts, vol. 69, Abstract No. 42637 (1968).

Kumar et al. Chemical Abstracts, vol. 102, Abstract No. 142800 (1985).

Chaurasia et al. Chemical Abstracts, vol. 96, Abstract No. 6681 (1982).

Tani et al. Chemical Abstracs, vol. 93, Abstract No. 26374 (1980).

Ager et al. Chemical Abstracts, vol. 86, Abstract No. 83505 (1977).

Kozhevnikov et al. Chemical Abstracts, vol. 78, Abstract No. 16128U (1971).

Bergman et al. "Synthesis of Chrysogine, a Metabolite of Penicillium chrysogenum and some related 2-substituted 4-(3H)-Quinazolinones," Tetrahedron 46: 1295-1310 (1990).

Hart et al. "Synthesis of (-)-Alantrypinone," Tet. Lett. 40: 5429-5432 (1999).

Hart et al. "Synthesis of ent-Alantrypinone" J. Am. Chem. Soc. 123: 5892-5899 (2001).

Mayer et al. "Solid phase synthesis of quinazolinones" Tet. Lett. 38(49):8445-8448 (1997).

Prashad et al. "Reaction of benzoyleneurea and isatoic anhydride with the Vilsmeier reagent" Tet. Lett. 38(8):1313-1316 (1997).

Villalgordo et al. "Solid-phase synthesis of 3H-quinazolin-4-ones based on an aza Wittig-mediated annulation strategy" Synlett 1405-1407 (1998).

Wuckelt et al. "Efficient synthesis of quinazolin-4-ones and axially chiral 2,2'-bis-quinazolin-4-ones by reaction of anthranilic acid derived nucleophiles with oxalic acid-bis(imidoyl)chlorides." Synlett 7:1100-1102 (1999).

Wang et al. "Total synthesis of the quinazolinone alkaloids (-)-Fumiquinazoline G and (-)-Fiscalin B" J. Org. Chem. 63:2432-2433 (1998).

Padia et al. "Novel nonpeptide CCK-B antagonists: Design and development of quinazolinone derivatives as potent, selective, and orally active CCK-B antagonists" J. Med. Chem. 41:1042-1049 (1998).

Singh et al. "4-Quinazolones—II Synthesis of some imidazo [1,5-a] quinazolones" J. Indian Chem. Soc. 46(1):21-25 (1969).

Badawy et al. "Chemistry of Quinazolines: Reinvestigation of the Action of Hydrazine on Thioxo Derivatives" J. Heterocyclic Chem. 22: 1535-1536 (1985).

Yu et al. "Synthesis and x-ray crystallographic analysis of quinazolinone cholecystokinin/gastrin receptor ligands" J. Med. Chem. 35:2534-2542 (1992).

Zher et al. "Reactions of 2-p-anisyl-3(4H), 1-benzoxazin-4-ones with ammonia, primary amines, hydrazine, phenylthydrazine & Grignard reagents" Indian J. Chem. 12:1212-1215 (1974).

Kulkarni et al. "Possible antifertility agents. Part-I. Synthesis of 2-(N,N-substituted-aminomethyl)-3-(2-pyridyl)-4(3H)-oxo-3, 1-quinazolines" J. Indian Chem. LXI:720-721 (1984).

Majo et al. "Dimerization of substituted 2-aminobenzoic acids under Vilsmeier conditions: A novel route to the synthesis of 4-(3H)-quinazolinones" Tet. Lett. 37(28):5015-5018 (1996).

Rathman et al. "Functionalization of 2-methyl-3-o-tolyl-4(3H)-quinazolinone and related compounds through carbanion reactions at the 2-methyl group" J. Org. Chem. 45:2169-2176 (1980).

Padia et al. "Design and synthesis of novel nonpeptide CCK-B receptor antagonists" Bioorg. Med. Chem. Lett. 7(7):805-810 (1997).

Zentmyer et al. "The so-called acylanthranils (3,1,4-benzoxazones). I. Preparation; reactions with water, ammonia, and aniline; structure" J. Organic Chemistry, 14: 967-981 (1949).

Panday, V.K. "Possible Antiparkinsonian Compounds Part XI: Synthesis of 2-aryl/alkyl-3-[β-(3'-4'-dihydroxyphenyl) ethyl]-quinazolin (3H)-4-one and 2-aryl/alkyl-3-[(7'-(phenothiazinyl)-ethyl]-quinazolin/(3H)-4-one" Acta Ciencia Indica 4(3):230-235 (1978).

Tiwari et al. Chemical Abstracts, vol. 96, Abstract No. 142790p (1982).

Fadda et al. "Reactions of a heterocyclic β-enaminoester: Synthesis of pyranopyrimidines and pyrano[3', 2', : 5,6]pyrimidino[2,3-c][1,4]benzoxazine ring system," Indian J. Chemistry 29B: 1020-1024 (1990).

Wagner "Synthesis and Biological Evaluation of Some Derivatives of Pyrido[3, 2-d]pyrimidine" Acta Poloniae Pharmaceutica—Drug Research 51(4-5): 359-363 (1994).

El-Sharief et al. "Oxidation of 3-aminoquinazolinones with lead tetraacetate. A novel synthesis of naphtho-fused azirino-pyrazolo and 1,4,5-oxadiazepino-quinazolinones" J. Chem Research (S): 205-208 (2002).

Chenard et al. "Quinazolin-4-one α-Amino-3-hydroxy-5-methyl-4-isoxazolepropionic Acid (AMPA) Receptor Antagonists: Structure-Activity Relationship of the C-2 Side Chain Tether" J. Med. Chem 44:1710-1717 (2001).

Garg et al. "Synthesis and anti-implantation activity of α-(2-aryl-3-ethyl-4-oxo (3H) quinazolinyl)-α-(substituted styryl)-cyclohexanone thiosemicarbazones" Biol. Mem. 14(2): 180-186 (1988).

Singh et al. "Synthesis and pharmacological screening of some 2-aryl-3-(phenyl-aryl-hydrazonyl)-quinazolin (3H) 4-ones" Indian Drugs 28(2):70-74 (1990).

Ahmad et al. "Monoamine oxidase Inhibitory Activity of 4 (3H)-Quinazolinones of Dopamine" Indian J. of Pharm. Sci. 126-127 (1979).

Tiwari et al. "Possible Antifertility Compounds Part III: Synthesis of 2-Hippuryl-3-Aryl-Quinazolinones" J. Chem. Soc. Pak. 3(4):215-217 (1981).

Pandey, V.K. "Antiparkinsonism and CNS Activities of 2-aryl alkyl-3-(β-(3'-4'-dihydroxyphenyl) Ethyl)-quinazolin (3H) 4-ones" Biol. Mem. 11(2):213-215 (1985).

Monika et al. "Uj kinazolonszarmazekok szintezise es ciklizalasa [1,4]oxazepino- es [1,4]diazepino [3,4-b]kinazolonkka" *Magyar Kemiai Folyoirat* 102(8):343-355 (1996) translated abstract.
Reddy et al. "A New Synthesis of 2-aryl-2H-Pyrazino[2,1-β]Quinazolin-3,6(1H,4H)-Diones" *Synthetic Communications* 21(2): 173-181 (1991).
Monika et al. "Potencialis CCK-antagonista kinazolon-szarmazekok szintezse" *Acta Pharm. Hungarica* 65: 133-136 (1995) translated abstract.
Pandey et al. "Quinazolyl-thiazoles as CNS acting agents" *Acta Pharm.* 46:51-59 (1996).
Reddy et al. "4-Heteryl-β-lactams: A facile synthesis of 1-aryl-4-[isopropylideneamino/methyl-4(3H)-oxoquinazolin-2-yl] azetidin-2-ones" *Indian J. of Chem.* 38B:40-44 (1999).
Reddy et al. "Bisazaheterocycles: Part VII—Synthesis of novel bisquinazolinonyl β-lactams" *Ind. J. of Chem.* 41B:1946-1949 (2002).
Krisztina et al. "Az AGP-alapu folyadek-kromatografias allofazis alkalmazasa kinazolon szarmazekok enantiomerjeinek elvalasztasaban" *Acta Pharma. Hungarica* 73:5-12 (2003) translated abstract.
Reddy et al. "Synthesis of 2-quinazolinonyl imidazolidinones" *Ind. J. of Chem.* 42B:393-396 (2003).
Gyimesi-Forras et al. "Optical Resolution of a Series of Potential Cholecystokinin Antagonist 4(3H)-Quinazolone Derivatives by Chiral Liquid Chromatography on $\alpha_1$-Acid Glycoprotein Stationary Phase" *J. of Chromat. Sci.* 38:430-434 (2000).
Jiang et al. "A Salt Bridge between an N-terminal Coiled Coil of gp41 and an Antiviral Agent Targeted to the gp41 Core Is Important for Anti-HIV-1 Activity" *Biochem. and Biophys. Res. Communications* 270:153-157 92000).
Hughes et al. "Quinazoline Antifolate Thymidylate Synthase Inhibitors: Alkyl, Substituted Alkyl, and Aryl Substituents in the C2 Position" *J. Med. Chem.* 33:3060-3067 (1990).
Hassanein et al. "Sythesis of 2-substituted-10H-[1,2,4] triazino [6,1-b] quinazoline-10-ones and 8,13,14,16 tetrahydronaphtho [2',3',:3,4][1,2,5] triazepino [7,1-b] quinazoline-8,13, 16-triones with biological interest" *Al-Azhar Bull. Sci.* 8(2):417-434 (1997).
Szabo et al. "Nitrogen Bridgehead Compounds: Part 88 [1], Synthesis of 3H,7H-[1,4]Diazepino[3,4-b]quinazoline-3,7-diones" *J. Heterocyclic Chem.* 34(21):21-25 (1997).
Kokosi et al. "Nitrogen Bridgehead Compounds Part 90. An Efficient Versatile Synthesis of 1-Methyl-2-substituted 1,2,3,4-Tetrahydro-6H-Pyrazino[2,1-b]Quinazoline-3,6-Diones" *Heterocycles* 48(9):1851-1866 (1998).
El-Maghraby et al. "Synthesis of Glycylaminothiazoles" *Ind. J. Chem.* 12:1058-1059 (1974).
Hassan et al. "Synthesis and antimicrobial activity of some new N-aminoacyl derivatives of 2-amino-4-phenylthiazole" *Acta Pharm.* 47:159-166 (1997).
West, "Solid State Chemistry and it's Applications," Wiley, New York, 1988, pp. 358 & 365.
Office Action mailed May 7, 2001, for U.S. Appl. No. 09/699,047, filed Oct. 24, 2000.
Office Action mailed Apr. 24, 2002, for U.S. Appl. No. 09/699,047, filed Oct. 24, 2000.
Office Action mailed Feb. 6, 2002, for U.S. Appl. No. 09/723,644, filed Nov. 28, 2000.
Office Action mailed Oct. 21, 2002, for U.S. Appl. No. 09/724,644, filed Nov. 28, 2000.
Office Action mailed Feb. 6, 2002, for U.S. Appl. No. 09/724,712, filed Nov. 28, 2000.
Office Action mailed Apr. 9, 2002, for U.S. Appl. No. 09/724,713, filed Nov. 28, 2000.
Office Action mailed Oct. 21, 2002, for U.S. Appl. No. 09/724,713, filed Nov. 28, 2000.
Office Action mailed Mar. 22, 2002, for U.S. Appl. No. 09/724,897, filed Nov. 28, 2000.
Office Action mailed Dec. 17, 2002, for U.S. Appl. No. 09/724,897, filed Nov. 28, 2000.
Office Action mailed Jul. 11, 2003, for U.S. Appl. No. 09/724,897, filed Nov. 28, 2000.
Office Action mailed May 12, 2004, for U.S. Appl. No. 09/724,897, filed Nov. 28, 2000.
Office Action mailed Jul. 26, 2002, for U.S. Appl. No. 09/724,941, filed Nov. 28, 2000.
Office Action mailed Jan. 13, 2003, for U.S. Appl. No. 09/724,941, filed Nov. 28, 2000.
Office Action mailed Jan. 7, 2004, for U.S. Appl. No. 09/724,941, filed Nov. 28, 2000.
Office Action mailed Jul. 3, 2002, for U.S. Appl. No. 09/724,778, filed Nov. 28, 2000.
Office Action mailed Dec. 27, 2002, for U.S. Appl. No. 09/724,778, filed Nov. 28, 2000.
Office Action mailed Aug. 8, 2003, for U.S. Appl. No. 09/724,778, filed Nov. 28, 2000.
Office Action mailed Dec. 29, 2003, for U.S. Appl. No. 09/724,778, filed Nov. 28, 2000.
Office Action mailed Mar. 30, 2004, for U.S. Appl. No. 09/724,778, filed Nov. 28, 2000.
Office Action mailed Jun. 25, 2004, for U.S. Appl. No. 09/724,778, filed Nov. 28, 2000.
International Search Report mailed Feb. 22, 2001, for PCT Application No. PCT/US00/29585, filed Oct. 26, 2000.
Written Opinion mailed Sep. 21, 2001, for PCT Application No. PCT/US00/29585, filed Oct. 26, 2000.
International Preliminary Examination Report mailed Jan. 17, 2002, for PCT Application No. PCT/US00/29585, filed Oct. 26, 2000.
Office Action mailed Aug. 8, 2003, for U.S. Appl. No. 10/300,967, filed Nov. 20, 2002.
International Search Report mailed Feb. 7, 2003, for PCT Application No. PCT/US02/37410, filed Nov. 20, 2002.
Written Opinion mailed Sep. 9, 2003, for PCT Application No. PCT/US02/37410, filed Nov. 20, 2002.
International Preliminary Examination Report mailed Aug. 11, 2004, for PCT Application No. PCT/US02/37410, filed Nov. 20, 2002.
International Search Report mailed Oct. 31, 2001, for PCT Application No. PCT/US01/13901, filed Apr. 27, 2001.
International Search Report mailed Oct. 17, 2003, for PCT Application No. PCT/US03/18778, filed Jun. 12, 2003.
Office Action mailed Oct. 18, 2004, for U.S. Appl. No. 10/462,002, filed Jun. 12, 2003.
Written Opinion mailed Mar. 2, 2004, for PCT Application No. PCT/US03/18778, filed Jun. 12, 2003.
International Preliminary Examination Report mailed Sep. 8, 2004, for PCT Application No. PCT/US03/18778, filed Jun. 12, 2003.
International Search Report and Written Opinion mailed Dec. 6, 2004, for PCT Application No. PCT/US04/01279, filed Jan. 20, 2004.
International Search Report mailed Aug. 29, 2003, for PCT Application No. PCT/US03/14787, filed May 9, 2003.
Written Opinion mailed Jun. 10, 2004, for PCT Application No. PCT/US03/14787, filed May 9, 2003.
International Preliminary Examination Report mailed Nov. 16, 2004, for PCT Application No. PCT/US03/14787, filed May 9, 2003.
International Search Report mailed Jul. 16, 2004, for PCT Application No. PCT/US03/13627, filed May 2, 2003.
Office Action mailed Nov. 2, 2004, for U.S. Appl. No. 10/366,828, filed Feb. 14, 2003.
International Search Report mailed Aug. 12, 2003, for PCT Application No. PCT/US03/04713, filed Feb. 14, 2003.
Written Opinion mailed Jun. 24, 2004, for PCT Application No. PCT/US03/04713, filed Feb. 14, 2003.
International Preliminary Examination Report mailed Dec. 8, 2004, for PCT Application No. PCT/US03/04713, Feb. 14, 2003.
International Search Report mailed Jul. 9, 2004, for PCT Application No. PCT/US03/23319, filed Jul. 23, 2003.
International Preliminary Examination Report mailed Sep. 30, 2004, for PCT Application No. PCT/US03/23319, filed Jul. 23, 2003.
International Search Report mailed May 20, 2004, for PCT Application No. PCT/US03/26093, filed Aug. 20, 2003.
International Preliminary Examination Report mailed Aug. 5, 2004, for PCT Application No. PCT/US03/26093, filed Aug. 20, 2003.
Office Action mailed Jan. 4, 2005, for U.S. Appl. No. 10/444,283, filed May 22, 2003.

International Search Report mailed Dec. 18, 2003, for PCT Application No. PCT/US03/16500, filed May 22, 2003.
International Preliminary Examination Report mailed Jun. 23, 2004, for PCT Application No. PCT/US03/16500, filed May 22, 2003.
Bergnes et al., "Compounds, Compositions, and Methods," U.S. Appl. No. 10/980,627, filed Nov. 2, 2004.
Bergnes et al., "Compounds, Compositions, and Methods," U.S. Appl. No. 10/982,195, filed Nov. 5, 2004.
Written Opinion mailed Sep. 24, 2004, for PCT Application No. PCT/US02/41309, filed Dec. 20, 2002.
International Search Report mailed Oct. 12, 2004, for PCT Application No. PCT/US03/30788, filed Sep. 30, 2003.
Office Action mailed Feb. 7, 2005, for U.S. Appl. No. 10/435,069, filed May 8, 2005.
International Preliminary Examination Report mailed Jan. 28, 2005, for PCT Application No. PCT/US03/30788, filed Sep. 30, 2003.
Office Action mailed Apr. 27, 2005, for U.S. Appl. No. 10/429,195, filed May 2, 2003.
International Preliminary Examination Report mailed May 9, 2005, for PCT Application No. PCT/US03/13627, filed Sep. 30, 2003.
International Search Report and Written Opinion mailed Apr. 28, 2005, for PCT Application No. PCT/US04/36253, filed Nov. 2, 2004.
Sauter et al., CAPLUS Abstract No. 87:84931 (1977).
Uchida et al., CAPLUS Abstract No. 81:152142 (1974).
Yamada et al., CAPLUS Abstract No. 134:252363 (20001).
Matsuoka et al., CAPLUS Abstract No. 133:150920 (2000).
Nugent et al., CAPLUS Abstract No. 123:143921 (1995).
De Melo et al., CAPLUS Abstract No. 117:143023 (1992).
Irikura et al., CAPLUS Abstract No. 105:42834 (1986).
Kyorin Pharmaceutical Co., Ltd., CAPLUS Abstract No. 103:87901 (1985).
Shuto et al., CAPLUS Abstract No. 90:72134 (1979).
Katagiri et al., CAPLUS Abstract No. 100:51536 (1984).
Hegrand et al., CAPLUS Abstract No. 80:95873 (1974).
Witkop et al., CAPLUS Abstract No. 75:77191 (1971).
Coleman et al., "Inhibitors of the mitotic kinesin spindle protein," *Expert Opin. Ther. Patents*, 14(12):1659-1667 (2004).
Notice of Allowance mailed Apr. 19, 2005, for U.S. Appl. No. 10/462,002, filed Jun. 12, 2003.
International Search Report mailed May 24, 2005 in the International Application No. PCT/US04/38229, filed Dec. 7, 2004.
International Preliminary Examination Report mailed Jun. 22, 2006, for PCT Application No. PCT/US04/38229, filed Dec. 7, 2007.
Supplementary Search Report mailed Aug. 16, 2006, for European Patent Application No. EP 03737085, filed Jun. 12, 2003.

Farghaly, A.M. et al. "Non-steroidal anti-inflammatory agents. III: Synthesis of pyrazole derivatives of 4(3H)-quinazolinones," *Alexandria J. Pharm. Sci.* 4(1): 52-56 (1990).
Dymek, W. et al. "2-Chloromethyl-6-methylquinazolone-4 and its transformations," *Diss. Pharm. Et Pharmacol.* 20(1): 29-34 (1968).
Pattanaik, J.M. et al. "Synthesis and fungicidal activity of 3-aryl-2-(4'-aryl thiazol-2'-ylaminomethyl)quinazol-4(3H)-ones," *Indian J. Chem.* 37B: 1304-1306 (1998).
Gupta, D.P. et al. "Thiazolidinones, azetidinones and formazans of quinazolinones," *Indian J. Chem.* 26B: 1197-1199 (1987).
Parasharya, P.M. et al. "4(3H)-Quinazolones. Part I: 2-Alkyl/arylaminomethyl-3-p-hydroxy/methoxyphenyl-4(3H)-quinazolones," J. Inst. Chemists (India) 64: 184-185 (1992).
Parasharya, P.M. et al. "4-(3H)-Quinazoiones: 2-N-aryl/alkyl-amino-methyl/ethyl-3-p-hydroxypenyl/p-anisyl/p-arylaminoacytoxyphenyl/p-N-arylcarbamoylmethoxyphenyl-4-(3H)-quinazolones," *J. Inst. Chemists* (India) 64: 238-241 (1992).
Matthews, N. et al. "Structure-activity relationships of phenothiazines in inhibiting lymphocyte motility as determined by a novel flow cytometric assay." *Biochem. Pharmacol.* 50(7): 1053-1061 (1995).
List of Purchased Compounds 10/00.
Debnath, A.K. "Structure-Based identification of Small Molecule Antiviral Compounds Targeted to the gp41 Core Structure of the Human Immunodeficiency Virus Type 1," *J. Med. Chem.* 42 (17): 3203-3209 (1999).
Bocskei, Z. et al., "Two Antithrombotic Quinazolone Derivatives." *Acta Crystallogr., Sect. C: Cryst. Struct. Commun.* C51(4): 723-726 (1995).
Szabo, M. et al "Synthesis of Potential CCK Antagonist Quinazolone Derivatives," Chemical Abstracts, vol. 124, No. 13, Abstract No. 176002v (1996).
Ager et al. "Synthesis and Central Nervous System Activity of Quinazolones Related to 2-Methyl-3-(o-tolyl)-4(3*H*) quinazolone (Methaqualone)," *J. Med. Chem.* 20(3): 379-386 (1977).
Tiwari et al. "Synthesis and CNS Activity of 2-Aryl-3(3'-,4'-Dihydroxyphenylethyl) 6-8-substituted-4 (3H)Quinazolinones," *Indian J. Pharma. Sci.* pp. 40-43 (1978).
Rao et al., "Synthesis and Biological Activities of Certain Derivatives of 3-Aryl-4(3H)-quinazolinones, Part-II," *J. Indian Chem. Soc.* LXII. 234-237 (1985).
Registry file compounds from unspecified chemical libraries, no date available.

* cited by examiner

COMPOUNDS, COMPOSITIONS, AND METHODS

This application claims the benefit of U.S. Patent Application No. 60/528,219, filed Dec. 8, 2003, which is hereby incorporated by reference.

This invention relates to compounds which are inhibitors of the mitotic kinesin KSP and are useful in the treatment of cellular proliferative diseases, for example cancer, hyperplasias, restenosis, cardiac hypertrophy, immune disorders, fungal disorders, and inflammation.

Among the therapeutic agents used to treat cancer are the taxanes and vinca alkaloids, which act on microtubules. Microtubules are the primary structural element of the mitotic spindle. The mitotic spindle is responsible for distribution of replicate copies of the genome to each of the two daughter cells that result from cell division. It is presumed that disruption of the mitotic spindle by these drugs results in inhibition of cancer cell division, and induction of cancer cell death. However, microtubules form other types of cellular structures, including tracks for intracellular transport in nerve processes. Because these agents do not specifically target mitotic spindles, they have side effects that limit their usefulness.

Improvements in the specificity of agents used to treat cancer is of considerable interest because of the therapeutic benefits which would be realized if the side effects associated with the administration of these agents could be reduced. Traditionally, dramatic improvements in the treatment of cancer are associated with identification of therapeutic agents acting through novel mechanisms. Examples of this include not only the taxanes, but also the camptothecin class of topoisomerase I inhibitors. From both of these perspectives, mitotic kinesins are attractive targets for new anti-cancer agents.

Mitotic kinesins are enzymes essential for assembly and function of the mitotic spindle, but are not generally part of other microtubule structures, such as in nerve processes. Mitotic kinesins play essential roles during all phases of mitosis. These enzymes are "molecular motors" that transform energy released by hydrolysis of ATP into mechanical force which drives the directional movement of cellular cargoes along microtubules. The catalytic domain sufficient for this task is a compact structure of approximately 340 amino acids. During mitosis, kinesins organize microtubules into the bipolar structure that is the mitotic spindle. Kinesins mediate movement of chromosomes along spindle microtubules, as well as structural changes in the mitotic spindle associated with specific phases of mitosis. Experimental perturbation of mitotic kinesin function causes malformation or dysfunction of the mitotic spindle, frequently resulting in cell cycle arrest and cell death.

Among the mitotic kinesins which have been identified is KSP. KSP belongs to an evolutionarily conserved kinesin subfamily of plus end-directed microtubule motors that assemble into bipolar homotetramers consisting of antiparallel homodimers. During mitosis KSP associates with microtubules of the mitotic spindle. Microinjection of antibodies directed against KSP into human cells prevents spindle pole separation during prometaphase, giving rise to monopolar spindles and causing mitotic arrest and induction of programmed cell death. KSP and related kinesins in other, non-human, organisms, bundle antiparallel microtubules and slide them relative to one another, thus forcing the two spindle poles apart. KSP may also mediate in anaphase B spindle elongation and focussing of microtubules at the spindle pole.

Human KSP (also termed HsEg5) has been described (Blangy, et al., Cell, 83:1159-69 (1995); Whitehead, et al., Arthritis Rheum., 39:1635-42 (1996); Galgio et al., J. Cell Biol., 135:339-414 (1996); Blangy, et al., J Biol. Chem., 272:19418-24 (1997); Blangy, et al., Cell Motil Cytoskeleton, 40:174-82 (1998); Whitehead and Rattner, J. Cell Sci., 111:2551-61 (1998); Kaiser, et al., JBC 274:18925-31 (1999); GenBank accession numbers: X85137, NM004523 and U37426), and a fragment of the KSP gene (TRIP5) has been described (Lee, et al., Mol Endocrinol., 9:243-54 (1995); GenBank accession number L40372). Xenopus KSP homologs (Eg5), as well as *Drosophila* KLP61 F/KRP1 30 have been reported.

Mitotic kinesins, including KSP, are attractive targets for the discovery and development of novel antimitotic chemotherapeutics. Accordingly, it is an object of the present invention to provide compounds, compositions and methods useful in the inhibition of KSP.

In accordance with the objects outlined above, the present invention provides compounds that can be used to treat cellular proliferative diseases. The compounds are KSP inhibitors, such as human KSP inhibitors. The present invention also provides compositions comprising such compounds, and methods utilizing such compounds or compositions, which can be used to treat cellular proliferative diseases In one aspect, the invention relates to methods for treating cellular proliferative diseases, and for treating disorders by inhibiting the activity of KSP. The methods employ at least one chemical entity chosen from compounds of Formula I:

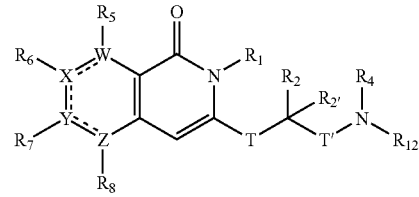

Formula I and pharmaceutically acceptable salts, solvates, crystal forms, chelates, non-covalent complexes, prodrugs, and mixtures thereof, wherein, W, X, Y, and Z are independently —N═, N, —C═, $CR_{18}$, O or S and Z is optionally absent, provided that:
  the ring comprising W, X, Y, and optionally Z is heterocyclic or heteroaromatic;
  no more than two of W, X, Y, and Z is —N═, and
  W, X, or Y can be O or S only when Z is absent;
the dashed lines in the structure depict optional double bonds;
T and T' are independently a covalent bond or optionally substituted lower alkylene;
$R_1$ is chosen from hydrogen, optionally substituted alkyl-, optionally substituted aryl-, optionally substituted aralkyl-, optionally substituted heteroaryl-, and optionally substituted heteroaralkyl-;
$R_2$ and $R_{2'}$ are independently chosen from hydrogen, optionally substituted alkyl-, optionally substituted aryl-, optionally substituted aralkyl-, optionally substituted heteroaryl-, and optionally substituted heteroaralkyl-; or $R_2$ and $R_{2'}$ taken together form an optionally substituted 3- to 7-membered ring;
$R_{12}$ is chosen from hydrogen, optionally substituted alkyl-, optionally substituted aryl-, optionally substituted aralkyl-, optionally substituted heteroaryl-, optionally substituted heteroaralkyl-, —C(O)—R$_3$, and —S(O)$_2$—R$_{3a}$;

R$_3$ is chosen from hydrogen, optionally substituted alkyl-, optionally substituted aryl-, optionally substituted aralkyl-, optionally substituted heteroaryl-, optionally substituted heteroaralkyl-, R$_{15}$O— and R$_{17}$—NH—;

R$_{3a}$ is chosen from optionally substituted alkyl-, optionally substituted aryl-, optionally substituted aralkyl-, optionally substituted heteroaryl-, optionally substituted heteroaralkyl-, and R$_{17}$—NH—;

R$_4$ is chosen from hydrogen, optionally substituted alkyl-, optionally substituted aryl-, optionally substituted aralkyl-, optionally substituted heteroaralkyl-, and optionally substituted heterocyclyl-;

or R$_4$ taken together with R$_{12}$, and the nitrogen to which they are bound, form an optionally substituted 5- to 12-membered nitrogen-containing heterocycle, which optionally incorporates one or two additional heteroatoms, selected from N, O, and S in the heterocycle ring;

or R$_4$ taken together with R$_2$ form an optionally substituted 5- to 12-membered nitrogen-containing heterocycle, which optionally incorporates one or two additional heteroatoms, selected from N, O, and S in the heterocycle ring;

R$_5$, R$_6$, R$_7$, R$_8$, and R$_{18}$ are independently chosen from hydrogen, acyl, optionally substituted alkyl-, optionally substituted alkoxy, halogen, hydroxyl, nitro, cyano, optionally substituted amino, alkylsulfonyl-, alkylsulfonamido-, alkylthio-, carboxyalkyl-, carboxamido-, aminocarbonyl-, optionally substituted aryl and optionally substituted heteroaryl-, provided that R$_5$, R$_6$, R$_7$ and R$_8$ is absent where W, X, Y, or Z, respectively, is —N=, O, S or absent;

R$_{15}$ is chosen from optionally substituted alkyl-, optionally substituted aryl-, optionally substituted aralkyl-, optionally substituted heteroaryl-, and optionally substituted heteroaralkyl-; and R$_{17}$ is hydrogen, optionally substituted alkyl, optionally substituted aryl, optionally substituted aralkyl, optionally substituted heteroaryl, or optionally substituted heteroaralkyl-.

In some embodiments, the methods employ at least one chemical entity chosen from compounds of Formula II:

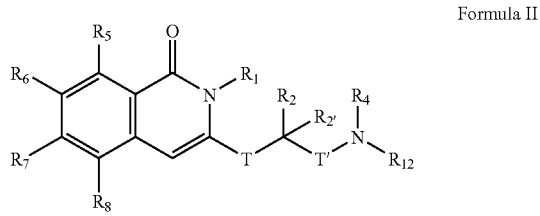

Formula II and pharmaceutically acceptable salts, solvates, crystal forms, chelates, non-covalent complexes, prodrugs, and mixtures thereof, wherein R$_1$, R$_2$, R$_2'$, R$_4$ through R$_8$, R$_{12}$, T, and T' are as defined above and provided that T and T' are not both absent.

In some embodiments, the methods employ at least one chemical entity chosen from compounds of Formula III:

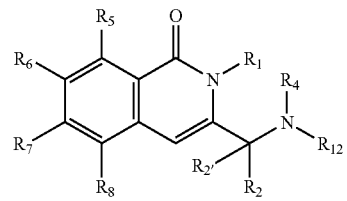

and pharmaceutically acceptable salts, solvates, crystal forms, chelates, non-covalent complexes, prodrugs, and mixtures thereof, wherein R$_1$, R$_3$, R$_{3a}$, R$_{15}$, R$_{17}$ and R$_5$ through R$_8$ are as defined above; and either R$_2$ and R$_{2'}$ are independently chosen from hydrogen, optionally substituted alkyl-, optionally substituted aryl-, optionally substituted aralkyl-, optionally substituted heteroaryl-, and optionally substituted heteroaralkyl- or R$_2$ and R$_{2'}$ taken together form an optionally substituted 3- to 7-membered ring; and R$_{12}$ taken together with R$_4$, and the nitrogen to which they are bound, form an optionally substituted 5- to 12-membered nitrogen-containing heterocycle, which optionally incorporates one or two additional heteroatoms, selected from N, O, and S in the heterocycle ring, provided that such 5-membered nitrogen-containing heterocycle is not an optionally substituted imidazolyl or imidazolinyl ring;

or R$_2$ taken together with R$_4$ form an optionally substituted 5- to 12-membered nitrogen-containing heterocycle, which optionally incorporates one or two additional heteroatoms, selected from N, O, and S in the heterocycle ring; R$_{2'}$ is hydrogen, optionally substituted alkyl-, optionally substituted aryl-, optionally substituted aralkyl-, optionally substituted heteroaryl-, or optionally substituted heteroaralkyl; and R$_{12}$ is chosen from hydrogen, optionally substituted alkyl-, optionally substituted aryl-, optionally substituted aralkyl-, optionally substituted heteroaryl-, optionally substituted heteroaralkyl-, —C(O)—R$_3$, and —S(O)$_2$—R$_{3a}$.

In one aspect, the invention relates to methods for treating cellular proliferative diseases and other disorders that can be treated by inhibiting KSP by the administration of a therapeutically effective amount of at least one chemical entity chosen from compounds of Formula I, II, and III and pharmaceutically acceptable salts, solvates, crystal forms, chelates, non-covalent complexes, prodrugs, and mixtures thereof. Such diseases and disorders include cancer, hyperplasia, restenosis, cardiac hypertrophy, immune disorders, fungal disorders and inflammation. It will be understood that the method can employ one or more of the foregoing compounds.

In another aspect, the invention relates to at least one chemical entity chosen from compounds of Formula I, II, and III and pharmaceutically acceptable salts, solvates, crystal forms, chelates, non-covalent complexes, prodrugs, and mixtures thereof. The invention also relates to pharmaceutical compositions comprising: a therapeutically effective amount of at least one chemical entity chosen from compounds of Formula I, II, and III and pharmaceutically acceptable salts, solvates, crystal forms, chelates, non-covalent complexes, prodrugs, and mixtures thereof and at least one pharmaceutical excipient. In another aspect, the composition further comprises a chemotherapeutic agent other than a chemical entity of the present invention.

As used in the present specification, the following words and phrases are generally intended to have the meanings as set forth below, except to the extent that the context in which they are used indicates otherwise. The following abbreviations and terms have the indicated meanings throughout:

Ac=acetyl
BNB=4-bromomethyl-3-nitrobenzoic acid
Boc=t-butyloxy carbonyl
Bu=butyl
c-=cyclo
CBZ =carbobenzoxy=benzyloxycarbonyl
DBU=diazabicyclo[5.4.0]undec-7-ene
DCM=dichloromethane=methylene chloride=$CH_2Cl_2$
DCE=dichloroethane
DEAD=diethyl azodicarboxylate
DIC=diisopropylcarbodiimide
DIEA=N,N-diisopropylethylamine
DMAP=4-N,N-dimethylaminopyridine
DMF=N,N-dimethylformamide
DMSO=dimethyl sulfoxide
DVB=1,4-divinylbenzene
EEDQ=2-ethoxy-1-ethoxycarbonyl-1,2-dihydroquinoline
Et=ethyl
Fmoc=9-fluorenylmethoxycarbonyl
GC=gas chromatography
HATU=O-(7-Azabenzotriazol-1-yl)-1,1,3,3-tetramethyluronium hexafluorophosphate
HMDS=hexamethyldisilazane
HOAc=acetic acid
HOBt=hydroxybenzotriazole
Me=methyl
mesyl=methanesulfonyl
MTBE=methyl t-butyl ether
NMO=N-methylmorpholine oxide
PEG=polyethylene glycol
Ph=phenyl
PhOH=phenol
PfP=pentafluorophenol
Pht=phthalyl
PPTS=pyridinium p-toluenesulfonate
Py=pyridine
PyBroP=bromo-tris-pyrrolidino-phosphonium hexafluorophosphate
rt=room temperature
sat'd=saturated
s-=secondary
t-=tertiary
TBDMS=t-butyldimethylsilyl
TES=triethylsilyl
TFA=trifluoroacetic acid
THF=tetrahydrofuran
TMOF=trimethyl orthoformate
TMS=trimethylsilyl
tosyl=p-toluenesulfonyl
Trt=triphenylmethyl Alkyl is intended to include linear, branched, or cyclic aliphatic hydrocarbon structures and combinations thereof, which structures may be saturated or unsaturated. Lower-alkyl refers to alkyl groups of from 1 to 5 carbon atoms, such as from 1 to 4 carbon atoms. Examples of lower-alkyl groups include methyl-, ethyl-, propyl-, isopropyl-, butyl-, s- and t-butyl and the like. In some embodiments, alkyl groups are those of $C_{20}$ or below. In some embodiments, alkyl groups are those of $C_{13}$ or below. Cycloalkyl is a subset of alkyl and includes cyclic aliphatic hydrocarbon groups of from 3 to 13 carbon atoms. Examples of cycloalkyl groups include c-propyl-, c-butyl-, c-pentyl-, norbornyl-, adamantyl and the like. Cycloalkyl-alkyl- is another subset of alkyl and refers to cycloalkyl attached to the parent structure through a non-cyclic alkyl-. Examples of cycloalkyl-alkyl- include cyclohexylmethyl-, cyclopropylmethyl-, cyclohexylpropyl-, and the like. In this application, alkyl includes alkanyl-, alkenyl and alkynyl residues; it is intended to include vinyl-, allyl-, isoprenyl and the like. When an alkyl residue having a specific number of carbons is named, all geometric isomers having that number of carbons are intended to be encompassed; thus, for example, "butyl" is meant to include n-butyl-, sec-butyl-, isobutyl and t-butyl-; "propyl" includes n-propyl-, isopropyl-, and c-propyl-.

Alkylene-, alkenylene-, and alkynylene- are other subsets of alkyl-, including the same residues as alkyl-, but having two points of attachment within a chemical structure. Examples of alkylene include ethylene (—$CH_2CH_2$—), propylene (—$CH_2CH_2CH_2$—), dimethylpropylene (—$CH_2C(CH_3)_2CH_2$—) and cyclohexylpropylene (—$CH_2CH_2CH(C_6H_{13})$—). Likewise, examples of alkenylene include ethenylene (—CH=CH—), propenylene (—CH=CH—$CH_2$—), and cyclohexylpropenylene (—CH=CHCH($C_6H_{13}$)—). Examples of alkynylene include ethynylene (—C≡C—) and propynylene (—CH=CH—$CH_2$—).

Cycloalkenyl is a subset of alkyl and includes unsaturated cyclic hydrocarbon groups of from 3 to 13 carbon atoms. Examples of cycloalkenyl groups include c-hexenyl-, c-pentenyl and the like.

Alkoxy or alkoxyl refers to an alkyl group, such as from 1 to 8 carbon atoms, of a straight, branched, or cyclic configuration, or a combination thereof, attached to the parent structure through an oxygen (i.e., the group alkyl-O—). Examples include methoxy-, ethoxy-, propoxy-, isopropoxy-, cyclopropyloxy-, cyclohexyloxy- and the like. Lower-alkoxy refers to alkoxy groups containing one to four carbons.

Acyl refers to groups of from 1 to 8 carbon atoms of a straight, branched, or cyclic configuration or a combination thereof, attached to the parent structure through a carbonyl functionality. Such groups may be saturated or unsaturated, and aliphatic or aromatic. One or more carbons in the acyl residue may be replaced by oxygen, nitrogen (e.g., carboxamido), or sulfur as long as the point of attachment to the parent remains at the carbonyl. Examples include acetyl-, benzoyl-, propionyl-, isobutyryl-, oxalyl-, t-butoxycarbonyl-, benzyloxycarbonyl, morpholinylcarbonyl, and the like. Lower-acyl refers to acyl groups containing one to four carbons.

Amino refers to the group —$NH_2$. The term "substituted amino" refers to the group —NHR or —NRR where each R is independently selected from the group: optionally substituted alkyl-, optionally substituted alkoxy, optionally substituted aminocarbonyl-, optionally substituted aryl-, optionally substituted heteroaryl-, optionally substituted heterocyclyl-, acyl-, alkoxycarbonyl-, sulfanyl-, sulfinyl and sulfonyl-, e.g., diethylamino, methylsulfonylamino, furanyl-oxy-sulfonamino. Substituted amino includes the group —$NR^cCOR^b$, —$NR^cCO_2R^a$, or —$NR^cCONR^bR^c$, where $R^a$ is optionally substituted $C_1$-$C_6$ alkyl-, aryl-, heteroaryl-, aryl-$C_1$-$C_4$ alkyl-, or heteroaryl-$C_1$-$C_4$ alkyl- group;

$R^b$ is H or optionally substituted $C_1$-$C_6$ alkyl-, aryl-, heteroaryl-, aryl-$C_1$-$C_4$ alkyl-, or heteroaryl-$C_1$-$C_4$ alkyl- group; and $R^c$ is hydrogen, alkyl-; aryl- or heteroaryl-;

where each optionally substituted $R^b$ group is independently unsubstituted or substituted with one or more substituents independently selected from $C_1$-$C_4$ alkyl-, aryl-, heterocyclyl-, aryl-$C_1$-$C_4$ alkyl-, heteroaryl-$C_1$-$C_4$ alkyl-, $C_1$-$C_4$ haloalkyl-, —O$C_1$-$C_4$ alkyl, —O$C_1$-$C_4$ alkylphenyl, —$C_1$-$C_4$ alkyl-OH, —O$C_1$-$C_4$ haloalkyl, halogen, —OH, —NH$_2$, —NR$^c$C(NR$^b$)(NR$^b$R$^c$) (i.e. guanidine), —NR$^c$CR$^b$NR$^b$R$^c$, —CNR$^c$NR$^b$R$^c$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for heteroaryl), —CO$_2$H, —C(O)O$C_1$-$C_4$ alkyl-, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl-, —C(O)$C_1$-$C_4$ phenyl-, —C(O)$C_1$-$C_4$ haloalkyl-, —OC(O)$C_1$-$C_4$ alkyl-, —SO$_2$($C_1$-$C_4$ alkyl), —SO$_2$(phenyl), —SO$_2$($C_1$-$C_4$ haloalkyl), —SO$_2$NH$_2$, —SO$_2$NH($C_1$-$C_4$ alkyl), —SO$_2$NH(phenyl), —NHSO$_2$($C_1$-$C_4$ alkyl), —NHSO$_2$(phenyl), and —NHSO$_2$($C_1$-$C_4$ haloalkyl).

Antimitotic refers to a drug for inhibiting or preventing mitosis, for example, by causing metaphase arrest. Some antitumour drugs block proliferation and are considered antimitotics.

Aryl encompasses:
5- and 6-membered carbocyclic aromatic rings, for example, benzene;
bicyclic ring systems wherein at least one ring is carbocyclic and aromatic, for example, naphthalene, indane, and tetralin; and
tricyclic ring systems wherein at least one ring is carbocyclic and aromatic, for example, fluorene.

For example, aryl includes 5- and 6-membered carbocyclic aromatic rings fused to a 5- to 7-membered heterocycloalkyl ring containing 1 or more heteroatoms chosen from N, O, and S. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene.

"Heteroaryl" encompasses:
5- to 7-membered aromatic, monocyclic rings containing one or more, for example, from 1 to 4, or in certain embodiments, from 1 to 3, heteroatoms chosen from N, O and S, with the remaining ring atoms being carbon; and
bicyclic heterocyclic rings containing one or more, for example, from 1 to 4, or in certain embodiments, from 1 to 3, heteroatoms chosen from N, O, and S, with the remaining ring atoms being carbon and wherein at least one heteroatom is present in an aromatic ring.

For example, heteroaryl includes a 5- to 7-membered heterocycloalkyl, aromatic ring fused to a 5- to 7-membered cycloalkyl ring. For such fused, bicyclic heteroaryl ring systems wherein only one of the rings contains one or more heteroatoms, the point of attachment may be at the heteroaromatic ring or the cycloalkyl ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Examples of heteroaryl groups include, but are not limited to, systems (as numbered from the linkage position assigned priority 1), such as 2-pyridyl, 3-pyridyl, 4-pyridyl, 2,3-pyrazinyl, 3,4-pyrazinyl, 2,4-pyrimidinyl, 3,5-pyrimidinyl, 2,3-pyrazolinyl, 2,4-imidazolinyl, isoxazolinyl, oxazolinyl, thiazolinyl, thiadiazolinyl, tetrazolyl, thienyl, benzothiophenyl, furanyl, benzofuranyl, benzoimidazolinyl, indolinyl, pyridizinyl, triazolyl, quinolinyl, pyrazolyl, and 5,6,7,8-tetrahydroisoquinoline. Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene.

Aralkyl—refers to a residue in which an aryl moiety is attached to the parent structure via an alkyl residue. Examples include benzyl-, phenethyl-, phenylvinyl-, phenylallyl and the like. Heteroaralkyl—refers to a residue in which a heteroaryl moiety is attached to the parent structure via an alkyl residue. Examples include furanylmethyl-, pyridinylmethyl-, pyrimidinylethyl and the like.

Aralkoxy—refers to the group —O-aralkyl. Similarly, heteroaralkoxy—refers to the group —O-heteroaralkyl-; aryloxy—refers to the group —O-aryl-; acyloxy—refers to the group —O-acyl-; heteroaryloxy—refers to the group —O-heteroaryl-; and heterocyclyloxy—refers to the group —O-heterocyclyl (i.e., aralkyl-, heteroaralkyl-, aryl-, acyl-, heterocyclyl-, or heteroaryl is attached to the parent structure through an oxygen).

Carboxyalkyl—refers to the group -alkyl-COOH.

Aminocarbonyl refers to the group —CONR$^b$R$^c$, where
$R^b$ is H or optionally substituted $C_1$-$C_6$ alkyl-, aryl-, heteroaryl-, aryl-$C_1$-$C_4$ alkyl-, or heteroaryl-$C_1$-$C_4$ alkyl- group; and
$R^c$ is hydrogen, alkyl-; aryl- or heteroaryl-; and
where each optionally substituted $R^b$ group is independently unsubstituted or substituted with one or more substituents independently selected from $C_1$-$C_4$ alkyl-, aryl-, heterocyclyl-, aryl-$C_1$-$C_4$ alkyl-, heteroaryl-$C_1$-$C_4$ alkyl-, $C_1$-$C_4$ haloalkyl-, —O$C_1$-$C_4$ alkyl-, —O$C_1$-$C_4$ alkylphenyl, —$C_1$-$C_4$ alkyl-OH, —O$C_1$-$C_4$ haloalkyl-, halogen, —OH, —NH$_2$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for heteroaryl), —CO$_2$H, —C(O)O$C_1$-$C_4$ alkyl-, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl-, —C(O)$C_1$-$C_4$ phenyl-, —C(O)$C_1$-$C_4$ haloalkyl-, —OC(O)$C_1$-$C_4$ alkyl-, —SO$_2$($C_1$-$C_4$ alkyl), —SO$_2$(phenyl), —SO$_2$($C_1$-$C_4$ haloalkyl), —SO$_2$NH$_2$, —SO$_2$NH($C_1$-$C_4$ alkyl), —SO$_2$NH(phenyl), —NHSO$_2$($C_1$-$C_4$ alkyl), —NHSO$_2$(phenyl), and —NHSO$_2$($C_1$-$C_4$ haloalkyl). Aminocarbonyl is meant to include carbamoyl-; lower-alkyl carbamoyl-; benzylcarbamoyl-; phenylcarbamoyl-; methoxymethyl-carbamoyl-; and the like.

Halogen or halo refers to fluorine, chlorine, bromine or iodine. Fluorine, chlorine and bromine are preferred. Dihaloaryl-, dihaloalkyl-, trihaloaryl etc. refer to aryl and alkyl substituted with the designated plurality of halogens (here, 2, 2 and 3, respectively), but not necessarily a plurality of the same halogen; thus 4-chloro-3-fluorophenyl is within the scope of dihaloaryl-.

By "heterocycloalkyl" or "heterocyclyl" is meant a single aliphatic ring containing at least 2 carbon atoms in addition to 1-3 heteroatoms independently selected from oxygen, sulfur, and nitrogen, as well as combinations comprising at least one of the foregoing heteroatoms. Suitable heterocycloalkyl groups include, for example (as numbered from the linkage position assigned priority 1), 2-pyrrolinyl, 2,4-imidazolidinyl, 2,3-pyrazolidinyl, 2-piperidyl, 3-piperidyl, 4-piperdyl, and 2,5-piperzinyl. Morpholinyl groups are also contemplated, including 2-morpholinyl and 3-morpholinyl (numbered wherein the oxygen is assigned priority 1).

A leaving group or atom is any group or atom that will, under the reaction conditions, cleave from the starting material, thus promoting reaction at a specified site. Suitable examples of such groups unless otherwise specified are halogen atoms, mesyloxy, p-nitrobenzensulphonyloxy and tosyloxy groups.

Optional or optionally means that the subsequently described event or circumstance may or may not occur, and that the description includes instances where said event or circumstances occurs and instances in which it does not. For example, "optionally substituted alkyl" includes "alkyl" and "substituted alkyl" as defined herein. It will be understood by those skilled in the art with respect to any group containing one or more substituents that such groups are not intended to introduce any substitution or substitution patterns that are sterically impractical and/or synthetically non-feasible and/or inherently unstable.

Substituted alkoxy refers to alkoxy wherein the alkyl constituent is substituted (i.e., —O-(substituted alkyl)). One suitable substituted alkoxy group is "polyalkoxy" or —O-(optionally substituted alkylene)-(optionally substituted alkoxy), and includes groups such as —OCH$_2$CH$_2$OCH$_3$, and residues of glycol ethers such as polyethyleneglycol, and —O(CH$_2$CH$_2$O)$_x$CH$_3$, where x is an integer of about 2-20, such as about 2-10, for example, about 2-5. Another suitable substituted alkoxy group is hydroxyalkoxy or —OCH$_2$(CH$_2$)$_y$OH, where y is an integer of about 1-10, such as about 1-4.

Substituted- alkyl-, aryl-, and heteroaryl- refer respectively to alkyl-, aryl-, and heteroaryl wherein one or more (up to about 5, such as up to about 3) hydrogen atoms are replaced by a substituent independently selected from the group: —R$^a$, —OR$^b$, —O(C$_1$-C$_2$ alkyl)O— (as an aryl substituent), —SR$^b$, —NR$^b$R$^c$, —NR$^c$C(NR$^b$)(NR$^b$R$^c$) (i.e, guanidine), —NR$^c$CR$^b$NR$^b$R$^c$, —CNR$^c$NR$^b$R$^c$, halogen, cyano, nitro, —COR$^b$, —CO$_2$R$^b$, —CONR$^b$R$^c$, —OCOR$^b$, —OCO$_2$R$^a$, —OCONR$^b$R$^c$, —NR$^c$COR$^b$, —NR$^c$CO$_2$R$^a$, —NR$^c$CONR$^b$R$^c$, —SOR$^a$, —SO$_2$R$^a$, —SO$_2$NR$^b$R$^c$, and —NR$^c$SO$_2$R$^a$, where R$^a$ is an optionally substituted C$_1$-C$_6$ alkyl-, aryl-, heteroaryl-, aryl-C$_1$-C$_4$ alkyl-, or heteroaryl-C$_1$-C$_4$ alkyl- group, R$^b$ is H or optionally substituted C$_1$-C$_6$ alkyl-, aryl-, heteroaryl-, aryl-C$_1$-C$_4$ alkyl-, or heteroaryl-C$_1$-C$_4$ alkyl- group;

R$^c$ is hydrogen, alkyl-; aryl- or heteroaryl-; and where each optionally substituted R$^a$ group and R$^b$ group is independently unsubstituted or substituted with one or more substituents independently selected from C$_1$-C$_4$ alkyl-, aryl-, heterocyclyl-, aryl-C$_1$-C$_4$ alkyl-, heteroaryl-C$_1$-C$_4$ alkyl-, C$_1$-C$_4$ haloalkyl-, —OC$_1$-C$_4$ alkyl-, —OC$_1$-C$_4$ alkylphenyl-, —C$_1$-C$_4$ alkyl-OH, —OC$_1$-C$_4$ haloalkyl-, halogen, —OH, —NH$_2$, —C$_1$-C$_4$ alkyl-NH$_2$, —N(C$_1$-C$_4$ alkyl)(C$_1$-C$_4$ alkyl), —NH(C$_1$-C$_4$ alkyl), —N(C$_1$-C$_4$ alkyl)(C$_1$-C$_4$ alkylphenyl), —NH(C$_1$-C$_4$ alkylphenyl), cyano, nitro, oxo (as a substitutent for heteroaryl), —CO$_2$H, —C(O)OC$_1$-C$_4$ alkyl-, —CON(C$_1$-C$_4$ alkyl)(C$_1$-C$_4$ alkyl), —CONH(C$_1$-C$_4$ alkyl), —CONH$_2$, —NHC(O)(C$_1$-C$_4$ alkyl), —NHC(O)(phenyl), —N(C$_1$-C$_4$ alkyl)C(O)(C$_1$-C$_4$ alkyl), —N(C$_1$-C$_4$ alkyl)C(O)(phenyl), —C(O)C$_1$-C$_4$ alkyl-, —C(O)C$_1$-C$_4$ phenyl-, —C(O)C$_1$-C$_4$ haloalkyl-, —OC(O)C$_1$-C$_4$ alkyl-, —SO$_2$(C$_1$-C$_4$ alkyl), —SO$_2$(phenyl), —SO$_2$(C$_1$-C$_4$ haloalkyl), —SO$_2$NH$_2$, —SO$_2$NH(C$_1$-C$_4$ alkyl), —SO$_2$NH(phenyl), —NHSO$_2$(C$_1$-C$_4$ alkyl), —NHSO$_2$(phenyl), and —NHSO$_2$(C$_1$-C$_4$ haloalkyl).

Sulfanyl refers to the groups: —S-(optionally substituted alkyl), —S-(optionally substituted aryl), —S-(optionally substituted heteroaryl), and —S-(optionally substituted heterocyclyl).

Sulfinyl refers to the groups: —S(O)—H, —S(O)-(optionally substituted alkyl), —S(O)-optionally substituted aryl), —S(O)-(optionally substituted heteroaryl), —S(O)-(optionally substituted heterocyclyl); and —S(O)-(optionally substituted amino).

Sulfonyl refers to the groups: —S(O$_2$)—H, —S(O$_2$)-(optionally substituted alkyl), —S(O$_2$)-optionally substituted aryl), —S(O$_2$)-(optionally substituted heteroaryl), —S(O$_2$)-(optionally substituted heterocyclyl), —S(O$_2$)-(optionally substituted alkoxy), —S(O$_2$)-optionally substituted aryloxy), —S(O$_2$)-(optionally substituted heteroaryloxy), —S(O$_2$)-(optionally substituted heterocyclyloxy); and —S(O$_2$)-(optionally substituted amino).

Pharmaceutically acceptable salts refers to those salts that retain the biological effectiveness of the free compound and that are not biologically undesirable or unsuitable for pharmaceutical use, formed with a suitable acid or base, and includes pharmaceutically acceptable acid addition salts and base addition salts. Pharmaceutically acceptable acid addition salts include those derived from inorganic acids such as hydrochloric acid, hydrobromic acid, sulfuric acid, nitric acid, phosphoric acid and the like, and those derived from organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

Pharmaceutically acceptable base addition salts include those derived from inorganic bases such as sodium, potassium, lithium, ammonium, calcium, magnesium, iron, zinc, copper, manganese, aluminum salts and the like. In some embodiments, the pharmaceutically acceptable base addition salts are the ammonium, potassium, sodium, calcium, and magnesium salts. Base addition salts also include those derived from pharmaceutically acceptable organic non-toxic bases, including salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

Protecting group has the meaning conventionally associated with it in organic synthesis, i.e. a group that selectively blocks one or more reactive sites in a multifunctional compound such that a chemical reaction can be carried out selectively on another unprotected reactive site and such that the group can readily be removed after the selective reaction is complete. A variety of protecting groups are disclosed, for example, in T. H. Greene and P. G. M. Wuts, Protective Groups in Organic Synthesis, Third Edition, John Wiley & Sons, New York (1999), which is incorporated herein by reference in its entirety. For example, a hydroxy protected form is where at least one of the hydroxyl groups present in a compound is protected with a hydroxy protecting group. Likewise, amines and other reactive groups may similarly be protected.

Solvate refers to the compound formed by the interaction of a solvent and a compound of Formula I or salt thereof, and as will be understood by those skilled in the art, is the compound or salt with which a solvent is incorporated, for example, into the crystal structure. Suitable solvates of the compounds of the Formula I or a salt thereof are those formed with a pharmaceutically acceptable solvent, including hydrates (i.e., wherein the solvent is water).

Many of the compounds described herein contain one or more asymmetric centers (e.g. the carbon to which $R_2$ and $R_{2'}$ are attached where $R_2$ differs from $R_{2'}$) and may thus give rise to enantiomers, diastereomers, and other stereoisomeric forms that may be defined, in terms of absolute stereochemistry, as (R)— or (S)—. The present invention is meant to include all such possible isomers, including racemic mixtures, optically pure forms and intermediate mixtures. Optically active (R)— and (S)— isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms and rotational isomers are also intended to be included.

When desired, the R— and S-isomers may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where the desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents, or by converting one enantiomer to the other by asymmetric transformation.

The present invention is directed to a class of novel compounds, that can be described as isoquinolone derivatives, that are inhibitors of one or more mitotic kinesins. In some embodiments, the compounds described herein inhibit the mitotic kinesin, KSP, such as human KSP. In some embodiments, the compounds inhibit the mitotic kinesin, KSP, as well as modulating one or more of the human mitotic kinesins selected from the group consisting of HSET (see, U.S. Pat. No. 6,361,993, which is incorporated herein by reference); MCAK (see, U.S. Pat. No. 6,331,424, which is incorporated herein by reference); CENP-E (see, PCT Publication No. WO 99/13061, which is incorporated herein by reference); Kif4 (see, U.S. Pat. No. 6,440,684, which is incorporated herein by reference); MKLP1 (see, U.S. Pat. No. 6,448,025, which is incorporated herein by reference); Kif15 (see, U.S. Pat. No. 6,355,466, which is incorporated herein by reference); Kid (see, U.S. Pat. No. 6,387,644, which is incorporated herein by reference); Mpp1, CMKrp, KinI-3 (see, U.S. Pat. No. 6,461,855, which is incorporated herein by reference); Kip3a (see, PCT Publication No. WO 01/96593, which is incorporated herein by reference); Kip3d (see, U.S. Pat. No. 6,492,151, which is incorporated herein by reference); and RabK6.

The methods of inhibiting a mitotic kinesin comprise contacting an inhibitor of the invention with a kinesin, such as a human kinesin, for example, human KSP or fragments and variants thereof. The inhibition can be of the ATP hydrolysis activity of the KSP kinesin and/or the mitotic spindle formation activity, such that the mitotic spindles are disrupted. Meiotic spindles may also be disrupted.

The present invention provides inhibitors of mitotic kinesins, such as KSP, for example, human KSP, for the treatment of disorders associated with cell proliferation. The compounds described herein can differ in their selectivity and are used to treat diseases of cellular proliferation, including, but not limited to cancer, hyperplasias, restenosis, cardiac hypertrophy, immune disorders, fungal disorders and inflammation.

Accordingly, the present invention relates to methods employing at least one chemical entity chosen from compounds of Formula I:

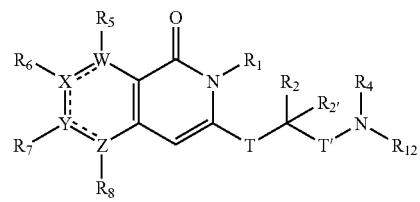

Formula I and pharmaceutically acceptable salts, solvates, crystal forms, chelates, non-covalent complexes, prodrugs, and mixtures thereof, wherein, W, X, Y, and Z are independently —N═, N, —C═, $CR_{18}$, O or S and Z is optionally absent, provided that:
  the ring comprising W, X, Y, and optionally Z is heterocyclic or heteroaromatic;
  no more than two of W, X, Y, and Z is —N═, and
  W, X, or Y can be O or S only when Z is absent;
the dashed lines in the structure depict optional double bonds;
T and T' are independently a covalent bond or optionally substituted lower alkylene;
$R_1$ is chosen from hydrogen, optionally substituted alkyl-, optionally substituted aryl-, optionally substituted aralkyl-, optionally substituted heteroaryl-, and optionally substituted heteroaralkyl-;
$R_2$ and $R_{2'}$ are independently chosen from hydrogen, optionally substituted alkyl-, optionally substituted aryl-, optionally substituted aralkyl-, optionally substituted heteroaryl-, and optionally substituted heteroaralkyl-; or $R_2$ and $R_{2'}$ taken together form an optionally substituted 3- to 7-membered ring;
$R_{12}$ is chosen from hydrogen, optionally substituted alkyl-, optionally substituted aryl-optionally substituted aralkyl-, optionally substituted heteroaryl-, optionally substituted heteroaralkyl-, —C(O)—$R_3$, and —S(O)$_2$—$R_{3a}$;
$R_3$ is chosen from hydrogen, optionally substituted alkyl-, optionally substituted aryl-, optionally substituted aralkyl-, optionally substituted heteroaryl-, optionally substituted heteroaralkyl-, $R_{15}$O— and $R_{17}$—NH—;
$R_{3a}$ is chosen from optionally substituted alkyl-, optionally substituted aryl-, optionally substituted aralkyl-, optionally substituted heteroaryl-, optionally substituted heteroaralkyl-, and $R_{17}$—NH—;

$R_4$ is chosen from hydrogen, optionally substituted alkyl-, optionally substituted aryl-, optionally substituted aralkyl-, optionally substituted heteroaralkyl-, and optionally substituted heterocyclyl-;

or $R_4$ taken together with $R_{12}$, and the nitrogen to which they are bound, form an optionally substituted 5- to 12-membered nitrogen-containing heterocycle, which optionally incorporates one or two additional heteroatoms, selected from N, O, and S in the heterocycle ring;

or $R_4$ taken together with $R_2$ form an optionally substituted 5- to 12-membered nitrogen-containing heterocycle, which optionally incorporates one or two additional heteroatoms, selected from N, O, and S in the heterocycle ring;

$R_5$, $R_6$, $R_7$, $R_8$, and $R_{18}$ are independently chosen from hydrogen, acyl, optionally substituted alkyl-, optionally substituted alkoxy, halogen, hydroxyl, nitro, cyano, optionally substituted amino, alkylsulfonyl-, alkylsulfonamido-, alkylthio-, carboxyalkyl-, carboxamido-, aminocarbonyl-, optionally substituted aryl and optionally substituted heteroaryl-, provided that $R_5$, $R_6$, $R_7$ and $R_8$ is absent where W, X, Y, or Z, respectively, is —N=, O, S or absent;

$R_{15}$ is chosen from optionally substituted alkyl-, optionally substituted aryl-, optionally substituted aralkyl-, optionally substituted heteroaryl-, and optionally substituted heteroaralkyl-; and $R_{17}$ is hydrogen, optionally substituted alkyl-, optionally substituted aryl-, optionally substituted aralkyl-, optionally substituted heteroaryl-, or optionally substituted heteroaralkyl.

In some embodiments, the methods employ at least one chemical entity chosen from compounds of Formula II:

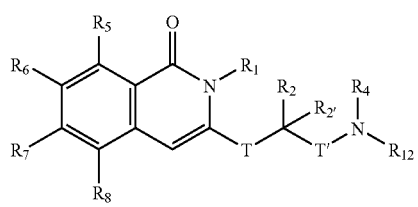

Formula II and pharmaceutically acceptable salts, solvates, crystal forms, chelates, non-covalent complexes, prodrugs, and mixtures thereof, wherein $R_1$, $R_2$, $R_{2'}$, $R_4$ through $R_8$, $R_{12}$, T, and T' are as defined above and provided that T and T' are not both absent.

In some embodiments, the methods employ at least one chemical entity chosen from compounds of Formula III:

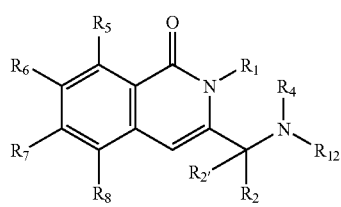

Formula III and pharmaceutically acceptable salts, solvates, crystal forms, chelates, non-covalent complexes, prodrugs, and mixtures thereof, wherein $R_1$, $R_3$, $R_{3a}$, $R_{15}$, $R_{17}$ and $R_5$ through $R_8$ are as defined above; and either $R_2$ and $R_{2'}$ are independently chosen from hydrogen, optionally substituted alkyl-, optionally substituted aryl-, optionally substituted aralkyl-, optionally substituted heteroaryl-, and optionally substituted heteroaralkyl- or $R_2$ and $R_{2'}$ taken together form an optionally substituted 3- to 7-membered ring; and $R_{12}$ taken together with $R_4$, and the nitrogen to which they are bound, form an optionally substituted 5- to 12-membered nitrogen-containing heterocycle, which optionally incorporates one or two additional heteroatoms, selected from N, O, and S in the heterocycle ring, provided that such 5-membered nitrogen-containing heterocycle is not an optionally substituted imidazolyl or imidazolinyl ring;

or $R_2$ taken together with $R_4$ form an optionally substituted 5- to 12-membered nitrogen-containing heterocycle, which optionally incorporates one or two additional heteroatoms, selected from N, O, and S in the heterocycle ring; $R_{2'}$ is hydrogen, optionally substituted alkyl-, optionally substituted aryl-, optionally substituted aralkyl-, optionally substituted heteroaryl-, or optionally substituted heteroaralkyl; and $R_{12}$ is chosen from hydrogen, optionally substituted alkyl-, optionally substituted aryl-, optionally substituted aralkyl-, optionally substituted heteroaryl-, optionally substituted heteroaralkyl-, —C(O)—$R_3$, and —S(O)$_2$—$R_{3a}$.

In certain embodiments, the stereogenic center to which $R_2$ and $R_{2'}$ are attached is of the R configuration.

Compounds of Formula I, II, and III can be prepared by following the procedures described with reference to the Reaction Schemes below.

Unless specified otherwise, the terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents.

In general, esters of carboxylic acids may be prepared by conventional esterification procedures, for example alkyl esters may be prepared by treating the required carboxylic acid with the appropriate alkanol, generally under acidic conditions. Likewise, amides may be prepared using conventional amidation procedures, for example amides may be prepared by treating an activated carboxylic acid with the appropriate amine. Alternatively, a lower-alkyl ester such as a methyl ester of the acid may be treated with an amine to provide the required amide, optionally in presence of trimethylalluminium following the procedure described in Tetrahedron Lett. 48, 4171-4173, (1977). Carboxyl groups may be protected as alkyl esters, for example methyl esters, which esters may be prepared and removed using conventional procedures, one convenient method for converting carbomethoxy to carboxyl is to use aqueous lithium hydroxide.

The salts and solvates of the compounds mentioned herein may as required be produced by methods conventional in the art. For example, if an inventive compound is an acid, a desired base addition salt can be prepared by treatment of the free acid with an inorganic or organic base, such as an amine (primary, secondary, or tertiary); an alkali metal or alkaline earth metal hydroxide; or the like. Illustrative examples of suitable salts include organic salts derived from amino acids such as glycine and arginine; ammonia; primary, secondary, and tertiary amines; such as ethylenediamine, and cyclic amines, such as cyclohexylamine, piperidine, morpholine, and piperazine; as well as inorganic salts derived from sodium, calcium, potassium, magnesium, manganese, iron, copper, zinc, aluminum, and lithium.

If a compound is a base, a desired acid addition salt may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, maleic acid, succinic acid, mandelic acid, fumaric acid, malonic acid, pyruvic acid, oxalic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid, methanesulfonic acid, ethanesulfonic acid, or the like.

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can, of course, also be used.

The compounds of Formula I, II, and III can be prepared by following the procedures described in U.S. patent application Ser. No. 10/462,002 and corresponding PCT Application No. PCT/US03/18778; U.S. patent application Ser. No. 10/366,828 and corresponding PCT Application No. US03/04713; PCT Publication Nos. WO 01/30768, WO 01/98278, PCT WO 03/39460, WO 03/49678, WO 03/50122, WO 03/49527, WO 0349679, and WO 03/50064, each of which is incorporated herein by reference for all purposes, and with reference to the Reaction Schemes below.

The optionally substituted benzoic acids of Formula 101 and the other reactants are commercially available, e.g., from Aldrich Chemical Company, Milwaukee, Wis. or may be readily prepared by those skilled in the art using commonly employed synthetic methodology.

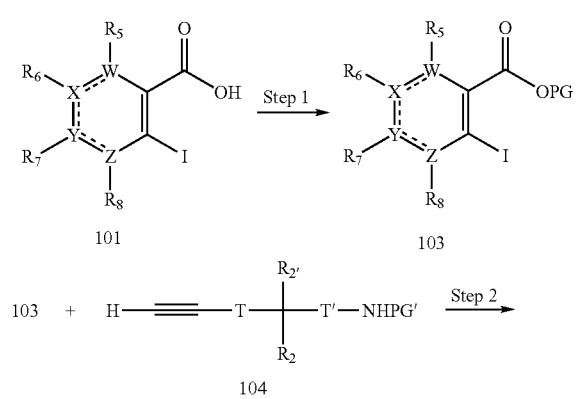

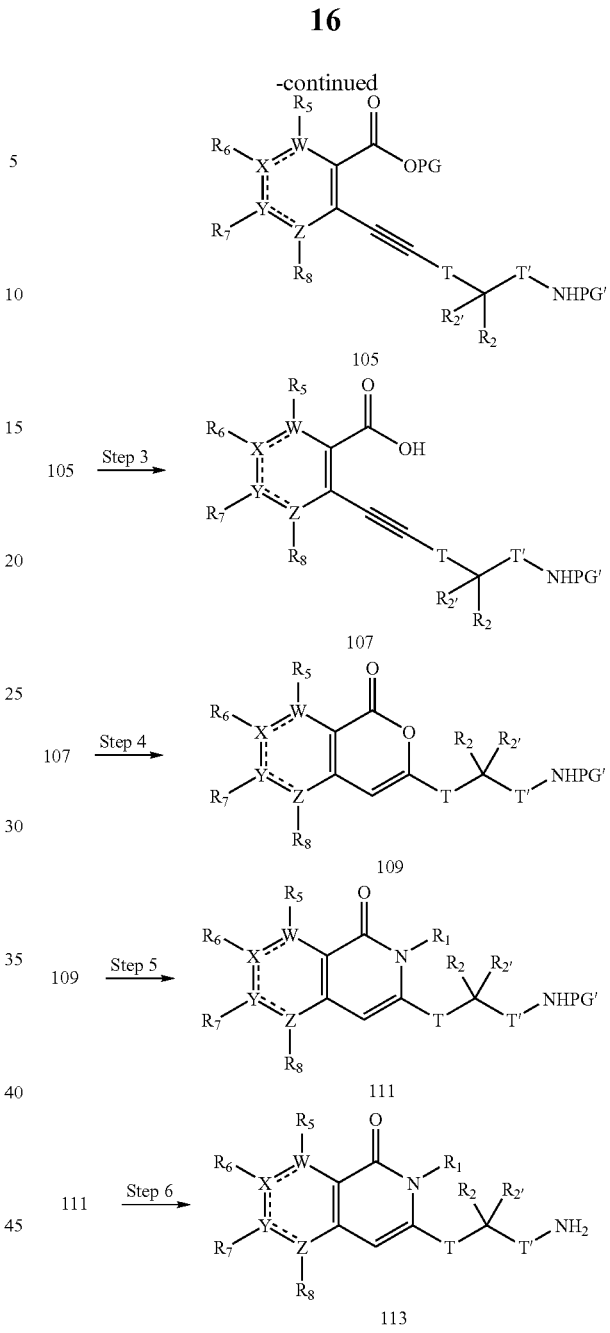

Preparation of Compounds of Fromula 103

Referring to Reaction Scheme 1, Step 1, an optionally substituted carboxylic acid of Formula 101 is protected with a suitable protecting group. For example, the following procedure is used to prepare esters of the carboxylic acid. A solution of a compound of Formula 101 and thionyl chloride in a polar aprotic solvent (such as DMF) is warmed gently until the mixture becomes homogeneous. The solution is concentrated. A lower alkanol, such as methanol, is then added. The corresponding, optionally substituted compound of Formula 103 is isolated and purified.

Preparation of Compounds of Formula 105

Referring to Reaction Scheme 1, Step 2, a compound of Formula 103 is coupled to a compound of Formula 104. A variety of reaction conditions can be used to effect this coupling, e.g., Sonogashira coupling conditions using a palladium catalyst such as (diphenylphosphineferrocenyl)dichloropalladium or tris (dibenzylidenacetone)-dipalladium; a base such as cesium carbonate or triethylamine; and ligands such as triphenylarsine or triphenylphosphine; Stille conditions using a palladium catalyst such as tris (dibenzylidinacetone)-dipalladium; lithium chloride; and triphenylarsine; or Suzuki coupling conditions wherein the compound of Formula 104 is treated with a borane such as catechol borane or 9-borabicyclo[3.3.1]nonane and the two fragments are coupled using a palladium catalyst such as those described above, a base such as cesium carbonate, and triphenylarsine.

In some embodiments, a mixture of a compound of Formula 103; a slight excess (such as about 1.1 equivalents) of an acetylenic compound of Formula 104; a palladium catalyst such as dichlorobis(triphenylphosphine)palladium(II), for example, about 0.025 equivalents of the catalyst; and cuprous iodide in a base such as triethylamine is heated at about 50° C. The corresponding, optionally substituted compound of Formula 105 is isolated and purified.

Preparation of Compounds of Formula 107

Referring to Reaction Scheme 1, Step 3, the protecting group is then removed from the carboxylic acid. When the protecting group is a lower alkyl ester, it can be removed by treatment with aqueous alcoholic base at an elevated temperature. For example, methyl esters can be converted to the corresponding carboxylic acid by treatment of the ester with potassium hydroxide in a 1:1:1 solution of methanol, THF, and alcohol at about 50° C. for 30 minutes. The corresponding, optionally substituted compound of Formula 107 is isolated and used without further purification.

Preparation of Compounds of Formula 109

Referring to Reaction Scheme 1, Step 4, bis(acetonitrile)dichloropalladium (about 0.050 equivalents) is added to a solution of a compound of Formula 107 and a base, such as triethylamine, in a nonpolar, aprotic solvent such as THF. The solution is maintained at an elevated temperature, such as about 50° C. The corresponding, optionally substituted isochromen-1-one of Formula 109 is isolated and purified.

Preparation of Compounds of Formula 111

Referring to Reaction Scheme 1, Step 5, a solution of isochromen-1-one of Formula 109 and an excess (such as about 3 equivalents) of a primary amine of formula $R_1NH_2$ in a nonpolar solvent such as toluene is heated at reflux, such as about 140° C. The resulting amide is isolated and dissolved in a polar, protic solvent such as methanol. Aqueous acid, such as about 5% aqueous hydrochloric acid is added to the solution which is then heated to about 50° C. Additional aqueous alcholic acid may be added if required to complete the reaction. The corresponding, optionally substituted 2H-isoquinolin-1-one of Formula 111 is isolated and purified.

Preparation of Compounds of Formula 113

Referring to Reaction Scheme 1, Step 6, the protecting group is removed from the primary amine. In some embodiments, the protecting group is Boc and its removal can be accomplished through treatment with aqueous TFA at room temperature. The product, a compound of Formula 113 is isolated and can be used without further purification.

In certain embodiments, a particular stereoconfiguration for the $R_2$ substituent, such as the (R) isomer, can be obtained. An amine of Formula 113 is dissolved in an inert organic solvent (such as IPA) and warmed to 60° C. In a separate vessel, a resolving agent (such as dibenzoyl-D-tartaric acid) is dissolved, such as in the same warm solvent, and then quickly added (with agitation) to the warm amine solution. The reaction mixture is left to crystallize by cooling to room temperature over 16 hours under continuing agitation. The desired isomer, e.g., the (R) isomer is isolated and purified in the usual manner.

For the sake of brevity in the remaining description of the synthesis of compounds of Formula I, II, or III, it should be understood that either single isomer or a mixture of isomers may be employed to give the corresponding product.

Reaction Scheme 2

Preparation of Formula 203

Referring to Reaction Scheme 2, Step 1, to a solution of a compound of Formula 113 is added successively a slight excess (such as about 1.2 equivalents) of an aldehyde comprising $R_{4'}$ (i.e., a compound having the formula $R_4CHO$ where $R_4CH_2$— is equivalent to $R_4$ and $R_4$ is as described above or is a protected precursor to such a substituent, e.g., (3-oxo-propyl)-carbamic acid tert-butyl ester) and a reducing agent such as sodium triacetoxyborohydride. The resulting mixture is stirred for several hours. The product, a compound of Formula 203 is isolated and purified.

Preparation of Formula 205

Referring to Reaction Scheme 2, Step 2, to a solution of a compound of Formula 203 and an amine base such as diisopropylethylamine in a nonpolar, aprotic solvent such as dichloromethane is added an $R_3$ acyl chloride (such as Cl—C(O)—$R_3$ where $R_3$ is as described above). The resulting solution is stirred under nitrogen at room temperature for several hours. The product, a compound of Formula 205 is isolated and purified.

Optionally, any protecting groups on compounds of Formula 205 are then removed. For example, if $R_4$ comprises a protected amine wherein the protecting group is a Boc group, the Boc group can be removed by treatment of the compound of Formula 205 with an acid such as trifluoroacetic acid in a nonpolar, aprotic solvent such as dichloromethane, while maintaining the reaction at about room temperature. The reaction is monitored e.g., by TLC. Upon completion, the product is isolated and purified.

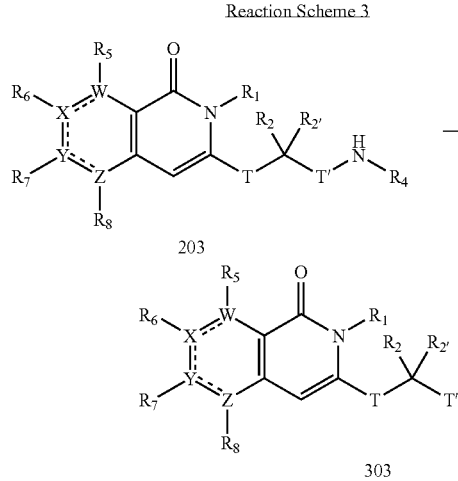

Referring to Reaction Scheme 3, to a solution of a compound of Formula 203 and an amine base such as diisopropylethylamine in a nonpolar, aprotic solvent such as dichloromethane is added a compound having the formula Cl—S(O)$_2$—R$_{3a}$ or O—(S(O)$_2$—R$_{3a}$)$_2$ where R$_{3a}$ is as described above. The resulting solution is stirred under nitrogen at room temperature for several hours. The product, a compound of Formula 303 is isolated and purified.

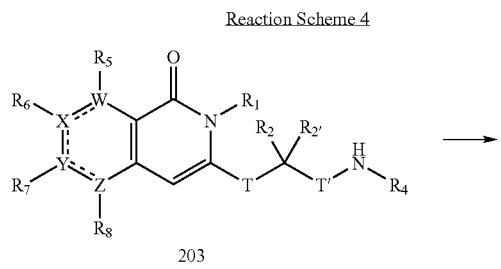

Referring to Reaction Scheme 4, to a solution of a compound of Formula 203 and an amine base such as diisopropylethylamine in a nonpolar, aprotic solvent such as dichloromethane is added a compound having the formula X—R$_{12}$ where R$_{12}$ is as described above and X is a leaving group. The resulting solution is stirred under nitrogen at room temperature or with heat for several hours. The product, a compound of Formula 403 is isolated and purified.

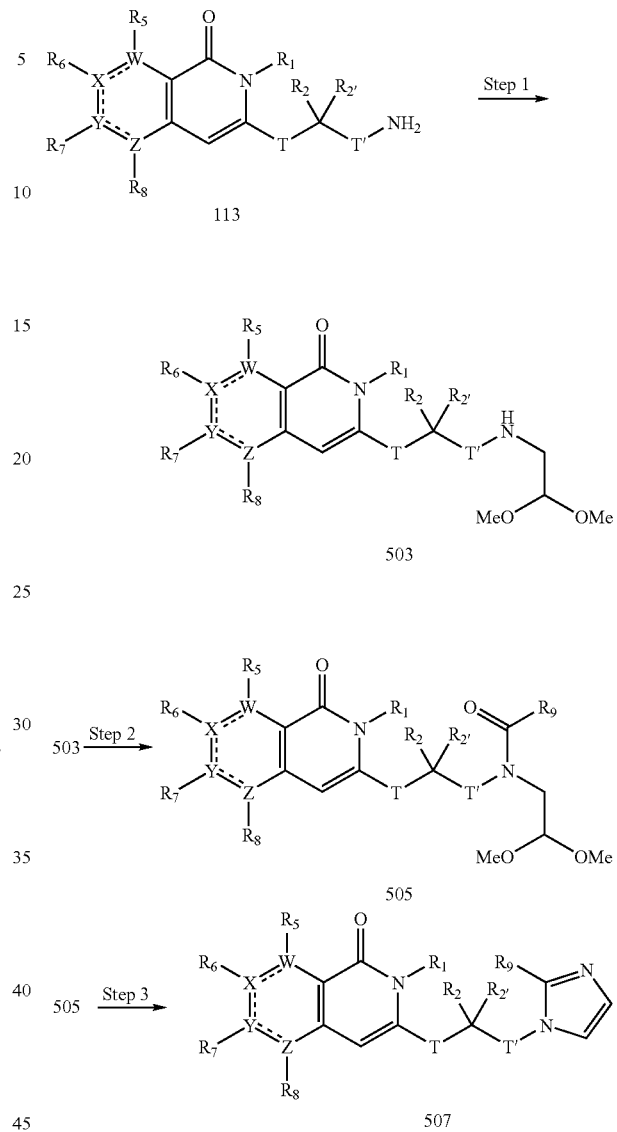

Preparation of Formula 503

Referring to Reaction Scheme 5, Step 1, to an optionally substituted compound of Formula 113 dissolved in a polar, aprotic solvent (such as DMF) in the presence of a base (such as potassium carbonate) is added one equivalent of an optionally substituted suitably protected aldehyde wherein such aldehyde further comprises a leaving group, such as a halide. The solution is heated at reflux, monitoring completion of the reaction (e.g., by TLC). The reaction mixture is cooled and the corresponding, optionally substituted compound of Formula 503 is isolated and purified.

Preparation of Formula 505

Referring to Reaction Scheme 5, Step 2, to an optionally substituted compound of Formula 503 in an inert solvent (such as dichloromethane) in the presence of about 1.5 molar equivalents of an amine base (such as triethylamine) is added about 1.5 molar equivalents of an R$_9$ acid chloride, such as, Cl—C(O)—R$_9$, where R$_9$ is as described herein. The reaction takes place, with stirring, at room temperature over a period of 4 to 24 hours. Completion is monitored, e.g., by TLC. The corresponding compound of Formula 505 is isolated and purified.

Preparation of Formula 507

Referring to Reaction Scheme 5, Step 3, a solution of a compound of Formula 505 and an excess of ammonium acetate in acetic acid is heated at reflux for 1-4 hours. Completion is monitored, e.g., by TLC. The corresponding compound of Formula 507 is isolated and purified.

Reaction Scheme 6

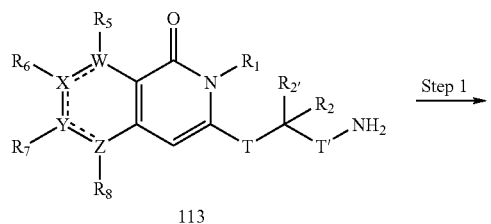

113

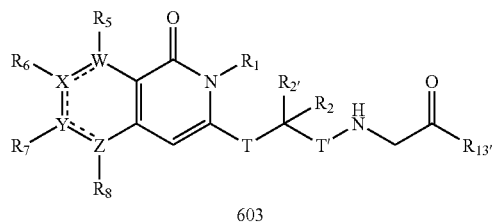

603

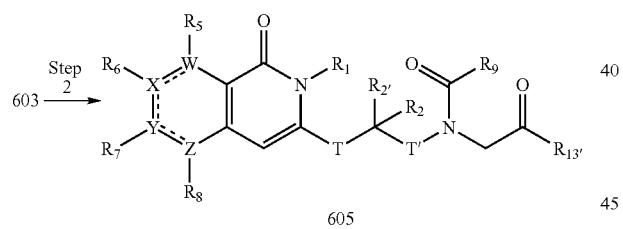

605

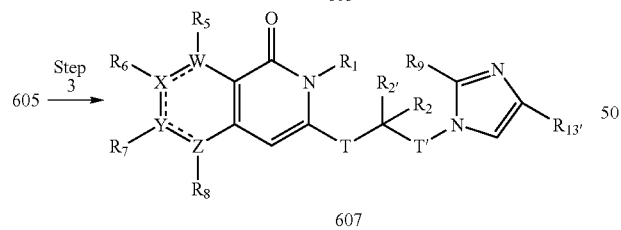

607

Preparation of Formula 603

Referring to Reaction Scheme 6, Step 1, a suspension of a compound of Formula 113, an alpha-haloketone reagent of the Formula $R_{13'}(CO)CH_2X$ wherein X is a leaving group (such as a halide) and $R_{13'}$ is as described herein, and about an equivalent of a base, such as potassium carbonate in a polar, aprotic solvent such as DMF is stirred at room temperature. The reaction is diluted with water and the resulting solid, a compound of Formula 603, is used in the subsequent step without further purification.

Preparation of Formula 605

Referring to Reaction Scheme 6, Step 2, a solution of the compound of Formula 603, about an equivalent of an amine base, such as triethylamine and about an equivalent of an acid chloride (such as a compound of Formula $R_9$—COCl) in an organic solvent such as methylene chloride is stirred at room temperature for several hours. Completion is monitored, e.g., by TLC. The corresponding compound of Formula 605 is isolated and purified.

Preparation of Formula 607

Referring to Reaction Scheme 6, Step 3, a solution of a compound of Formula 605 and an excess of ammonium acetate in acetic acid is heated at reflux using a Dean-Stark trap and condenser. Completion is monitored, e.g., by TLC. The corresponding compound of Formula 607 is isolated and purified.

Optionally, in the event that group $R_{13'}$ comprises a functionality bearing a protecting group, the protecting group is removed. Thus, if $R_{13'}$ further comprises an amine bearing a Pht group, the protecting group is removed by treatment of a solution of a compound of Formula 607 with an excess of anhydrous hydrazine in a polar, protic solvent such as ethanol. The solution is refluxed and then cooled to about 50° C. and any precipitate is filtered off. The filtrate is concentrated in vacuo and purified to yield the corresponding free amine.

Reaction Scheme 7

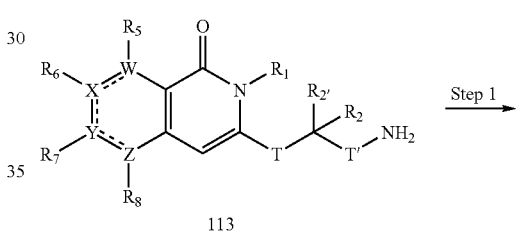

113

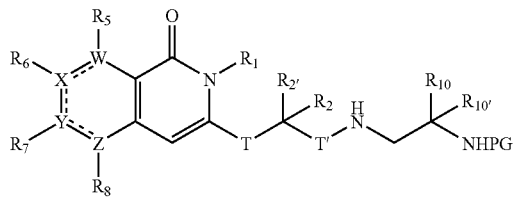

703

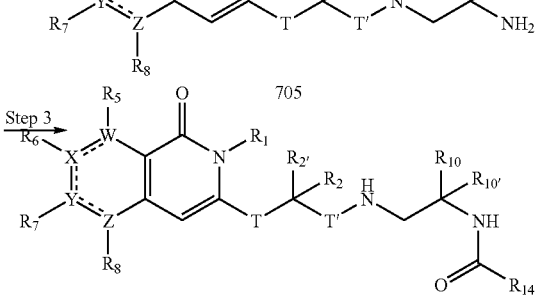

705

707

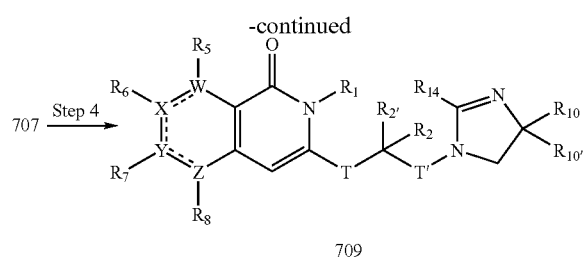

709

Preparation of Formula 703

Referring to Reaction Scheme 7, Step 1, reductive amination of amines of Formula 113 (prepared as described in WO 0130768) with an optionally substituted, aldehyde-containing carbamic acid ester (Seki et. al. *Chem. Pharm. Bull.* 1996, 44, 2061) gives urethane intermediates. Removal of the Boc protecting group furnishes an amine of Formula 705.

More specifically, to a solution of a compound of Formula 113 and an equivalent of a suitably protected aldehyde (Seki et. al. *Chem. Pharm. Bull.* 1996, 44, 2061) in dichloromethane is added a slight excess of a reducing agent, such as sodium triacetoxyborohydride. The resultant cloudy mixture is maintained at ambient temperature. Completion is monitored, e.g., by TLC. The corresponding compound of Formula 703 is isolated and used in the subsequent step without purification.

Preparation of Formula 705

Referring to Reaction Scheme 7, Step 2, the amine protecting group, PG, is then removed. For example, when PG is Boc, to a solution of a compound of Formula 703 in a nonpolar, aprotic solvent such as dichloromethane is added a strong acid such as trifluoroacetic acid. The resultant solution is maintained at ambient temperature overnight and concentrated under reduced pressure. The residue is isolated to give a compound of Formula 705 which was used in the subsequent step without purification.

Preparation of Formula 707

Referring to Reaction Scheme 7, Step 3, to a solution of a compound of Formula 705 in a nonpolar, aprotic solvent such as dichloromethane is added an excess, such as about two equivalents, of an amine base such as triethylamine, followed by about an equivalent or slight excess of an acid chloride of the formula $R_{14}COCl$. The resultant solution is stirred at ambient temperature for about 3 hours. Completion is monitored, e.g., by TLC. The corresponding compound of Formula 707 is isolated and purified.

Preparation of Formula 709

Referring to Reaction Scheme 7, Step 4, a solution of a compound of Formula 707 in an excess of phosphorus oxychloride is heated at reflux. After 8 hours, the reaction mixture is allowed to cool to ambient temperature and concentrated under reduced pressure. The corresponding compound of Formula 709 is isolated and purified.

Reaction Scheme 8

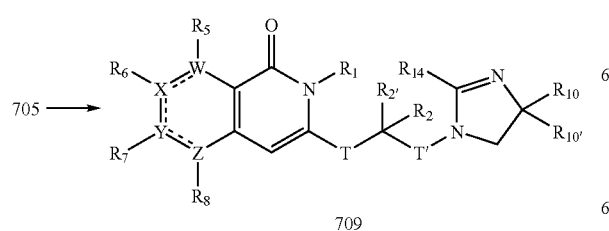

709

Preparation of Formula 709

As an alternative to Steps 3 and 4 of Reaction Scheme 7, acylation of primary amines of Formula 705, followed by acetic acid mediated cyclization, can proceed without isolation of the intermediate amides to provide the target compound of Formula 709. This route is shown in Reaction Scheme 8.

More specifically, to a solution of a compound of Formula 705 in a nonpolar, aprotic solvent such as dichloromethane is added an excess, such as about two equivalents of an amine base, such as triethylamine, followed by about an equivalent of an acid chloride of formula $R_{14}COCl$. The resultant solution is stirred at ambient temperature for 2 hours, then evaporated under reduced pressure. The resultant solid is treated with glacial acetic acid, then the resultant suspension is heated at reflux for about 48 hours. The reaction is cooled to ambient temperature then evaporated under reduced pressure. The corresponding compound of Formula 709 is isolated and purified.

Reaction Scheme 9

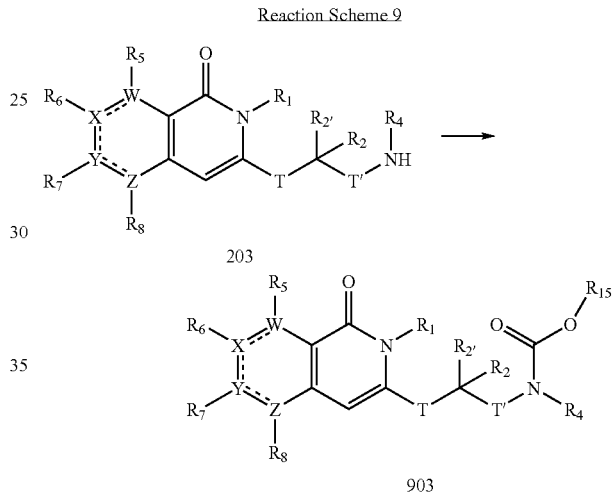

Referring to Reaction Scheme 9, a compound of Formula 203 is reacted with a slight excess of a compound of the formula $R_{15}O(CO)Cl$ in the presence of a base such as triethylamine in a nonpolar, aprotic solvent such as dichloromethane. The product, a compound of Formula 903 is isolated and purified.

Reaction Scheme 10

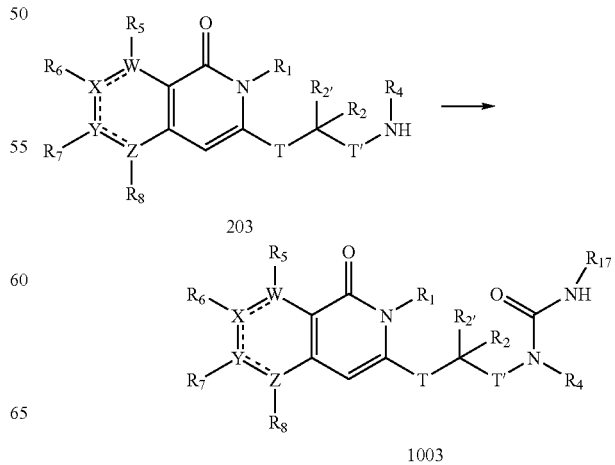

Referring to Reaction Scheme 10, a compound of Formula 203 is treated with a slight excess of an isocyanate $R_{17}$—N=C=O in the presence of a base, such as triethylamine, in a nonpolar, aprotic solvent, such as dichloromethane. The product, a compound of Formula 1003, is isolated and purified.

Reaction Scheme 11

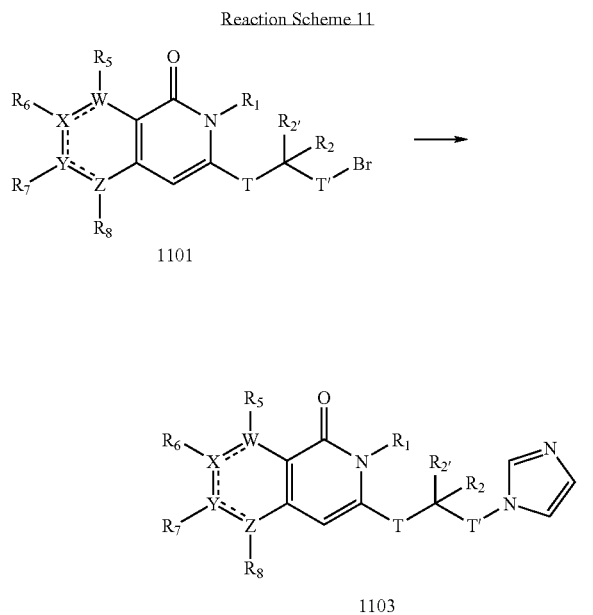

1101

1103

Preparation of Compounds of Formula 1103

Referring to Reaction Scheme 11, to a solution of a compound of Formula 1101 in a nonpolar, aprotic solvent such as DMF are added a base such as triethylamine and an excess (such as about 1.5 equivalents) of imidazole followed by about an equivalent of tetrabutylammonium iodide. The resultant solution is heated to about 90° C., stirred for about 18 h and allowed to cool to room temperature. The product, a compound of Formula 1103, is isolated and purified.

Reaction Scheme 12

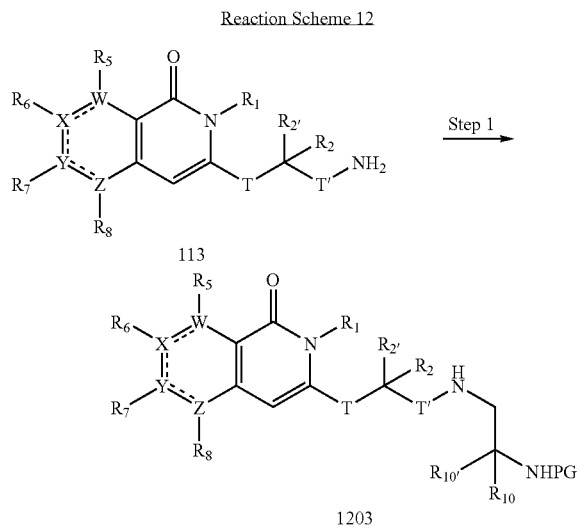

113

1203

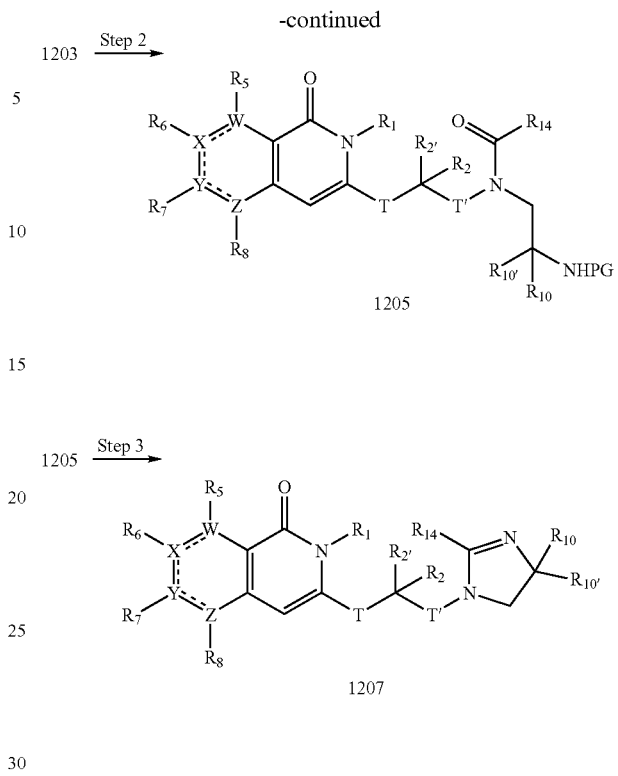

1205

1207

Preparation of Compounds of Formula 1203

Referring to Reaction Scheme 12, Step 1, to a solution of a compound of Formula 113 and an excess of an optionally substituted, aldehyde-containing carbamic acid ester in a nonpolar, aprotic solvent such as $CH_2Cl_2$ is added sodium triacetoxyborohydride. The mixture is stirred overnight. The product, a compound of Formula 1203, is isolated and purified.

Preparation of Compounds of Formula 1207

Referring to Reaction Scheme 12, Step 2, to a solution of a compound of Formula 1203 in a nonpolar, aprotic solvent such as toluene is added a base such as triethylamine followed by dropwise addition of an excess of an acid chloride of the formula $R_{14}$—COCl. The reaction mixture is heated to about 80° C. for about 18 h, then at reflux for about 4 h. The product, a compound of Formula 1207, is isolated and purified.

Alternative Preparation of Compounds of Formula 1207

Referring to Reaction Scheme 12, Step 3, in some embodiments, protecting group, PG, must be removed separately prior to cyclization to form the imidazolinyl compound. For example, when PG is Boc, a solution of a compound of Formula 1205 in a solvent such as $CH_2Cl_2$/TFA (such as about 4:1 $CH_2Cl_2$/TFA) is stirred at room temperature. The reaction mixture is concentrated under reduced pressure and the residue is diluted with a nonpolar, aprotic solvent such as $CH_2Cl_2$ and washed with aqueous base. The aqueous layer is extracted with a nonpolar, aprotic solvent such as $CH_2Cl_2$ and the combined extracts are dried, filtered and concentrated under reduced pressure. The residue is diluted with a nonpolar, aprotic solvent such as THF and aqueous base (such as saturated aqueous $NaHCO_3$). The mixture is stirred at room temperature for 10 days. The product, a compound of Formula 1207, is isolated and purified.

Reaction Scheme 13

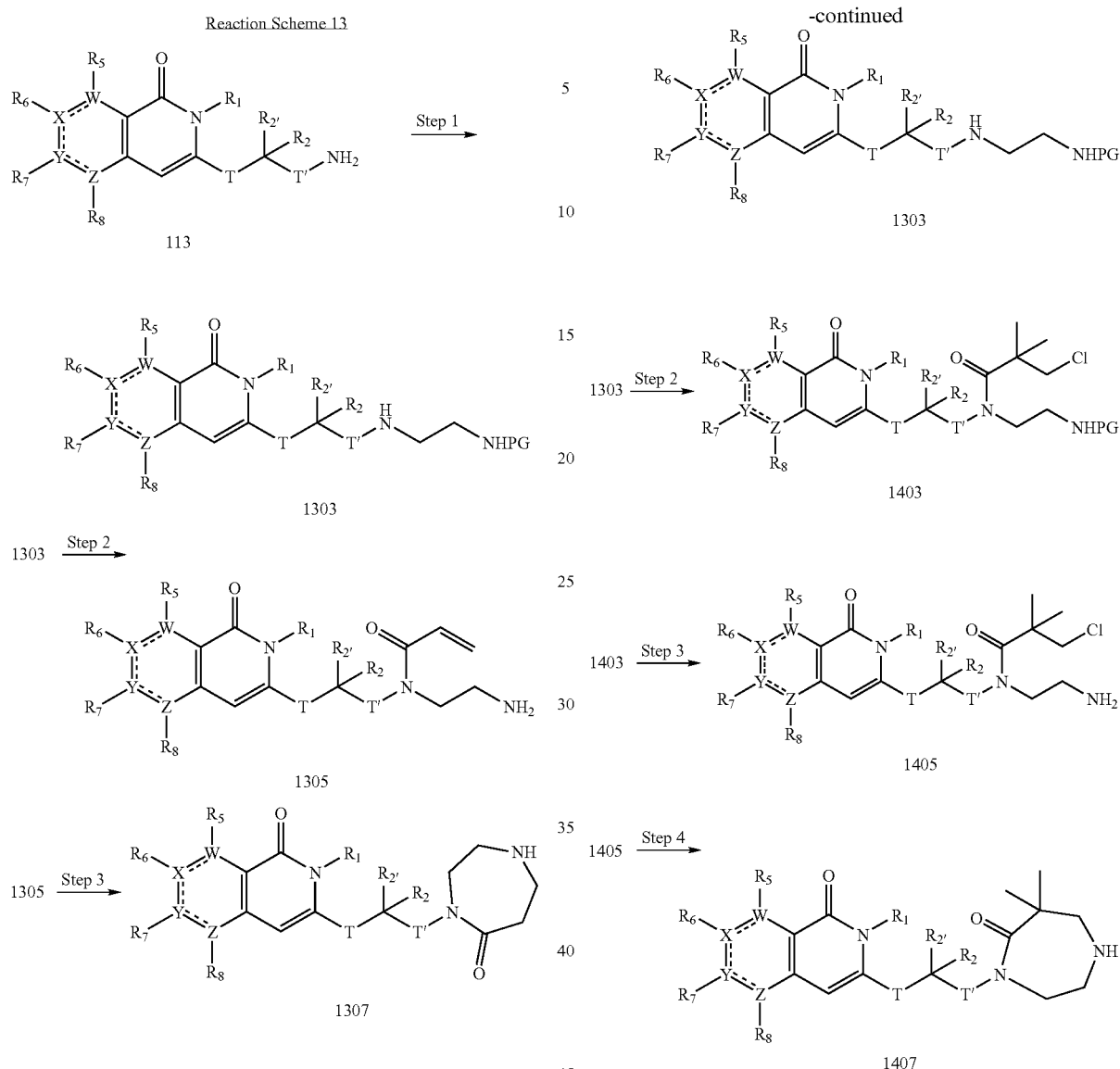

Referring to Reaction Scheme 13, reductive amination of the primary amino group in compounds of Formula 113 with (2-oxo-ethyl)-carbamic acid tert-butyl ester gives the corresponding secondary amine. Acylation with acryloyl chloride followed by deprotection of the tertiary amide and base mediated cyclisation gives the desired diazepanones. If desired, further functionalization of the basic amine can be accomplished under conditions well known to those skilled in the art.

Referring to Reaction Scheme 14, reductive amination of the primary amino group in compounds of Formula 113 with (2-oxo-ethyl)-carbamic acid tert-butyl ester gives the corresponding secondary amine. Acylation with chloropivaloyl chloride followed by deprotection of the tertiary amide and base mediated cyclisation gives the desired diazepanones. If desired, further functionalization of the basic amine can be accomplished under conditions well known to those skilled in the art.

Reaction Scheme 14

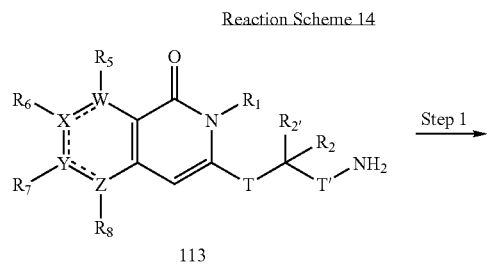

Reaction Scheme 15

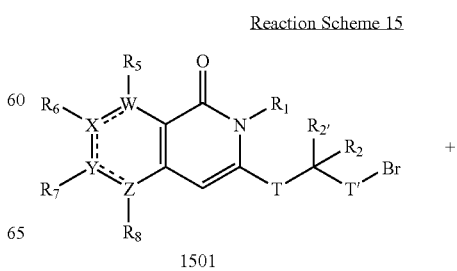

-continued

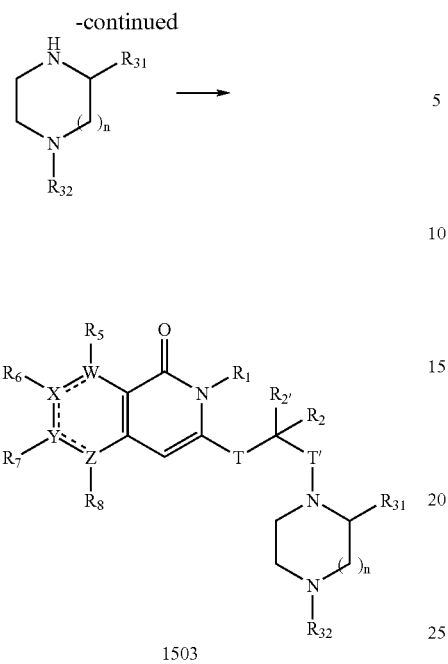

1503

Referring to Reaction Scheme 15, a compound of Formula 1501, one-half molar equivalent of an optionally substituted piperazine or diazepam (as shown above, where $R_{32}$ is as described herein) and an excess of potassium carbonate are combined in an organic solvent (e.g., acetonitrile). The reaction takes place under a nitrogen atmosphere at elevated temperature (e.g., 100° C.) over a period of 8 hours, followed at a somewhat lower temperature (e.g., 60° C.) for a period of 5 days. The product, a compound of Formula 1503, is isolated and purified.

Optionally, in the event that $R_{32}$ is an amine protecting group, such as Boc, it may be removed by for example treatment with a 95/5 mixture of TFA/water followed by stirring at room temperature for 1 hour. The product, a compound of Formula 1803 wherein $R_{32}$ is hydrogen, can be isolated and purified. If desired, further functionalization of the basic amine could be accomplished under conditions well known to those skilled in the art.

Reaction Scheme 16

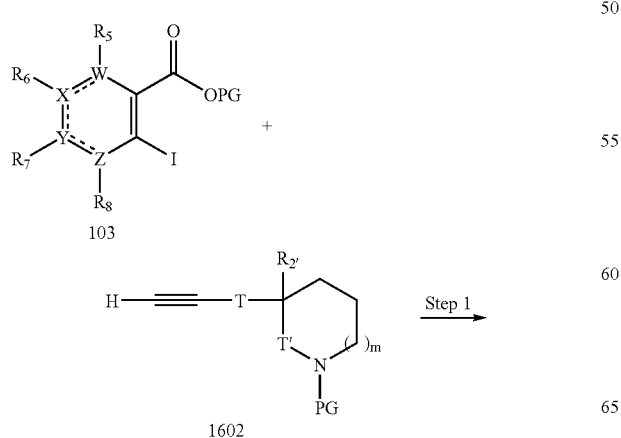

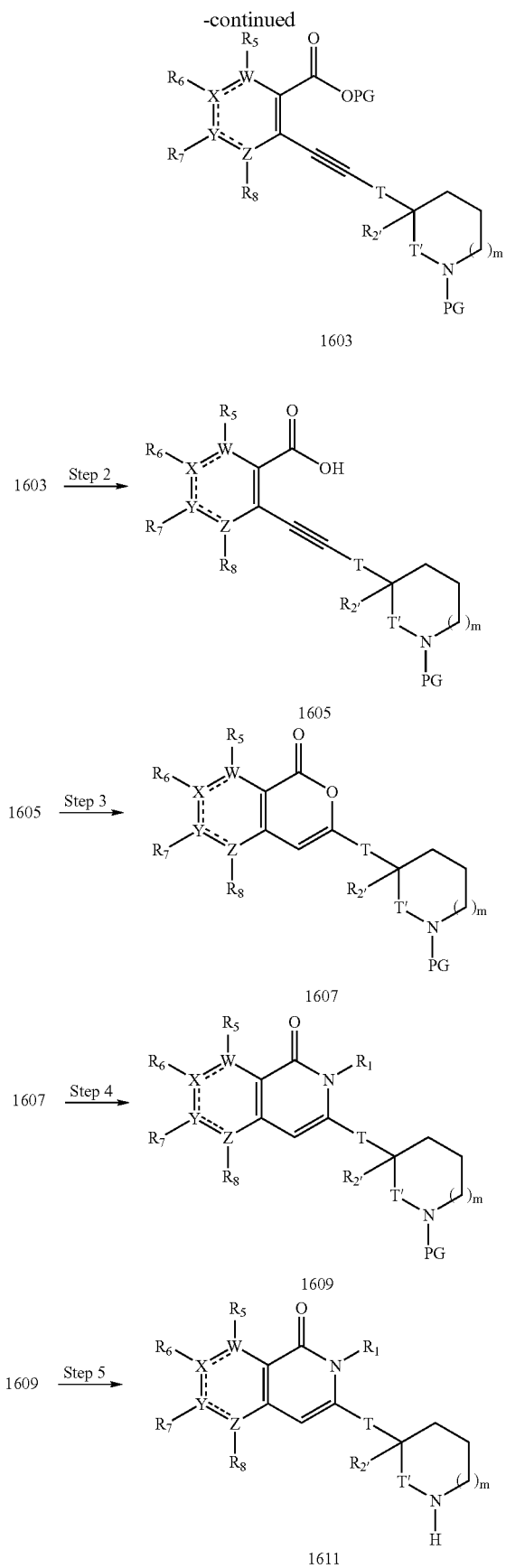

The synthesis of compounds of Formula I, II, or III wherein $R_4$ taken together with $R_2$ form an optionally substituted 5- to 12-membered nitrogen-containing heterocycle can be accomplished according to the general procedure shown in Scheme 16 and as described further in Reaction Scheme 1 above.

A compound of Formula 203:

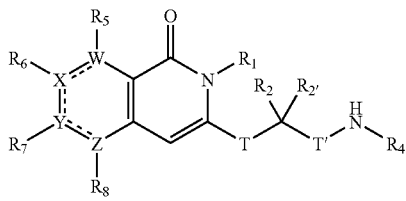

(where $R_4$ is optionally protected) is contacted with a slight molar excess of an $R_3$ chloride [such as, Cl—C(O)—$R_3$, Cl—S(O)$_2$—$R_{3a}$, Cl—$R_3$, Cl—C(O)—O—$R_{15}$ and Cl—S(O)$_2$—NH—$R_{3a}$] or an isocyanate (such as O=C=N—$R_{17}$) or an anhydride (such as O[C(O)$R_{15}$]$_2$ or O[S(O)$_2R_{3a}$]$_2$) to give the corresponding optionally protected compound of Formula I, II, or III.

A compound of Formula 505, 605, 705, or 707 is optionally cyclized by acid-mediated cyclization.

A racemic mixture of isomers of a compound of Formula I, II, or III is optionally placed on a chromatography column and separated into (R)— and (S)— enantiomers.

A compound of Formula I, II, or III is optionally contacted with a pharmaceutically acceptable acid or base to form the corresponding acid or base addition salt.

A pharmaceutically acceptable acid addition salt of a compound of Formula I, II, or III is optionally contacted with a base to form the corresponding free base of Formula I, II, or III.

A pharmaceutically acceptable base addition salt of a compound of Formula I, II, or III is optionally contacted with an acid to form the corresponding free acid of Formula I, II, or III.

T and T'

When considering the compounds of Formula I or II, in some embodiments, T is optionally substituted alkylene or is absent (i.e., is a covalent bond); and T' is optionally substituted alkylene or is absent (i.e., is a covalent bond). In some embodiments, one of T and T' is absent and the other is optionally substituted alkylene (such as optionally substituted methylene). In some embodiments, both are absent. In some embodiments both are optionally substituted alkylene.

$R_1$

When considering the compounds of Formula I, II, or III, in some embodiments $R_1$ is selected from hydrogen, optionally substituted $C_1$-$C_8$ alkyl, optionally substituted aryl, optionally substituted heteroaryl, optionally substituted aryl-$C_1$-$C_4$-alkyl-, and optionally substituted heteroaryl-$C_1$-$C_4$-alkyl- (such as optionally substituted aryl and optionally substituted aryl-$C_1$-$C_4$-alkyl-). In some embodiments, $R_1$ is selected from hydrogen, optionally substituted $C_1$-$C_4$ alkyl, optionally substituted phenyl-$C_1$-$C_4$-alkyl-, optionally substituted heteroaryl-$C_1$-$C_4$-alkyl-, optionally substituted naphthalenylmethyl, optionally substituted phenyl, and naphthyl. In some embodiments, $R_1$ is optionally substituted phenyl-$C_1$-$C_4$-alkyl-, optionally substituted heteroaryl-$C_1$-$C_4$-alkyl-, optionally substituted naphthalenylmethyl, optionally substituted phenyl, or naphthyl (such as optionally substituted phenyl-$C_1$-$C_4$-alkyl-, optionally substituted heteroaryl-$C_1$-$C_4$-alkyl-).

In some embodiments, $R_1$ is naphthyl, phenyl, bromophenyl, chlorophenyl, methoxyphenyl, ethoxyphenyl, tolyl, dimethylphenyl, chorofluorophenyl, methylchlorophenyl, ethylphenyl, phenethyl, benzyl, halobenzyl (such as chlorobenzyl or bromobenzyl), methylbenzyl, methoxybenzyl, cyanobenzyl, hydroxybenzyl, dichlorobenzyl, dimethoxybenzyl, or naphthalenylmethyl. In some embodiments, $R_1$ is benzyl, halobenzyl, methylbenzyl, hydroxybenzyl, cyanobenzyl, methoxybenzyl, or naphthalenylmethyl. In some embodiments, $R_1$ is benzyl.

$R_2$ and $R_{2'}$

When considering the compounds of Formula I, II, or III and as will be appreciated by those skilled in the art, the compounds described herein possess a potentially chiral center at the carbon to which $R_2$ and $R_{2'}$ are attached. The $R_2$ and $R_{2'}$ groups may be the same or different; if different, the compound is chiral (i.e., has a stereogenic center). When $R_2$ and $R_{2'}$ are different, in some embodiments $R_{2'}$ is hydrogen and $R_2$ is other than hydrogen. The invention contemplates the use of pure enantiomers and mixtures of enantiomers, including racemic mixtures. The term "substantially pure" means having at least about 95% chemical purity with no single impurity greater than about 1%. The term "substantially optically pure" or "enantiomerically pure" means having at least about 97.5% enantiomeric excess. In some embodiments, the stereogenic center to which $R_2$ and $R_{2'}$ are attached is of the R configuration.

When considering the compounds of Formula I, in some embodiments $R_2$ and $R_{2'}$ are independently chosen from hydrogen, optionally substituted alkyl-, optionally substituted alkoxy, optionally substituted aryl-, optionally substituted aralkyl-, optionally substituted heteroaryl-, and optionally substituted heteroaralkyl-; or $R_2$ and $R_{2'}$ taken together form an optionally substituted 3- to 7-membered ring.

In some embodiments, $R_2$ is optionally substituted $C_1$-$C_4$ alkyl-, and $R_{2'}$ is hydrogen or optionally substituted $C_1$-$C_4$ alkyl-. In some embodiments, $R_{2'}$ is hydrogen and $R_2$ is optionally substituted $C_1$-$C_4$ alkyl-. In some embodiments, $R_2$ is chosen from methyl-, ethyl-, propyl (such as c-propyl or i-propyl), butyl (such as t-butyl), methylthioethyl-, methylthiomethyl-, aminobutyl-, (CBZ)aminobutyl-, cyclohexylmethyl-, benzyloxymethyl-, methylsulfanylethyl-, methylsulfanylmethyl-, and hydroxymethyl-, and $R_{2'}$ is hydrogen. In some embodiments, $R_{2'}$ is hydrogen and $R_2$ is ethyl or propyl (such as c-propyl or i-propyl). In some embodiments, $R_2$ is i-propyl. In some embodiments, the stereogenic center to which $R_2$ and $R_{2'}$ is attached is of the R configuration.

In some embodiments, if either $R_2$ or $R_{2'}$ is hydrogen, then the other is not hydrogen. In some embodiments, both $R_2$ and $R_{2'}$ are hydrogen.

$R_2$ Taken Together with $R_4$

When considering the compounds of Formula I, II, or III, in some embodiments, $R_2$ and $R_4$ taken together form a 5- to 12-membered ring which optionally incorporates one or two additional heteroatoms, selected from N, O, and S in the heterocycle ring and may optionally be substituted with one or more of the following groups: alkyl, aryl, aralkyl, heteroaryl, substituted alkyl, substituted aryl, substituted aralkyl, and substituted heteroaryl, hydroxyl, alkoxy, cyano, optionally substituted amino, oxo, or carbamyl.

In some embodiments of compounds of Formula I or II, $R_2$ and $R_4$ taken together form an optionally substituted ring of the formula:

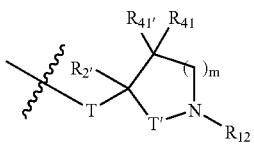

wherein $R_{41}$ and $R_{41'}$ are independently chosen from hydrogen, alkyl, aryl, aralkyl, heteroaryl, substituted alkyl, substituted aryl, substituted aralkyl, and substituted heteroaryl; m is 0, 1, 2, or 3; and T, T', $R_{12}$, and $R_{2'}$ are as defined above. In some embodiments, $R_{41}$ is hydrogen. In some embodiments, both $R_{41}$ and $R_{41'}$ are hydrogen. In some embodiments, $R_{12}$ is optionally substituted aralkyl (such as benzyl) or optionally substituted acyl (i.e., $R_{12}$ is —(CO)$R_3$ where $R_3$ is as defined above, for example, $R_3$ is optionally substituted phenyl). See, e.g., PCT/US03/030788, which is incorporated herein by reference for all purposes.

In some embodiments of compounds of Formula III, $R_2$ and $R_4$ taken together form an optionally substituted ring of the formula:

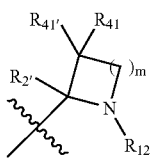

wherein $R_{41}$ and $R_{41'}$ are independently chosen from hydrogen, alkyl, aryl, aralkyl, heteroaryl, substituted alkyl, substituted aryl, substituted aralkyl, and substituted heteroaryl; m is 1, 2, or 3; and $R_{12}$ and $R_{2'}$ are as defined above. In some embodiments, $R_{41}$ is hydrogen. In some embodiments, both $R_{41}$ and $R_{41'}$ are hydrogen. In some embodiments, $R_{12}$ is optionally substituted aralkyl (such as benzyl) or optionally substituted acyl (i.e., $R_{12}$ is —(CO)$R_3$ where $R_3$ is as defined above, for example, $R_3$ is optionally substituted phenyl). See, e.g., U.S. Ser. No. PCT/US03/030788, which is incorporated herein by reference for all purposes.

In some embodiments of compounds of Formula I or II, $R_2$ and $R_4$ taken together form an optionally substituted ring of the formula:

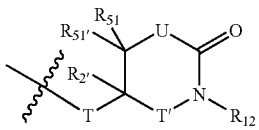

wherein $R_{12}$, $R_{2'}$, T, and T' are as defined above; $R_{51}$ and $R_{51'}$ are independently chosen from hydrogen, alkyl, aryl, aralkyl, heteroaryl, substituted alkyl, substituted aryl, substituted aralkyl and substituted heteroaryl; U is a covalent bond, CR'R" or NR'''; R' and R" are independently chosen from hydrogen, hydroxy, amino, optionally substituted aryl, optionally substituted alkylamino, optionally substituted alkyl and optionally substituted alkoxy; and R''' is chosen from hydrogen, optionally substituted alkyl, optionally substituted aryl, optionally substituted aralkyl, optionally substituted heteroaryl, and optionally substituted heteroaralkyl. In some embodiments, $R_{51}$ is hydrogen or optionally substituted lower alkyl. In some embodiments, $R_{51}$ is hydrogen. In some embodiments, $R_{51'}$ is hydrogen or optionally substituted lower alkyl. In some embodiments, $R_{51'}$ is hydrogen. In some embodiments, $R_{12}$ is optionally substituted aryl or optionally substituted aralkyl. In some embodiments, $R_{12}$ is optionally substituted phenyl, benzyl or methyl-benzyl (such as benzyl or methyl-benzyl).

In some embodiments, U is CR'R" where R' and/or R" are hydrogen. In some embodiments, U is NR''' where R''' is hydrogen or optionally substituted alkyl. In some embodiments, R''' is hydrogen or optionally substituted amino-lower alkyl. See, e.g., PCT/US03/23319, which is incorporated herein by reference for all purposes.

In some embodiments of compounds of Formula III, $R_2$ and $R_4$ taken together form an optionally substituted ring of the formula:

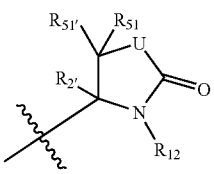

wherein $R_{12}$ and $R_{2'}$ are as defined above; $R_{51}$ and $R_{51'}$ are independently chosen from hydrogen, alkyl, aryl, aralkyl, heteroaryl, substituted alkyl, substituted aryl, substituted aralkyl and substituted heteroaryl; U is a covalent bond, CR'R" or NR'''; R' and R" are independently chosen from hydrogen, hydroxy, amino, optionally substituted aryl, optionally substituted alkylamino, optionally substituted alkyl and optionally substituted alkoxy; and R''' is chosen from hydrogen, optionally substituted alkyl, optionally substituted aryl, optionally substituted aralkyl, optionally substituted heteroaryl, and optionally substituted heteroaralkyl. In some embodiments, $R_{51}$ is hydrogen or optionally substituted lower alkyl. In some embodiments, $R_{51}$ is hydrogen. In some embodiments, $R_{51'}$ is hydrogen or optionally substituted lower alkyl. In some embodiments, $R_{51'}$ is hydrogen. In some embodiments, $R_{12}$ is optionally substituted aryl or optionally substituted aralkyl. In some embodiments, $R_{12}$ is optionally substituted phenyl, benzyl or methyl-benzyl (such as benzyl or methyl-benzyl). In some embodiments, U is CR'R" where R' and/or R" are hydrogen. In some embodiments, U is NR''' where R''' is hydrogen or optionally substituted alkyl. In some embodiments, R''' is hydrogen or optionally substituted amino-lower alkyl. See, e.g., PCT/US03/23319, which is incorporated herein by reference for all purposes.

$R_5$, $R_6$, $R_7$, $R_8$, and $R_{18}$

When considering the compounds of Formula I, II, and III, in some embodiments, $R_5$, $R_6$, $R_7$, $R_8$ and $R_{18}$ are independently chosen from hydrogen, acyl, optionally substituted alkyl-, optionally substituted alkoxy, halogen, hydroxyl, nitro, cyano, optionally substituted amino, alkylsulfonyl-, alkylsulfonamido-, alkylthio-, carboxyalkyl-, carboxamido-, aminocarbonyl-, optionally substituted aryl and optionally substituted heteroaryl-, provided that $R_5$, $R_6$, $R_7$ and $R_8$ is absent where W, X, Y, or Z, respectively, is —N═, O, S or absent. In some embodiments, when present, $R_5$, $R_6$, $R_7$, $R_8$ and $R_{18}$ are independently chosen from hydrogen, hydroxyl, halogen (such as chloro and fluoro), optionally substituted $C_1$-$C_4$ alkyl- (such as methyl-), $C_1$-$C_4$ alkoxy (such as methoxy), cyano, amino, substituted amino, or carbamyl-.

In some embodiments, $R_5$, $R_6$, $R_7$, $R_8$ and $R_{18}$ are methoxy, methyl, trifluoromethyl, cyano, hydrogen or halo. In some embodiments, $R_5$ is hydrogen or halo; $R_6$ is hydrogen, optionally substituted $C_1$-$C_4$ alkyl- (such as methyl-) or halo; $R_7$ is hydrogen, halo, optionally substituted $C_1$-$C_4$ alkyl- (such as methyl- or trifluoromethyl-), $C_1$-$C_4$ alkoxy (such as methoxy), cyano, substituted amino, or carbamyl-; and $R_8$ is hydrogen, $C_1$-$C_4$ alkyl- (such as methyl-), $C_1$-$C_4$ alkoxy (such as methoxy), hydroxy, or halo. In some embodiments, only one of $R_5$, $R_6$, $R_7$, and $R_8$ is not hydrogen, such as $R_7$. In some embodiments, $R_7$ and $R_8$ are not hydrogen. In some embodiments, $R_{18}$ is hydrogen.

$R_4$ Taken Together with $R_{12}$

When considering the compounds of Formula I, II, or III, in some embodiments, $R_4$ taken together with $R_{12}$, and the nitrogen to which they are bound, form an optionally substituted 5- to 12-membered nitrogen-containing heterocycle, which optionally incorporates one or two additional heteroatoms, selected from N, O, and S in the heterocycle ring and may optionally be substituted with one or more of the following groups: alkyl, aryl, aralkyl, heteroaryl, substituted alkyl, substituted aryl, substituted aralkyl, and substituted heteroaryl, hydroxyl, alkoxy, cyano, optionally substituted amino, oxo, or carbamyl.

When considering the compounds of Formula I and in some embodiments of compounds of Formula II when T and T' are not both absent, $R_4$ taken together with $R_{12}$ and the nitrogen to which they are bound, forms an optionally substituted imidazolyl ring of the formula:

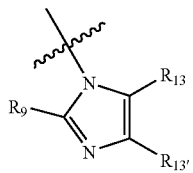

wherein $R_9$ is chosen from hydrogen, optionally substituted $C_1$-$C_8$ alkyl-, optionally substituted aryl-, optionally substituted aryl-$C_1$-$C_4$-alkyl-, optionally substituted heteroaryl-$C_1$-$C_4$-alkyl-, optionally substituted aryl-$C_1$-$C_4$-alkoxy, optionally substituted heteroaryl-$C_1$-$C_4$-alkoxy, and optionally substituted heteroaryl-; and $R_{13}$ and $R_{13'}$ are independently hydrogen, optionally substituted $C_1$-$C_8$ alkyl-, optionally substituted aryl-, or optionally substituted aryl-$C_1$-$C_4$-alkyl-. See, e.g., PCT/US03/14787, which is incorporated herein by reference.

In some embodiments, $R_9$ is phenyl substituted with $C_1$-$C_4$-alkyl-, $C_1$-$C_4$-alkoxy-, and/or halo; phenyl-; benzyl-; thienyl-; or thienyl- substituted with $C_1$-$C_4$-alkyl-, $C_1$-$C_4$-alkoxy-, and/or halo. In some embodiments, $R_9$ is phenyl substituted with one or more halo and/or methyl.

In some embodiments, $R_{13}$ is hydrogen and $R_{13'}$ is substituted $C_1$-$C_4$ alkyl-. In some embodiments, $R_{13}$ is hydrogen and $R_{13'}$ is aminomethyl-, aminoethyl-, aminopropyl-, acetylamino-methyl-, acetylaminoethyl-, benzyloxycarbonylamino-methyl- or benzyloxycarbonylamino-ethyl-.

When considering the compounds of Formula I and in some embodiments of compounds of Formula II when T and T' are not both absent, $R_4$ taken together with $R_{12}$ forms an optionally substituted imidazolinyl ring of the formula:

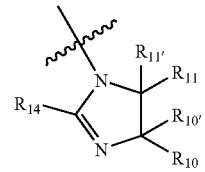

wherein, $R_{14}$ is chosen from hydrogen, optionally substituted $C_1$-$C_8$ alkyl-, optionally substituted aryl-, optionally substituted aryl-$C_1$-$C_4$-alkyl-, optionally substituted heteroaryl-, optionally substituted heteroaryl-$C_1$-$C_4$-alkyl-; and $R_{10}$, $R_{10'}$, $R_{11}$, and $R_{11'}$ are independently chosen from hydrogen, optionally substituted $C_1$-$C_8$ alkyl-, optionally substituted aryl-, and optionally substituted aryl-$C_1$-$C_4$-alkyl-.

In some embodiments, $R_{14}$ is methylenedioxyphenyl-; phenyl-; phenyl substituted with $C_1$-$C_4$ alkyl-, $C_1$-$C_4$ alkoxy-, and/or halo; benzyl-; thienyl substituted with $C_1$-$C_4$ alkyl; benzyl; thiophenyl-; or thiophenyl-substituted with $C_1$-$C_4$-alkyl-, $C_1$-$C_4$-alkoxy-, and/or halo. In some embodiments, $R_{14}$ is methylenedioxyphenyl-; phenyl-; tolyl-; methoxyphenyl-; or halomethylphenyl-.

In some embodiments, $R_{10}$, $R_{10'}$, $R_{11'}$, and $R_{11}$ are independently hydrogen or optionally substituted $C_1$-$C_4$ alkyl-. In some embodiments, $R_{11'}$ and $R_{11}$ are hydrogen.

When considering the compounds of Formula I, II, or III, in some embodiments, $R_4$ taken together with $R_{12}$ forms an optionally substituted diazepinone ring of the formula:

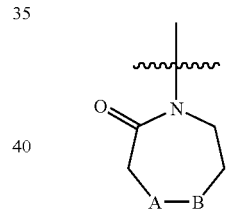

wherein A and B are each independently chosen from $C(R_{20})(R_{21})$, $N(R_{22})$, O or S, wherein $R_{20}$ and $R_{21}$ are each independently selected from H, optionally substituted alkyl optionally substituted aryl and optionally substituted heteroaryl; and $R_{22}$ is H, optionally substituted alkyl, optionally substituted aralkyl, optionally substituted heteroaralkyl, optionally substituted alkylcarbonyl, optionally substituted arylcarbonyl, optionally substituted heteroarylcarbonyl, optionally substituted aralkylcarbonyl, optionally substituted heteroaralkylcarbonyl, optionally substituted alkoxycarbonyl, optionally substituted aryloxycarbonyl, optionally substituted heteroaryloxycarbonyl, optionally substituted aralkyloxycarbonyl, optionally substituted heteroaralkyloxycarbonyl. In some embodiments, the diazepinone ring is further substituted with one or more of the following groups: optionally substituted alkyl, optionally substituted aryl, optionally substituted aralkyl, optionally substituted heteroaryl, and optionally substituted heteroaralkyl.

In some embodiments of the compounds of Formula I, II, or III, one of A or B is $C(R_{20})(R_{21})$, wherein $R_{20}$ and $R_{21}$ are each independently selected from H or $C_1$-$C_4$ alkyl, and the other of A or B is $N(R_{22})$, where $R_{22}$ is H, $C_1$-$C_4$ alkyl, optionally substituted aralkyl, optionally substituted heteroaralkyl, $C_1$-$C_6$ alkylcarbonyl, optionally substituted arylcarbonyl, optionally substituted heteroarylcarbonyl, optionally substituted aralkylcarbonyl, optionally substituted heteroaralkylcarbonyl, $C_1$-$C_6$ alkoxycarbonyl, optionally substituted aryloxycarbonyl, optionally substituted heteroaryloxycarbonyl, optionally substituted aralkyloxycarbonyl, optionally substituted heteroaralkyloxycarbonyl, where the optionally substituted aryl or heteroaryl groups or moieties are unsubstituted or substituted with one or more substituents selected from $C_1$-$C_4$ alkyl, $C_1$-$C_4$ haloalkyl, $C_1$-$C_4$ alkoxy, $C_1$-$C_4$ haloalkoxy, amino, $C_1$-$C_4$ alkylamino, di-$C_1$-$C_4$ alkylamino, carboxy, $C_1$-$C_4$ alkylcarbonyloxy, $C_1$-$C_4$ alkoxycarbonyl, carboxamido, $C_1$-$C_4$ alkylcarboxamido, aminocarbonyl, $C_1$-$C_4$ alkylaminocarbonyl, di-$C_1$-$C_4$ alkylaminocarbonyl, cyano, $C_1$-$C_4$ alkylcarbonyl, halogen, hydroxyl, mercapto and nitro. In some embodiments, A is $C(R_{20})(R_{21})$, wherein $R_{20}$ and $R_{21}$ are each H or $C_1$-$C_4$ alkyl, and B is $N(R_{22})$, where $R_{22}$ is H, $C_1$-$C_4$ alkyl, aralkyl, heteroaralkyl, $C_1$-$C_6$ alkylcarbonyl, arylcarbonyl, heteroarylcarbonyl. In some embodiments of the compounds of Formula I, A is $CH_2$, and B is $N(R_{22})$, where $R_{22}$ is H, methyl, benzyl or acetyl (—C(O)methyl). See, e.g., U.S. Ser. No. 60/435,001, which is incorporated herein by reference for all purposes.

In some embodiments of compounds of Formula I, II, or III, $R_4$ taken together with $R_{12}$ forms an optionally substituted piperazine- or diazepam of the formula:

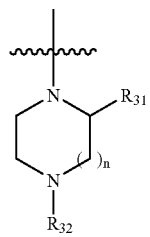

$R_{31}$ and $R_{32}$ are independently chosen from hydrogen, optionally substituted alkyl, optionally substituted aryl, optionally substituted heteroaryl, optionally substituted aralkyl, and optionally substituted heteroaralkyl; and n is 1 or 2. In some embodiments, $R_{31}$ is aryl (such as phenyl), substituted aryl (such as lower alkyl-, lower alkoxy-, and/or halo-substituted phenyl), aralkyl (such as benzyl and phenylvinyl), heteroaralkyl, substituted aralkyl (such as substituted benzyl and substituted phenylvinyl), or substituted heteroaralkyl; $R_{32}$ is hydrogen; and n is 1. See, e.g., PCT/US03/026093, which is incorporated herein by reference.

$R_4$

When considering compounds of Formula I, in some embodiments, $R_4$ is chosen from hydrogen, optionally substituted $C_1$-$C_{13}$ alkyl, optionally substituted aryl, optionally substituted aryl-$C_1$-$C_4$-alkyl-, optionally substituted heterocyclyl, and optionally substituted heteroaryl-$C_1$-$C_4$-alkyl- (such as hydrogen or optionally substituted $C_1$-$C_{13}$ alkyl).

In some embodiments, $R_4$ is chosen from hydrogen, $C_1$-$C_4$ alkyl; cyclohexyl; phenyl substituted with hydroxyl, $C_1$-$C_4$ alkoxy or $C_1$-$C_4$ alkyl; benzyl; and $R_{16}$-alkylene-, wherein $R_{16}$ is hydroxyl, carboxy, ($C_1$-$C_4$ alkoxy)carbonyl-, di($C_1$-$C_4$ alkyl)amino-, ($C_1$-$C_4$ alkyl)amino-, amino, ($C_1$-$C_4$ alkoxy) carbonylamino-, $C_1$-$C_4$ alkoxy-, or optionally substituted N-heterocyclyl- (such as azetidinyl, morpholinyl, pyridinyl, indolyl, furanyl, pyrrolidinyl, piperidinyl or imidazolyl, each of which may be optionally substituted).

In some embodiments, $R_4$ is chosen from hydrogen, methyl, ethyl, propyl, butyl, cyclohexyl, carboxyethyl, carboxymethyl, methoxyethyl, hydroxyethyl, hydroxypropyl, dimethylaminoethyl, dimethylaminopropyl, diethylaminoethyl, diethylaminopropyl, aminopropyl, methylaminopropyl, 2,2-dimethyl-3-(dimethylamino)propyl, aminoethyl, aminobutyl, aminopentyl, aminohexyl, isopropylaminopropyl, diisopropylaminoethyl, 1-methyl-4-(diethylamino)butyl, (t-Boc)aminopropyl, hydroxyphenyl, benzyl, methoxyphenyl, methylmethoxyphenyl, dimethylphenyl, tolyl, ethylphenyl, (oxopyrrolidinyl)propyl, (methoxycarbonyl)ethyl, benzylpiperidinyl, pyridinylethyl, pyridinylmethyl, morpholinylethyl morpholinylpropyl, piperidinyl, azetidinylmethyl, azetidinylethyl, azetidinylpropyl pyrrolidinylethyl, pyrrolidinylpropyl, piperidinylmethyl, piperidinylethyl, imidazolylpropyl, imidazolylethyl, (ethylpyrrolidinyl) methyl, (methylpyrrolidinyl)ethyl, (methylpiperidinyl) propyl, (methylpiperazinyl)propyl, furanylmethyl and indolylethyl.

In some embodiments, $R_4$ is $R_{16}$-alkylene-, wherein $R_{16}$ is amino, $C_1$-$C_4$ alkylamino-, di($C_1$-$C_4$ alkyl)amino-, $C_1$-$C_4$ alkoxy-, hydroxyl, or N-heterocyclyl. In some embodiments, $R_{16}$ is amino. In some embodiments, the alkylene moiety of $R_{16}$-alkylene- has from 1 to 6 carbon atoms.

In some embodiments, $R_4$ is aminoethyl, aminopropyl, aminobutyl, aminopentyl, aminohexyl, methylaminoethyl, methylaminopropyl, methylaminobutyl, methylaminopentyl, methylaminohexyl, dimethylaminoethyl, dimethylaminopropyl, dimethylaminobutyl, dimethylaminopentyl, dimethylaminohexyl, ethylaminoethyl, ethylaminopropyl, ethylaminobutyl, ethylaminopentyl, ethylaminohexyl, diethylaminoethyl, diethylaminopropyl, diethylaminobutyyl, diethylaminopentyl, or diethylaminohexyl. In some embodiments, $R_4$ is aminopropyl.

$R_{12}$

When considering the compounds of Formula I, in some embodiments $R_{12}$ is chosen from hydrogen, optionally substituted alkyl-, optionally substituted aryl-, optionally substituted aralkyl-, optionally substituted heteroaryl-, optionally substituted heteroaralkyl-, —C(O)—$R_3$, and —S(O)$_2$-$R_{3a}$. In some embodiments, $R_{12}$ is optionally substituted $C_1$-$C_{13}$ alkyl (such as substituted $C_1$-$C_4$ alkyl); optionally substituted aralkyl (such as optionally substituted benzyl or naphthylmethyl-); and optionally substituted heteroaralkyl. In some embodiments, $R_{12}$ is benzyl or benzyl substituted with one or more of the following groups: carboxy, alkoxycarbonyl cyano, halo, $C_1$-$C_4$ alkyl-, $C_1$-$C_4$ alkoxy, nitro, methylenedioxy, or trifluoromethyl. In some embodiments, and as described below, $R_{12}$ is —C(O)$R_3$. In some embodiments, and as described below $R_{12}$ is —SO$_2$R$_{3a}$.

$R_{12}$ is —C(O)R$_3$

When considering the compounds of Formula I, in some embodiments when $R_{12}$ is —C(O)R$_3$, $R_3$ is selected from optionally substituted $C_1$-$C_8$ alkyl, optionally substituted aryl-$C_1$-$C_4$-alkyl-, optionally substituted heteroaryl-$C_1$-$C_4$-alkyl-, optionally substituted heteroaryl, optionally substituted aryl, $R_{15}$O— and $R_{17}$—NH—, $R_{15}$ is chosen from optionally substituted $C_1$-$C_8$ alkyl and optionally substituted aryl, and $R_{17}$ is chosen from hydrogen, optionally substituted $C_1$-$C_8$ alkyl and optionally substituted aryl.

In some embodiments, $R_3$ is chosen from optionally substituted $C_1$-$C_8$ alkyl, optionally substituted aryl-$C_1$-$C_4$-alkyl-, optionally substituted heteroaryl-$C_1$-$C_4$-alkyl-, optionally substituted heteroaryl, and optionally substituted aryl. In some embodiments, $R_3$ is chosen from phenyl;
phenyl substituted with one or more of the following substituents: halo; $C_1$-$C_4$ alkyl; $C_1$-$C_4$ alkyl substituted with hydroxy (e.g., hydroxymethyl); $C_1$-$C_4$ alkoxy; $C_1$-$C_4$ alkyl substituted with $C_1$-$C_4$ alkoxy, halo, nitro, formyl, carboxy, cyano, methylenedioxy, ethylenedioxy, acyl (e.g., acetyl), —N-acyl (e.g., N-acetyl) or trifluoromethyl;
benzyl;
phenoxymethyl-;
halophenoxymethyl-;
phenylvinyl-;
heteroaryl-;
heteroaryl- substituted with $C_1$-$C_4$ alkyl or $C_1$-$C_4$ alkyl substituted with halo (e.g., $CF_3$);
$C_1$-$C_4$ alkyl substituted with $C_1$-$C_4$ alkoxy-; and
benzyloxymethyl-.

In some embodiments, when $R_3$ is not $R_{17}NH$— or $R_{15}O$—, $R_3$ is chosen from phenyl, halophenyl, dihalophenyl, cyanophenyl, halo(trifluoromethyl)phenyl, hydroxymethylphenyl, methoxymethylphenyl, methoxyphenyl, ethoxyphenyl, carboxyphenyl, formylphenyl, ethylphenyl, tolyl, methylenedioxyphenyl, ethylenedioxyphenyl, methoxychlorophenyl, dihydro-benzodioxinyl, methylhalophenyl, trifluoromethylphenyl, furanyl, $C_1$-$C_4$ alkyl substituted furanyl, trifluoromethylfuranyl, $C_1$-$C_4$ alkyl substituted trifluoromethylfuranyl, benzofuranyl, thiophenyl, $C_1$-$C_4$ alkyl substituted thiophenyl, benzothiophenyl, benzothiadiazolyl, pyridinyl, indolyl, methylpyridinyl, trifluoromethylpyridinyl, pyrrolyl, quinolinyl, picolinyl, pyrazolyl, $C_1$-$C_4$ alkyl substituted pyrazolyl, N-methyl pyrazolyl, $C_1$-$C_4$ alkyl substituted N-methyl pyrazolyl, $C_1$-$C_4$ alkyl substituted pyrazinyl, $C_1$-$C_4$ alkyl substituted isoxazolyl, benzoisoxazolyl, morpholinomethyl, methylthiomethyl, methoxymethyl, N-methyl imidazolyl, and imidazolyl. In some embodiments, $R_3$ is optionally substituted phenyl (such as tolyl, halophenyl, methylhalophenyl, hydroxymethylphenyl, halo(trifluoromethyl)phenyl-, methylenedioxyphenyl, formylphenyl or cyanophenyl).

In some embodiments, when $R_3$ is $R_{17}NH$—, $R_{17}$ is chosen from hydrogen, $C_1$-$C_4$ alkyl; cyclohexyl; phenyl; and phenyl substituted with halo, $C_1$-$C_4$ alkyl, trifluoromethyl, $C_1$-$C_4$ alkoxy, or $C_1$-$C_4$ alkylthio.

In some embodiments, when $R_3$ is $R_{17}NH$—, $R_{17}$ is hydrogen isopropyl, butyl, cyclohexyl, phenyl, bromophenyl, dichlorophenyl, methoxyphenyl, ethylphenyl, tolyl, trifluoromethylphenyl or methylthiophenyl.

In some embodiments, wherein $R_3$ is $R_{15}O$—, $R_{15}$ is chosen from optionally substituted $C_1$-$C_8$ alkyl and optionally substituted aryl.

$R_{12}$ is —$SO_2R_{3a}$

When considering the compounds of Formula I, in some embodiments, when $R_{12}$ is —$SO_2R_{3a}$, $R_{3a}$ is chosen from $C_1$-$C_{13}$ alkyl-; phenyl; naphthyl; phenyl substituted with cyano, halo, lower-alkyl-, lower-alkoxy, nitro, methylenedioxy, or trifluoromethyl-; biphenylyl and heteroaryl-. In some embodiments, $R_{3a}$ is chosen from phenyl substituted with halo, lower-alkyl-, lower-alkoxy, cyano, nitro, methlenedioxy, or trifluoromethyl-; and naphthyl-.

Salt Forms

Compounds of the invention will generally be capable of forming acid addition salts (i.e., will comprise a site which reacts with a pharmaceutically acceptable acid to form an acid addition salt.) The present invention includes pharmaceutically acceptable acid addition salts of the compounds of Formula I. Acid addition salts of the present compounds are prepared in a standard manner in a suitable solvent from the parent compound and an excess of an acid, such as hydrochloric, hydrobromic, sulfuric, phosphoric, acetic, maleic, succinic or methanesulfonic.

The salts and/or solvates of the compounds of the Formula I which are not pharmaceutically acceptable may be useful as intermediates in the preparation of pharmaceutically acceptable salts and/or solvates of compounds of Formula I or the compounds of the Formula I themselves, and as such form another aspect of the present invention.

Compounds of Formula I

When considering the compounds of Formula I, in some embodiments, one of W, X, Y, and Z is N and the others are C;

$R_1$ is benzyl, halobenzyl, methoxybenzyl-, cyanobenzyl, or naphthalenylmethyl-; $R_2$ is optionally substituted $C_1$-$C_4$ alkyl;

$R_2$, is hydrogen;

$R_5$, $R_6$, $R_7$, and $R_8$ are independently chosen from hydrogen, amino, alkylamino, dialkylamino, hydroxyl, halogen (such as chloro and fluoro), $C_1$-$C_4$ alkyl (such as methyl), $C_1$-$C_4$ haloalkyl (such as trifluoromethyl), $C_1$-$C_4$ alkoxy (such as methoxy), $C_1$-$C_4$ haloalkoxy and cyano;

T and T' are independently a covalent bond or optionally substituted lower alkylene (such as where T and T' are both absent);

$R_{12}$ is —$C(O)R_3$ wherein $R_3$ is optionally substituted $C_1$-$C_8$ alkyl (e.g., $C_1$-$C_8$ alkyl substituted with lower-alkoxy), optionally substituted heteroaryl, and optionally substituted aryl (such as halophenyl, halomethylphenyl-, methylenedioxyphenyl-, methoxyphenyl-, ethoxyphenyl-, cyanophenyl- or phenyl substituted with lower-acyl or lower-alkylaminocarbonyl-, e.g. methylaminocarbonyl- or ethylaminocarbonyl-, or di(lower-alkyl)aminocarbonyl-, e.g. dimethylaminocarbonyl- or diethylaminocarbonyl- or lower alkyl); and $R_4$ is $R_{16}$-alkylene-, wherein $R_{16}$ is amino, $C_1$-$C_4$ alkylamino-, di($C_1$-$C_4$ alkyl)amino-, $C_1$-$C_4$ alkoxy-, hydroxyl, or N-heterocyclyl.

In some embodiments, $R_1$ is benzyl, halobenzyl, methoxybenzyl, cyanobenzyl, or naphthalenylmethyl; and $R_2$ is propyl (such as i- or c-propyl).

In some embodiments, one of W, X, Y, and Z is N and the others are C;

$R_1$ is benzyl, halobenzyl, methoxybenzyl, cyanobenzyl, or naphthalenylmethyl; $R_2$ is optionally substituted $C_1$-$C_4$ alkyl;

$R_2$, is hydrogen;

$R_5$, $R_6$, $R_7$, and $R_8$ are independently chosen from hydrogen, amino, alkylamino, dialkylamino, hydroxyl, halogen (such as chloro and fluoro), $C_1$-$C_4$ alkyl (such as methyl), $C_1$-$C_4$ haloalkyl (such as trifluoromethyl), $C_1$-$C_4$ alkoxy (such as methoxy), $C_1$-$C_4$ haloalkoxy and cyano;

T and T' are independently a covalent bond or optionally substituted lower alkylene (such as where T and T' are both absent); and $R_4$ taken together with $R_{12}$ form an optionally substituted imidazolyl.

In some embodiments,
one of W, X, Y, and Z is N and the others are C;
$R_1$ is benzyl, halobenzyl, methoxybenzyl, cyanobenzyl, or naphthalenylmethyl; $R_2$ is optionally substituted $C_1$-$C_4$ alkyl;
$R_{2'}$ is hydrogen;
$R_5$, $R_6$, $R_7$, and $R_8$ are independently chosen from hydrogen, amino, alkylamino, dialkylamino, hydroxyl, halogen (such as chloro and fluoro), $C_1$-$C_4$ alkyl (such as methyl), $C_1$-$C_4$ haloalkyl (such as trifluoromethyl), $C_1$-$C_4$ alkoxy (such as methoxy), $C_1$-$C_4$ haloalkoxy and cyano;
T and T' are independently a covalent bond or optionally substituted lower alkylene (such as where T and T' are both absent); and
$R_4$ taken together with $R_{12}$ form an optionally substituted imidazolidinyl ring.

In some embodiments,
one of W, X, Y, and Z is N and the others are C;
$R_1$ is benzyl, halobenzyl, methoxybenzyl, cyanobenzyl, or naphthalenylmethyl;
$R_2$ is optionally substituted $C_1$-$C_4$ alkyl;
$R_{2'}$ is hydrogen;
$R_5$, $R_6$, $R_7$, and $R_8$ are independently chosen from hydrogen, amino, alkylamino, dialkylamino, hydroxyl, halogen (such as chloro and fluoro), $C_1$-$C_4$ alkyl (such as methyl), $C_1$-$C_4$ haloalkyl (such as trifluoromethyl), $C_1$-$C_4$ alkoxy (such as methoxy), $C_1$-$C_4$ haloalkoxy and cyano;
T and T' are independently a covalent bond or optionally substituted lower alkylene (such as where T and T' are both absent); and
$R_4$ taken together with $R_{12}$ form an optionally substituted piperazinyl ring.

In some embodiments,
one of W, X, Y, and Z is N and the others are C;
$R_1$ is benzyl, halobenzyl, methoxybenzyl, cyanobenzyl, or naphthalenylmethyl;
$R_2$ is optionally substituted $C_1$-$C_4$ alkyl;
$R_{2'}$ is hydrogen;
$R_5$, $R_6$, $R_7$, and $R_8$ are independently chosen from hydrogen, amino, alkylamino, dialkylamino, hydroxyl, halogen (such as chloro and fluoro), $C_1$-$C_4$ alkyl (such as methyl), $C_1$-$C_4$ haloalkyl (such as trifluoromethyl), $C_1$-$C_4$ alkoxy (such as methoxy), $C_1$-$C_4$ haloalkoxy and cyano;
T and T' are independently a covalent bond or optionally substituted lower alkylene (such as where T and T' are both absent); and
$R_4$ taken together with $R_{12}$ form an optionally substituted diazepinoyl ring.

Compounds of Formula II
When considering the compounds of Formula II, in some embodiments,
$R_1$ is benzyl, halobenzyl, methoxybenzyl-, cyanobenzyl, or naphthalenylmethyl-;
$R_2$ is optionally substituted $C_1$-$C_4$ alkyl;
$R_{2'}$ is hydrogen;
$R_5$, $R_6$, $R_7$, and $R_8$ are independently chosen from hydrogen, amino, alkylamino, dialkylamino, hydroxyl, halogen (such as chloro and fluoro), $C_1$-$C_4$ alkyl (such as methyl), $C_1$-$C_4$ haloalkyl (such as trifluoromethyl), $C_1$-$C_4$ alkoxy (such as methoxy), $C_1$-$C_4$ haloalkoxy and cyano;
one of T and T' is absent and the other is optionally substituted alkylene;

$R_{12}$ is —$C(O)R_3$ wherein $R_3$ is optionally substituted $C_1$-$C_8$ alkyl (e.g., $C_1$-$C_8$ alkyl substituted with lower-alkoxy), optionally substituted heteroaryl, and optionally substituted aryl (such as halophenyl, halomethylphenyl-, methylenedioxyphenyl-, methoxyphenyl-, ethoxyphenyl-, cyanophenyl- or phenyl substituted with lower-acyl or lower-alkylaminocarbonyl-, e.g. methylaminocarbonyl- or ethylaminocarbonyl-, or di(lower-alkyl) aminocarbonyl-, e.g. dimethylaminocarbonyl- or diethylaminocarbonyl- or lower alkyl); and $R_4$ is $R_{16}$-alkylene-, wherein $R_{16}$ is amino, $C_1$-$C_4$ alkylamino-, di($C_1$-$C_4$ alkyl)amino-, $C_1$-$C_4$ alkoxy-, hydroxyl, or N-heterocyclyl.

In some embodiments, $R_1$ is benzyl, halobenzyl, methoxybenzyl, cyanobenzyl, or naphthalenylmethyl; and $R_2$ is propyl (such as i- or c-propyl).

In some embodiments,
$R_1$ is benzyl, halobenzyl, methoxybenzyl, cyanobenzyl, or naphthalenylmethyl;
$R_2$ is optionally substituted $C_1$-$C_4$ alkyl;
$R_{2'}$ is hydrogen;
$R_5$, $R_6$, $R_7$, and $R_8$ are independently chosen from hydrogen, amino, alkylamino, dialkylamino, hydroxyl, halogen (such as chloro and fluoro), $C_1$-$C_4$ alkyl (such as methyl), $C_1$-$C_4$ haloalkyl (such as trifluoromethyl), $C_1$-$C_4$ alkoxy (such as methoxy), $C_1$-$C_4$ haloalkoxy and cyano;
one of T and T' is absent and the other is optionally substituted alkylene; and
$R_4$ taken together with $R_{12}$ form an optionally substituted imidazolyl.

In some embodiments,
$R_1$ is benzyl, halobenzyl, methoxybenzyl, cyanobenzyl, or naphthalenylmethyl;
$R_2$ is optionally substituted $C_1$-$C_4$ alkyl;
$R_{2'}$ is hydrogen;
$R_5$, $R_6$, $R_7$, and $R_8$ are independently chosen from hydrogen, amino, alkylamino, dialkylamino, hydroxyl, halogen (such as chloro and fluoro), $C_1$-$C_4$ alkyl (such as methyl), $C_1$-$C_4$ haloalkyl (such as trifluoromethyl), $C_1$-$C_4$ alkoxy (such as methoxy), $C_1$-$C_4$ haloalkoxy and cyano;
one of T and T' is absent and the other is optionally substituted alkylene; and
$R_4$ taken together with $R_{12}$ form an optionally substituted imidazolidinyl ring.

In some embodiments,
$R_1$ is benzyl, halobenzyl, methoxybenzyl, cyanobenzyl, or naphthalenylmethyl;
$R_2$ is optionally substituted $C_1$-$C_4$ alkyl;
$R_{2'}$ is hydrogen;
$R_5$, $R_6$, $R_7$, and $R_8$ are independently chosen from hydrogen, amino, alkylamino, dialkylamino, hydroxyl, halogen (such as chloro and fluoro), $C_1$-$C_4$ alkyl (such as methyl), $C_1$-$C_4$ haloalkyl (such as trifluoromethyl), $C_1$-$C_4$ alkoxy (such as methoxy), $C_1$-$C_4$ haloalkoxy and cyano;
one of T and T' is absent and the other is optionally substituted alkylene; and
$R_4$ taken together with $R_{12}$ form an optionally substituted piperazinyl ring.

In some embodiments,
$R_1$ is benzyl, halobenzyl, methoxybenzyl, cyanobenzyl, or naphthalenylmethyl;
$R_2$ is optionally substituted $C_1$-$C_4$ alkyl;
$R_{2'}$ is hydrogen;

$R_5$, $R_6$, $R_7$, and $R_8$ are independently chosen from hydrogen, amino, alkylamino, dialkylamino, hydroxyl, halogen (such as chloro and fluoro), $C_1$-$C_4$ alkyl (such as methyl), $C_1$-$C_4$ haloalkyl (such as trifluoromethyl), $C_1$-$C_4$ alkoxy (such as methoxy), $C_1$-$C_4$ haloalkoxy and cyano;

one of T and T' is absent and the other is optionally substituted alkylene; and $R_4$ taken together with $R_{12}$ form an optionally substituted diazepinoyl ring.

Compounds of Formula III

When considering the compounds of Formula III, in some embodiments, $R_1$ is benzyl, halobenzyl, methoxybenzyl, cyanobenzyl, or naphthalenylmethyl;

$R_2$ is optionally substituted $C_1$-$C_4$ alkyl;

$R_{2'}$ is hydrogen;

$R_5$, $R_6$, $R_7$, and $R_8$ are independently chosen from hydrogen, amino, alkylamino, dialkylamino, hydroxyl, halogen (such as chloro and fluoro), $C_1$-$C_4$ alkyl (such as methyl), $C_1$-$C_4$ haloalkyl (such as trifluoromethyl), $C_1$-$C_4$ alkoxy (such as methoxy), $C_1$-$C_4$ haloalkoxy and cyano; and $R_4$ taken together with $R_{12}$ form an optionally substituted piperazinyl ring.

In some embodiments, $R_1$ is benzyl, halobenzyl, methoxybenzyl, cyanobenzyl, or naphthalenylmethyl;

$R_2$ is optionally substituted $C_1$-$C_4$ alkyl;

$R_{2'}$ is hydrogen;

$R_5$, $R_6$, $R_7$, and $R_8$ are independently chosen from hydrogen, amino, alkylamino, dialkylamino, hydroxyl, halogen (such as chloro and fluoro), $C_1$-$C_4$ alkyl (such as methyl), $C_1$-$C_4$ haloalkyl (such as trifluoromethyl), $C_1$-$C_4$ alkoxy (such as methoxy), $C_1$-$C_4$ haloalkoxy and cyano; and $R_4$ taken together with $R_{12}$ form an optionally substituted diazepinoyl ring.

Once made, the compounds of the invention find use in a variety of applications involving alteration of mitosis. As will be appreciated by those skilled in the art, mitosis may be altered in a variety of ways; that is, one can affect mitosis either by increasing or decreasing the activity of a component in the mitotic pathway. Stated differently, mitosis may be affected (e.g., disrupted) by disturbing equilibrium, either by inhibiting or activating certain components. Similar approaches may be used to alter meiosis.

In some embodiments, the compounds of the invention are used to inhibit mitotic spindle formation, thus causing prolonged cell cycle arrest in mitosis. By "inhibit" in this context is meant decreasing or interfering with mitotic spindle formation or causing mitotic spindle dysfunction. By "mitotic spindle formation" herein is meant organization of microtubules into bipolar structures by mitotic kinesins. By "mitotic spindle dysfunction" herein is meant mitotic arrest and monopolar spindle formation.

The compounds of the invention are useful to bind to, and/or inhibit the activity of, a mitotic kinesin, KSP. In some embodiments, the KSP is human KSP, although the compounds may be used to bind to or inhibit the activity of KSP kinesins from other organisms. In this context, "inhibit" means either increasing or decreasing spindle pole separation, causing malformation, i.e., splaying, of mitotic spindle poles, or otherwise causing morphological perturbation of the mitotic spindle. Also included within the definition of KSP for these purposes are variants and/or fragments of KSP. See U.S. Pat. No. 6,437,115, hereby incorporated by reference in its entirety. The compounds of the invention have been shown to have specificity for KSP. However, the present invention includes the use of the compounds to bind to or modulate other mitotic kinesins.

The compounds of the invention are used to treat cellular proliferation diseases. Such disease states which can be treated by the compounds, compositions and methods provided herein include, but are not limited to, cancer (further discussed below), autoimmune disease, fungal disorders, arthritis, graft rejection, inflammatory bowel disease, cellular proliferation induced after medical procedures, including, but not limited to, surgery, angioplasty, and the like. Treatment includes inhibiting cellular proliferation. It is appreciated that in some cases the cells may not be in an abnormal state and still require treatment. Thus, in some embodiments, the invention herein includes application to cells or individuals afflicted or subject to impending affliction with any one of these disorders or states.

The compounds, compositions and methods provided herein are useful for the treatment of cancer including solid tumors such as skin, breast, brain, cervical carcinomas, testicular carcinomas, etc. In some embodiments, cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above identified conditions.

For assay of KSP-modulating activity, generally either KSP or a compound according to the invention is non-diffusably bound to an insoluble support having isolated sample receiving areas (e.g., a microtiter plate, an array, etc.). The insoluble support may be made of any material to which the sample can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, Teflon™, etc. Microtiter plates and arrays are convenient because a large number of assays can be carried out simultaneously, using small amounts of reagents and samples. The manner of binding of the sample is not crucial so long as it is compatible with the reagents and overall methods of the invention, maintains the activity of the sample and is nondiffusable. Methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. Following binding of the sample, excess unbound material is removed by washing. The sample receiving areas may then be blocked through incubation with bovine serum albumin (BSA), casein or other innocuous protein or other moiety.

The compounds of the invention may be used on their own to inhibit the activity of a mitotic kinesin, such as KSP. In some embodiments, a compound of the invention is combined with KSP and the activity of KSP is assayed. Kinesin (including KSP) activity is known in the art and includes one or more kinesin activities. Kinesin activities include the ability to affect ATP hydrolysis; microtubule binding; gliding and polymerization/depolymerization (effects on microtubule dynamics); binding to other proteins of the spindle; binding to proteins involved in cell-cycle control; serving as a substrate to other enzymes, such as kinases or proteases; and specific kinesin cellular activities such as spindle pole separation.

Methods of performing motility assays are well known to those of skill in the art. (See e.g., Hall, et al. (1996), Biophys. J., 71: 3467-3476, Turner et al., 1996, AnaL Biochem. 242 (1):20-5; Gittes et al., 1996, Biophys. J. 70(1): 418-29; Shirakawa et al., 1995, J. Exp. BioL 198: 1809-15; Winkelmann et al., 1995, Biophys. J. 68: 2444-53; Winkelmann et al., 1995, Biophys. J. 68: 72S.)

Methods known in the art for determining ATPase hydrolysis activity also can be used. Suitably, solution based assays are utilized. U.S. Pat. No. 6,410,254, hereby incorporated by reference in its entirety, describes such assays. Alternatively, conventional methods are used. For example, Pi release from kinesin can be quantified. In some embodiments, the ATPase hydrolysis activity assay utilizes 0.3 M PCA (perchloric acid) and malachite green reagent (8.27 mM sodium molybdate II, 0.33 mM malachite green oxalate, and 0.8 mM Triton X-100). To perform the assay, 10 µL of the reaction mixture is quenched in 90 µL of cold 0.3 M PCA. Phosphate standards are used so data can be converted to mM inorganic phosphate released. When all reactions and standards have been quenched in PCA, 100 µL of malachite green reagent is added to the relevant wells in e.g., a microtiter plate. The mixture is developed for 10-15 minutes and the plate is read at an absorbance of 650 nm. If phosphate standards were used, absorbance readings can be converted to mM $P_i$ and plotted over time. Additionally, ATPase assays known in the art include the luciferase assay.

ATPase activity of kinesin motor domains also can be used to monitor the effects of agents and are well known to those skilled in the art. In some embodiments ATPase assays of kinesin are performed in the absence of microtubules. In some embodiments, the ATPase assays are performed in the presence of microtubules. Different types of agents can be detected in the above assays. In some embodiments, the effect of an agent is independent of the concentration of microtubules and ATP. In some embodiments, the effect of the agents on kinesin ATPase can be decreased by increasing the concentrations of ATP, microtubules or both. In some embodiments, the effect of the agent is increased by increasing concentrations of ATP, microtubules or both.

Compounds that inhibit the biochemical activity of KSP in vitro may then be screened in vivo. In vivo screening methods include assays of cell cycle distribution, cell viability, or the presence, morphology, activity, distribution, or number of mitotic spindles. Methods for monitoring cell cycle distribution of a cell population, for example, by flow cytometry, are well known to those skilled in the art, as are methods for determining cell viability. See for example, U.S. Pat. No. 6,437,115, hereby incorporated by reference in its entirety. Microscopic methods for monitoring spindle formation and malformation are well known to those of skill in the art (see, e.g., Whitehead and Rattner (1998), J. Cell Sci. 111:2551-61; Galgio et al, (1996) J. Cell Biol., 135:399-414), each incorporated herein by reference in its entirety.

The compounds of the invention inhibit the KSP kinesin. One measure of inhibition is $IC_{50}$, defined as the concentration of the compound at which the activity of KSP is decreased by fifty percent relative to a control. In some embodiments, compounds have $IC_{50}$'s of less than about 1 mM. In some embodiments, compounds have $IC_{50}$'s of less than about 100 µM. In some embodiments, compounds have $IC_{50}$'s of less than about 10 µM. In some embodiments, compounds have $IC_{50}$'s of less than about 1 µM. In some embodiments, compounds have $IC_{50}$'s of less than about 100 nM. In some embodiments, compounds have $IC_{50}$'s of less than about 10 nM. Measurement of $IC_{50}$ is done using an ATPase assay such as described herein.

Another measure of inhibition is $K_i$. For compounds with $IC_{50}$'s less than 1 µM, the $K_i$ or $K_d$ is defined as the dissociation rate constant for the interaction of the compounds described herein with KSP. In some embodiments, compounds have compounds have $K_i$'s of less than about 100 µM. In some embodiments, compounds have $K_i$'s of less than about 10 µM. In some embodiments, compounds have $K_i$'s of less than about 1 µM. In some embodiments, compounds have $K_i$'s of less than about 100 nM. In some embodiments, compounds have $K_i$'s of less than about 10 nM.

The $K_i$ for a compound is determined from the $IC_{50}$ based on three assumptions and the Michaelis-Menten equation. First, only one compound molecule binds to the enzyme and there is no cooperativity. Second, the concentrations of active enzyme and the compound tested are known (i.e., there are no significant amounts of impurities or inactive forms in the preparations). Third, the enzymatic rate of the enzyme-inhibitor complex is zero. The rate (i.e., compound concentration) data are fitted to the equation:

$$V = V_{\max}E_0\left[1 - \frac{(E_0 + I_0 + Kd) - \sqrt{(E_0 + I_0 + Kd)^2 - 4E_0I_0}}{2E_0}\right]$$

where V is the observed rate, $V_{max}$ is the rate of the free enzyme, $I_0$ is the inhibitor concentration, $E_0$ is the enzyme concentration, and $K_d$ is the dissociation constant of the enzyme-inhibitor complex.

Another measure of inhibition is $GI_{50}$, defined as the concentration of the compound that results in a decrease in the rate of cell growth by fifty percent. In some embodiments, compounds have $GI_{50}$'s of less than about 1 mM. In some embodiments, compounds have a $GI_{50}$ of less than about 20 µM. In some embodiments, compounds have a $GI_{50}$ of less than about 10 µM. In some embodiments, compounds have a $GI_{50}$ of less than about 1 µM. In some embodiments, compounds have a $GI_{50}$ of less than about 100 nM. In some embodiments, compounds have a $GI_{50}$ of less than about 10 nM. Measurement of $GI_{50}$ is done using a cell proliferation assay such as described herein. Compounds of this class were found to inhibit cell proliferation.

In vitro potency of small molecule inhibitors is determined, for example, by assaying human ovarian cancer cells (SKOV3) for viability following a 72-hour exposure to a 9-point dilution series of compound. Cell viability is determined by measuring the absorbance of formazon, a product formed by the bioreduction of MTS/PMS, a commercially available reagent. Each point on the dose-response curve is calculated as a percent of untreated control cells at 72 hours minus background absorption (complete cell kill).

Anti-proliferative compounds that have been successfully applied in the clinic to treatment of cancer (cancer chemotherapeutics) have $GI_{50}$'s that vary greatly. For example, in A549 cells, paclitaxel $GI_{50}$ is 4 nM, doxorubicin is 63 nM, 5-fluorouracil is 1 µM, and hydroxyurea is 500 µM (data provided by National Cancer Institute, Developmental Therapeutic Program, http://dtp.nci.nih.gov/). Therefore, compounds that inhibit cellular proliferation, irrespective of the concentration demonstrating inhibition, have potential clinical usefulness.

To employ the compounds of the invention in a method of screening for compounds that bind to KSP kinesin, the KSP is bound to a support, and a compound of the invention is added to the assay. Alternatively, the compound of the invention is bound to the support and KSP is added. Classes of compounds among which novel binding agents may be sought include specific antibodies, non-natural binding agents identified in screens of chemical libraries, peptide analogs, etc. In some embodiments, candidate agents are screened a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the compound of the invention to KSP may be done in a number of ways. In some embodiments, the compound is labeled, for example, with a fluorescent or radioactive moiety, and binding is determined directly. For example, this may be done by attaching all or a portion of KSP to a solid support, adding a labeled test compound (for example a compound of the invention in which at least one atom has been replaced by a detectable isotope), washing off excess reagent, and determining whether the amount of the label is that present on the solid support.

By "labeled" herein is meant that the compound is either directly or indirectly labeled with a label which provides a detectable signal, e.g., radioisotope, fluorescent tag, enzyme, antibodies, particles such as magnetic particles, chemiluminescent tag, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, the kinesin proteins may be labeled at tyrosine positions using $^{125}I$, or with fluorophores. Alternatively, more than one component may be labeled with different labels; using $^{125}I$ for the proteins, for example, and a fluorophor for the antimitotic agents.

The compounds of the invention may also be used as competitors to screen for additional drug candidates. "Candidate agent" or "drug candidate" or grammatical equivalents as used herein describe any molecule, e.g., protein, oligopeptide, small organic molecule, polysaccharide, polynucleotide, etc., to be tested for bioactivity. They may be capable of directly or indirectly altering the cellular proliferation phenotype or the expression of a cellular proliferation sequence, including both nucleic acid sequences and protein sequences. In other cases, alteration of cellular proliferation protein binding and/or activity is screened. Screens of this sort may be performed either in the presence or absence of microtubules. In the case where protein binding or activity is screened, some embodiments exclude molecules already known to bind to that protein, for example, polymer structures such as microtubules, and energy sources such as ATP. Some embodiments of assays herein include candidate agents which do not bind the cellular proliferation protein in its endogenous native state termed herein as "exogenous" agents. In some embodiments, exogenous agents further exclude antibodies to KSP.

Candidate agents can encompass numerous chemical classes, though typically they are organic molecules, such as small organic compounds having a molecular weight of more than 100 and less than about 2,500 daltons. Candidate agents comprise functional groups necessary for structural interaction with proteins, such as hydrogen bonding and lipophilic binding, and typically include at least an amine, carbonyl-, hydroxyl-, ether, or carboxyl group, often, at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, and/or amidification to produce structural analogs.

Competitive screening assays may be done by combining KSP and a drug candidate in a first sample. A second sample comprises a compound of the present invention, KSP and a drug candidate. This may be performed in either the presence or absence of microtubules. The binding of the drug candidate is determined for both samples, and a change, or difference in binding between the two samples indicates the presence of a drug candidate capable of binding to KSP and potentially inhibiting its activity. That is, if the binding of the drug candidate is different in the second sample relative to the first sample, the drug candidate is capable of binding to KSP.

In some embodiments, the binding of the candidate agent to KSP is determined through the use of competitive binding assays. In some embodiments, the competitor is a binding moiety known to bind to KSP, such as an antibody, peptide, binding partner, ligand, etc. Under certain circumstances, there may be competitive binding as between the candidate agent and the binding moiety, with the binding moiety displacing the candidate agent.

In some embodiments, the candidate agent is labeled. Either the candidate agent, or the competitor, or both, is added first to KSP for a time sufficient to allow binding, if present. Incubations may be performed at any temperature which facilitates optimal activity, typically between 4 and 40° C. Incubation periods are selected for optimum activity, but may also be optimized to facilitate rapid high throughput screening. Typically between 0.1 and 1 hour will be sufficient. Excess reagent is generally removed or washed away. The second component is then added, and the presence or absence of the labeled component is followed, to indicate binding.

In some embodiments, the competitor is added first, followed by the candidate agent. Displacement of the competitor is an indication the candidate agent is binding to KSP and thus is capable of binding to, and potentially inhibiting, the activity of KSP. In some embodiments, either component can be labeled. Thus, for example, if the competitor is labeled, the presence of label in the wash solution indicates displacement by the agent. Alternatively, if the candidate agent is labeled, the presence of the label on the support indicates displacement.

In some embodiments, the candidate agent is added first, with incubation and washing, followed by the competitor. The absence of binding by the competitor may indicate the candidate agent is bound to KSP with a higher affinity. Thus, if the candidate agent is labeled, the presence of the label on the support, coupled with a lack of competitor binding, may indicate the candidate agent is capable of binding to KSP.

Inhibition is tested by screening for candidate agents capable of inhibiting the activity of KSP comprising the steps of combining a candidate agent with KSP, as above, and determining an alteration in the biological activity of KSP. In some embodiments, the candidate agent should both bind to KSP (although this may not be necessary), and alter its biological or biochemical activity as defined herein. The methods include both in vitro screening methods and in vivo screening of cells for alterations in cell cycle distribution, cell viability, or for the presence, morpohology, activity, distribution, or amount of mitotic spindles, as are generally outlined above.

Alternatively, differential screening may be used to identify drug candidates that bind to the native KSP, but cannot bind to modified KSP.

Positive controls and negative controls may be used in the assays. Suitably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g., albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

Accordingly, the compounds of the invention are administered to cells. By "administered" herein is meant administration of a therapeutically effective dose of a compound of the invention to a cell either in cell culture or in a patient. By "therapeutically effective dose" herein is meant a dose that produces the effects for which it is administered. The exact dose will depend on the purpose of the treatment, and will be ascertainable by one skilled in the art using known techniques. As is known in the art, adjustments for systemic versus localized delivery, age, body weight, general health, sex, diet, time of administration, drug interaction and the severity of the condition may be necessary, and will be ascertainable with routine experimentation by those skilled in the art. By "cells" herein is meant any cell in which mitosis or meiosis can be altered.

A "patient" for the purposes of the present invention includes both humans and other animals, such as mammals, and other organisms. Thus the methods are applicable to both human therapy and veterinary applications. In some embodiments the patient is a mammal. In some embodiments, the patient is human.

Compounds of the invention having the desired pharmacological activity may be administered, generally as a pharmaceutically acceptable composition comprising an pharmaceutical excipient, to a patient, as described herein. Depending upon the manner of introduction, the compounds may be formulated in a variety of ways as discussed below. The concentration of therapeutically active compound in the formulation may vary from about 0.1-100 wt. %.

The agents may be administered alone or in combination with other treatments, i.e., radiation, or other chemotherapeutic agents such as the taxane class of agents that appear to act on microtubule formation or the camptothecin class of topoisomerase I inhibitors. When used, other chemotherapeutic agents may be administered before, concurrently, or after administration of a compound of the present invention. In one aspect of the invention, a compound of the present invention is co-administered with one or more other chemotherapeutic agents. By "co-administer" it is meant that the present compounds are administered to a patient such that the present compounds as well as the co-administered compound may be found in the patient's bloodstream at the same time, regardless when the compounds are actually administered, including simultaneously.

The administration of the compounds and compositions of the present invention can be done in a variety of ways, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds and inflammation, the compound or composition may be directly applied as a solution or spray.

Pharmaceutical dosage forms include a compound of Formula I, II, or III or a pharmaceutically acceptable salt, solvate, or solvate of a salt thereof, and one or more pharmaceutical excipients. As is known in the art, pharmaceutical excipients are secondary ingredients which function to enable or enhance the delivery of a drug or medicine in a variety of dosage forms (e.g.: oral forms such as tablets, capsules, and liquids; topical forms such as dermal, opthalmic, and otic forms; suppositories; injectables; respiratory forms and the like). Pharmaceutical excipients include inert or inactive ingredients, synergists or chemicals that substantively contribute to the medicinal effects of the active ingredient. For example, pharmaceutical excipients may function to improve flow characteristics, product uniformity, stability, taste, or appearance, to ease handling and administration of dose, for convenience of use, or to control bioavailability. While pharmaceutical excipients are commonly described as being inert or inactive, it is appreciated in the art that there is a relationship between the properties of the pharmaceutical excipients and the dosage forms containing them.

Pharmaceutical excipients suitable for use as carriers or diluents are well known in the art, and may be used in a variety of formulations. See, e.g., Remington's Pharmaceutical Sciences, 18th Edition, A. R. Gennaro, Editor, Mack Publishing Company (1990); Remington: The Science and Practice of Pharmacy, 20th Edition, A. R. Gennaro, Editor, Lippincott Williams & Wilkins (2000); Handbook of Pharmaceutical Excipients, 3rd Edition, A. H. Kibbe, Editor, American Pharmaceutical Association, and Pharmaceutical Press (2000); and Handbook of Pharmaceutical Additives, compiled by Michael and Irene Ash,Gower (1995), each of which is incorporated herein by reference for all purposes.

Oral solid dosage forms such as tablets will typically comprise one or more pharmaceutical excipients, which may for example help impart satisfactory processing and compression characteristics, or provide additional desirable physical characteristics to the tablet. Such pharmaceutical excipients may be selected from diluents, binders, glidants, lubricants, disintegrants, colors, flavors, sweetening agents, polymers, waxes or other solubility-retarding materials.

Compositions for intravenous administration will generally comprise intravenous fluids, i.e., sterile solutions of simple chemicals such as sugars, amino acids or electrolytes, which can be easily carried by the circulatory system and assimilated. Such fluids are prepared with water for injection USP.

Fluids used commonly for intravenous (IV) use are disclosed in Remington, the Science and Practice of Pharmacy [full citation previously provided], and include:
alcohol (e.g., in dextrose and water ("D/W") [e.g., 5% dextrose] or dextrose and water [e.g., 5% dextrose] in normal saline solution ("NSS"); e.g. 5% alcohol);
synthetic amino acid such as Aminosyn, FreAmine, Travasol, e.g., 3.5 or 7; 8.5; 3.5, 5.5 or 8.5% respectively;
ammonium chloride e.g., 2.14%;
dextran 40, in NSS e.g., 10% or in D5/W e.g., 10%;
dextran 70, in NSS e.g., 6% or in D5/W e.g., 6%;
dextrose (glucose, D5/W) e.g., 2.5-50%;
dextrose and sodium chloride e.g., 5-20% dextrose and 0.22-0.9% NaCl;
lactated Ringer's (Hartmann's) e.g., NaCl 0.6%, KCl 0.03%, $CaCl_2$ 0.02%;
lactate 0.3%;
mannitol e.g., 5%, optionally in combination with dextrose e.g., 10% or NaCl e.g., 15 or 20%;
multiple electrolyte solutions with varying combinations of electrolytes, dextrose, fructose, invert sugar Ringer's e.g., NaCl 0.86%, KCl 0.03%, $CaCl_2$ 0.033%;
sodium bicarbonate e.g., 5%;
sodium chloride e.g., 0.45, 0.9, 3, or 5%;
sodium lactate e.g., 1/6 M; and
sterile water for injection The pH of such fluids may vary, and will typically be from 3.5 to 8 such as known in the art.

All references and publications, including but not limited to patents and patent applications, cited in this specification are herein incorporated by reference as if each individual reference and publication were specifically and inidividually indicated to be incorporated by reference herein as though fully set forth.

It is to be understood that the present invention covers all combinations of subgroups described herein above.

The application of which this description and claims forms part may be used as a basis for priority in respect of any subsequent application.

The following examples serve to more fully describe the manner of using the above-described invention. It is understood that these examples in no way serve to limit the true scope of this invention, but rather are presented for illustrative purposes.

EXAMPLES

Example 1

Inhibition of Cellular Viability in Tumor Cell Lines Treated with KSP Inhibitors.r Materials and Solutions:
Cells: SKOV3, Ovarian Cancer (human).
Media: Phenol Red Free RPMI+5% Fetal Bovine Serum+2 mM L-glutamine.
Colorimetric Agent for Determining Cell Viability: Promega MTS tetrazolium compound.
Control Compound for max cell kill: Topotecan, 1 µM.

Procedure: Day 1—Cell Plating:
Adherent SKOV3 cells are washed with 10 mLs of PBS followed by the addition of 2 mLs of 0.25% trypsin and incubation for 5 minutes at 37° C. The cells are rinsed from the flask using 8 mL of media (phenol red-free RPMI+5% FBS) and transferred to fresh flask. Cell concentration is determined using a Coulter counter and the appropriate volume of cells to achieve 1000 cells/100 µL is calculated. 100 µL of media cell suspension (adjusted to 1000 cells/ 100 µL) is added to all wells of 96-well plates, followed by incubation for 18 to 24 hours at 37° C., 100% humidity, and 5% $CO_2$, allowing the cells to adhere to the plates.

Procedure: Day 2—Compound Addition:
To one column of the wells of an autoclaved assay block are added an initial 2.5 µL of test compound(s) at 400X the highest desired concentration. 1.25 μL of 400X (400 μM) Topotecan is added to other wells (optical density's from these wells are used to subtract out for background absorbance of dead cells and vehicle). 500 μL of media without DMSO are added to the wells containing test compound, and 250 μL to the Topotecan wells. 250 μL of media+0.5% DMSO is added to all remaining wells, into which the test compound(s) are serially diluted. By row, compound-containing media is replica plated (in duplicate) from the assay block to the corresponding cell plates. The cell plates are incubated for 72 hours at 37° C., 100% humidity, and 5% $CO_2$.

Procedure: Day 4—MTS Addition and OD Reading:

The plates are removed from the incubator and 40 μl MTS/PMS is added to each well. Plates are then incubated for 120 minutes at 37° C., 100% humidity, 5% $CO_2$, followed by reading the ODs at 490 nm after a 5 second shaking cycle in a ninety-six well spectrophotometer.

Data Analysis

The normalized % of control (absorbance-background) is calculated and an XLfit is used to generate a dose-response curve from which the concentration of compound required to inhibit viability by 50% is determined. The compounds of the present invention have activity when tested by this method as described above.

Example 2

Enantiomer Separation

In general, the procedures described above can be used to prepare substantially pure or enriched R— or S-enantiomers by selected a starting amino acid of the appropriate R— or S-configuration. In some embodiments, compounds have an R-configuration at the stereogenic center to which $R_2$ is attached. An R:S mixture can be separated into its constituent pure enantiomers by methods well known to those skilled in the art. These include the formation and separation of diastereomeric derivatives such as those formed by reaction with an optically pure acid such as dibenzoyltartaric acid. Alternatively, separation can be accomplished by chiral chromatography, for example, using the following conditions:

Column: Chiralcel OD 20×250 mm;
Sample loaded ~100 mg mL$^{-1}$ in 1:2 ethanol:hexane containing 0.01% isopropylamine;
Chromatography conditions: isocratic elution with 1:2 ethanol:hexane containing 0.01% isopropylamine at a flow rate of 15 mL min$^{-1}$;
UV detection at 254 nm.

Example 3

Monopolar Spindle Formation Following Application of a KSP Inhibitor

Human tumor cells Skov-3 (ovarian) are plated in 96-well plates at densities of 4,000 cells per well, allowed to adhere for 24 hours, and treated with various concentrations of the pyridmidinone derivatives for 24 hours. Cells are fixed in 4% formaldehyde and stained with antitubulin antibodies (subsequently recognized using fluorescently-labeled secondary antibody) and Hoechst dye (which stains DNA).

Visual inspection reveal that the compounds caused cell cycle arrest in the prometaphase stage of mitosis. DNA is condensed and spindle formation is initiated, but arrested cells uniformly display monopolar spindles, indicating that there is an inhibition of spindle pole body separation. Microinjection of anti-KSP antibodies also causes mitotic arrest with arrested cells displaying monopolar spindles.

Example 4

Inhibition of Cellular Proliferation in Tumor Cell Lines Treated with KSP Inhibitors.

Cells are plated in 96-well plates at densities from 1000-2500 cells/well of a 96-well plate and allowed to adhere/grow for 24 hours. They are then treated with various concentrations of drug for 48 hours. The time at which compounds are added is considered $T_0$. A tetrazolium-based assay using the reagent 3-(4,5-dimethylthiazol-2-yl)-5-(3-carboxymethoxyphenyl)-2-(4-sulfophenyl)-2H-tetrazolium (MTS) (U.S. Pat. No. 5,185,450) (see Promega product catalog #G3580, CellTiter 96®AQ$_{ueous}$ One Solution Cell Proliferation Assay) is used to determine the number of viable cells at $T_0$ and the number of cells remaining after 48 hours compound exposure. The number of cells remaining after 48 hours is compared to the number of viable cells at the time of drug addition, allowing for calculation of growth inhibition.

The growth over 48 hours of cells in control wells that are treated with vehicle only (0.25% DMSO) is considered 100% growth and the growth of cells in wells with compounds is compared to this.

A Gi$_{50}$ is calculated by plotting the concentration of compound in μM vs the percentage of cell growth in treated wells. The Gi$_{50}$ calculated for the compounds is the estimated concentration at which growth is inhibited by 50% compared to control, i.e., the concentration at which:

$$100 \times [(Treated_{48} - T_0)/(Control_{48} - T_0)] = 50$$

wherein Treated$_{48}$ is the value at 48 hours for the treated cells and Control$_{48}$ is the value at 48 hours for the control population.

All concentrations of compounds are tested in duplicate and controls are averaged over 12 wells. A very similar 96-well plate layout and Gi$_{50}$ calculation scheme is used by the National Cancer Institute (see Monks, et al., J. Natl. Cancer Inst. 83:757-766 (1991)). However, the method by which the National Cancer Institute quantitates cell number does not use MTS, but instead employs alternative methods.

Compounds of the invention inhibit cell proliferation in human ovarian tumor cell lines (SKOV-3).

Example 5

Calculation of IC$_{50}$:

Measurement of a compound's IC$_{50}$ for KSP activity uses an ATPase assay. The following solutions are used: Solution 1 consists of 3 mM phosphoenolpyruvate potassium salt (Sigma P-7127), 2 mM ATP (Sigma A-3377), 1 mM IDTT (Sigma D-9779), 5 μM paclitaxel (Sigma T-7402), 10 ppm antifoam 289 (Sigma A-8436), 25 mM Pipes/KOH pH 6.8 (Sigma P6757), 2 mM MgC12 (VWR JT400301), and 1 mM EGTA (Sigma E3889). Solution 2 consists of 1 mM NADH (Sigma N8129), 0.2 mg/ml BSA (Sigma A7906), pyruvate kinase 7 U/ml, L-lactate dehydrogenase 10 U/ml (Sigma P0294), 100 nM KSP motor domain, 50 μg/ml microtubules, 1 mM DTT (Sigma D9779), 5 μM paclitaxel (Sigma T-7402), 10 ppm antifoam 289 (Sigma A-8436), 25 mM Pipes/KOH pH 6.8 (Sigma P6757), 2 mM MgC12 (VWR JT4003-01), and 1 mM EGTA (Sigma E3889). Serial dilutions (8-12 two-fold dilutions) of the compound are made in a 96-well microtiter plate (Coming Costar 3695) using Solution 1. Following serial dilution each well has 50 µl of Solution 1. The reaction is started by adding 50 µl of solution 2 to each well. This may be done with a multichannel pipettor either manually or with automated liquid handling devices. The microplate plate is then transferred to a microplate absorbance reader and multiple absorbance readings at 340 nm are taken for each well in a kinetic mode. The observed rate of change, which is proportional to the ATPase rate, is then plotted as a function of the compound concentration. For a standard $IC_{50}$ determination the data acquired is fit by the following four parameter equation using a nonlinear fitting program (e.g., Grafit 4):

$$y = \frac{\text{Range}}{1 + \left(\frac{x}{IC_{50}}\right)^s} + \text{Background}$$

where y is the observed rate and x is the compound concentration.

What is claimed is:

1. At least one chemical entity chosen from compounds of Formula I:

Formula I and pharmaceutically acceptable salts thereof, wherein,
W, X, and Y are —C═;
Z is —N═ and $R_8$ is absent;
T and T' are each a covalent bond;
$R_1$ is chosen from optionally substituted alkyl-, optionally substituted aryl-, optionally substituted aralkyl-, optionally substituted heteroaryl-, and optionally substituted heteroaralkyl-;
$R_2$ and $R_{2'}$ are independently chosen from hydrogen, optionally substituted alkyl-, optionally substituted aryl-, optionally substituted aralkyl-, optionally substituted heteroaryl-, and optionally substituted heteroaralkyl-; or $R_2$ and $R_{2'}$ taken together form an optionally substituted 3 -to 7-membered ring;
$R_{12}$ is —C(O) —$R_3$;
$R_3$ is chosen from hydrogen, optionally substituted alkyl-, optionally substituted aryl-, optionally substituted aralkyl-, optionally substituted heteroaryl-, optionally substituted heteroaralkyl-, $R_{15}$O— and $R_{17}$—NH—;
$R_4$ is chosen from hydrogen, optionally substituted alkyl-, optionally substituted aryl-, optionally substituted aralkyl-, optionally substituted heteroaralkyl-, and optionally substituted heterocyclyl-;
$R_5$, $R_6$, and $R_7$, are independently chosen from hydrogen, acyl, optionally substituted alkyl-, optionally substituted alkoxy, halogen, hydroxyl, nitro, cyano, optionally substituted amino, alkylsulfonyl-, alkylsulfonamido-, alkylthio-, carboxyalkyl-, carboxamido-, aminocarbonyl-, optionally substituted aryl and optionally substituted heteroaryl-;
$R_8$ is absent;
$R_{15}$ is chosen from optionally substituted alkyl-, optionally substituted aryl-, optionally substituted aralkyl-, optionally substituted heteroaryl-, and optionally substituted heteroaralkyl-; and
$R_{17}$ is hydrogen, optionally substituted alkyl, optionally substituted aryl, optionally substituted aralkyl, optionally substituted heteroaryl, or optionally substituted heteroaralkyl-.

2. At least one chemical entity of claim 1 wherein $R_1$ is benzyl, halobenzyl, methylbenzyl, hydroxybenzyl, cyanobenzyl, methoxybenzyl, or naphthalenylmethyl.

3. At least one chemical entity of claim 2 wherein $R_1$ is benzyl.

4. At least one chemical entity of claim 1 wherein, $R_5$, $R_6$, and $R_7$ are independently chosen from hydrogen, hydroxyl, halo, optionally substituted $C_1$-$C_4$ alkyl-, $C_1$-$C_4$ alkoxy, cyano, amino, substituted amino, and carbamyl-.

5. At least one chemical entity of claim 4 wherein $R_5$, $R_6$, and $R_7$ are independently chosen form methoxy, methyl, trifluoromethyl, cyano, hydrogen and halo.

6. At least one chemical entity of claim 1 wherein $R_2$ is optionally substituted $C_1$-$C_4$ alkyl-, and $R_{2'}$ is hydrogen or optionally substituted $C_{1-4}$ alkyl-.

7. At least one chemical entity of claim 6 wherein $R_{2'}$ is hydrogen and $R_2$ is optionally substituted $C_1$-$C_4$ alkyl-.

8. At least one chemical entity of claim 7 wherein $R_2$ is chosen from methyl-, ethyl-, propyl, butyl, methylthioethyl-, methylthiomethyl-, aminobutyl-, (CBZ)aminobutyl-, cyclohexylmethyl-, benzyloxymethyl-, methylsulfanylethyl-, methylsulfanylmethyl-, and hydroxymethyl.

9. At least one chemical entity of claim 8 wherein $R_2$ is i-propyl.

10. At least one chemical entity of claim 1 wherein $R_4$ is $R_{16}$-alkylene-, wherein $R_{16}$ is amino, $C_1$-$C_4$ alkylamino-, di($C_1$-$C_4$ alkyl)amino-, $C_1$-$C_4$ alkoxy-, hydroxyl, or N-heterocyclyl.

11. At least one chemical entity of claim 10 wherein $R_{16}$ is amino.

12. At least one chemical entity of claim 10 wherein $R_4$ is aminopropyl.

13. At least one chemical entity of claim 1 wherein $R_3$ is chosen from optionally substituted $C_1$-$C_8$ alkyl, optionally substituted aryl-$C_1$-$C_4$-alkyl-, optionally substituted heteroaryl-$C_1$-$C_4$-alkyl-, optionally substituted heteroaryl, and optionally substituted aryl.

14. At least one chemical entity of claim 13 wherein $R_3$ is optionally substituted phenyl.

15. At least one chemical entity of claim 14 wherein $R_3$ is tolyl, halophenyl, methylhalophenyl, hydroxymethylphenyl, halo(trifluoromethyl)phenyl-, methylenedioxyphenyl, formylphenyl or cyanophenyl.

16. At least one chemical entity of claim 1 wherein
$R_1$ is benzyl, halobenzyl, methoxybenzyl-, cyanobenzyl, or naphthalenylmethyl-;
$R_2$ is optionally substituted $C_1$-$C_4$ alkyl;
$R_{2'}$ is hydrogen;
$R_5$, $R_6$, and $R_7$ are independently chosen from hydrogen, amino, alkylamino, dialkylamino, hydroxyl, halogen, $C_1$-$C_4$ alkyl, $C_1$-$C_4$ haloalkyl, $C_1$-$C_4$ alkoxy, $C_1$-$C_4$ haloalkoxy and cyano;

$R_3$ is optionally substituted $C_1$-$C_8$ alkyl, optionally substituted heteroaryl, and optionally substituted aryl; and $R_4$ is $R_{16}$-alkylene-, wherein $R_{16}$ is amino, $C_1$-$C_4$ alkylamino-, di($C_1$-$C_4$ alkyl)amino-, $C_1$-$C_4$ alkoxy-, hydroxyl, or N-heterocyclyl.

17. At least one chemical entity of claim 16 wherein $R_1$ is benzyl, halobenzyl, methoxybenzyl, cyanobenzyl, or naphthalenylmethyl; and $R_2$ is propyl.

18. A pharmaceutical composition comprising at least one chemical entity of claim 1 and at least one pharmaceutically acceptable excipient.

* * * * *

UNITED STATES PATENT AND TRADEMARK OFFICE
CERTIFICATE OF CORRECTION

| | | |
|---|---|---|
| PATENT NO. | : 7,439,254 B2 | Page 1 of 1 |
| APPLICATION NO. | : 11/005629 | |
| DATED | : October 21, 2008 | |
| INVENTOR(S) | : Bergnes | |

It is certified that error appears in the above-identified patent and that said Letters Patent is hereby corrected as shown below:

On the Title Page

Item [*] Notice:   Subject to any disclaimer, the term of this patent is extended or adjusted under 35 USC 154(b) by 539 days Delete the phrase "by 539 days" and insert -- by 858 days --

Signed and Sealed this

First Day of June, 2010

David J. Kappos
*Director of the United States Patent and Trademark Office*